United States Patent
Makino

(10) Patent No.: US 11,259,772 B2
(45) Date of Patent: Mar. 1, 2022

(54) MOBILE RADIOGRAPHIC IMAGING SYSTEM AND RADIOGRAPHIC IMAGING CASSETTE

(71) Applicant: FUJIFILM Corporation, Tokyo (JP)

(72) Inventor: Kazuhiro Makino, Kanagawa (JP)

(73) Assignee: FUJIFILM Corporation, Tokyo (JP)

(\*) Notice: Subject to any disclaimer, the term of this patent is extended or adjusted under 35 U.S.C. 154(b) by 100 days.

(21) Appl. No.: 16/691,589

(22) Filed: Nov. 21, 2019

(65) Prior Publication Data

US 2020/0170608 A1 Jun. 4, 2020

(30) Foreign Application Priority Data

Nov. 30, 2018 (JP) .............................. JP2018-225683

(51) Int. Cl.
*A61B 6/00* (2006.01)
*A61B 6/10* (2006.01)

(52) U.S. Cl.
CPC ............ *A61B 6/548* (2013.01); *A61B 6/4283* (2013.01); *A61B 6/4405* (2013.01); *A61B 6/4458* (2013.01); *A61B 6/4476* (2013.01); *A61B 6/547* (2013.01); *A61B 6/563* (2013.01); *A61B 6/102* (2013.01); *A61B 6/105* (2013.01); *A61B 6/587* (2013.01)

(58) Field of Classification Search
CPC ....... A61B 6/102; A61B 6/105; A61B 6/4283; A61B 6/4405; A61B 6/4458; A61B 6/4476; A61B 6/547; A61B 6/548; A61B 6/563; A61B 6/566; A61B 6/587
See application file for complete search history.

(56) References Cited

U.S. PATENT DOCUMENTS 7,682,077 B2 * 3/2010 Halsmer .............. A61B 6/4405
378/198
8,523,433 B2 * 9/2013 Butzine ................ A61B 6/4405
378/198

(Continued)

FOREIGN PATENT DOCUMENTS

JP 2009297517 12/2009
JP 2011245271 12/2011

(Continued)

OTHER PUBLICATIONS

Office Action of Japan Counterpart Application, with English translation thereof, dated Dec. 14, 2021, pp. 1-7.

*Primary Examiner* — Dani Fox
*Assistant Examiner* — Soorena Kefayati
(74) *Attorney, Agent, or Firm* — JCIPRNET

(57) ABSTRACT

A mobile radiographic imaging system includes a mobile radiographic imaging apparatus and a radiographic imaging cassette. The radiographic imaging apparatus includes a displacement mechanism that electrically displaces a radiation emission unit and a displacement mechanism controller that controls the operation of the displacement mechanism. The radiographic imaging cassette includes a remote operation unit that is provided in a housing to remotely operate the displacement mechanism and an operation instruction transmission unit that transmits an operation instruction for operating the displacement mechanism to the displacement mechanism controller in a case where the remote operation unit is operated.

16 Claims, 40 Drawing Sheets

(56) References Cited

U.S. PATENT DOCUMENTS

| | | | |
|---|---|---|---|
| 9,521,986 B2 | 12/2016 | Ozawa et al. | |
| 10,010,301 B2 | 7/2018 | Katsumata | |
| 2002/0017610 A1* | 2/2002 | Takemoto | A61B 6/548 250/370.09 |
| 2006/0120512 A1* | 6/2006 | Watanabe | A61B 6/10 378/198 |
| 2006/0188071 A1* | 8/2006 | Spahn | A61B 6/4283 378/196 |
| 2011/0050403 A1* | 3/2011 | Liu | G06F 1/3287 340/384.1 |
| 2011/0164721 A1* | 7/2011 | Jank | A61B 6/547 378/4 |
| 2011/0188630 A1* | 8/2011 | Ohta | A61B 6/4494 378/62 |
| 2011/0249807 A1* | 10/2011 | Dirisio | A61B 6/447 378/198 |
| 2011/0291800 A1* | 12/2011 | Butzine | A61B 6/4405 340/8.1 |
| 2012/0093294 A1* | 4/2012 | Lalena | A61B 6/468 378/98.2 |
| 2012/0177183 A1* | 7/2012 | Liu | A61B 6/4405 378/91 |
| 2012/0207273 A1* | 8/2012 | Kim | A61B 6/548 378/62 |
| 2012/0291097 A1* | 11/2012 | Jones | A61B 6/467 726/3 |
| 2013/0102245 A1* | 4/2013 | Ohguri | A61B 6/548 455/39 |
| 2013/0121477 A1* | 5/2013 | Lee | A61B 6/4476 378/198 |
| 2013/0279657 A1* | 10/2013 | Hiroike | A61B 6/4241 378/62 |
| 2013/0279661 A1* | 10/2013 | Tamura | A61B 6/542 378/98 |
| 2014/0016751 A1* | 1/2014 | Sung | A61B 6/4452 378/62 |
| 2014/0295767 A1* | 10/2014 | Iijima | A61B 6/4283 455/41.3 |
| 2014/0376700 A1* | 12/2014 | Kwak | G01B 7/30 378/205 |
| 2015/0078522 A1* | 3/2015 | Makino | G16H 40/63 378/62 |
| 2015/0078527 A1* | 3/2015 | Iwamoto | A61B 6/4405 378/91 |
| 2015/0078529 A1* | 3/2015 | Tsubota | H04W 76/10 378/98 |
| 2015/0276944 A1* | 10/2015 | Enomoto | G01T 1/175 378/101 |
| 2015/0350545 A1* | 12/2015 | Welsh | A61B 6/462 348/77 |
| 2016/0000390 A1* | 1/2016 | Uchida | A61B 6/4405 378/119 |
| 2016/0220218 A1* | 8/2016 | Zaiki | A61B 6/54 |
| 2017/0258427 A1* | 9/2017 | Risher-Kelly | A61B 6/4441 |
| 2018/0214100 A1* | 8/2018 | Kumar | A61B 6/4458 |
| 2019/0125292 A1* | 5/2019 | Nebosis | A61B 6/4405 |

FOREIGN PATENT DOCUMENTS

| | | |
|---|---|---|
| JP | 2015054178 | 3/2015 |
| JP | 2015083113 | 4/2015 |
| JP | 2015100462 | 6/2015 |
| JP | 2018007923 | 1/2018 |
| WO | 2015033445 | 3/2015 |

* cited by examiner

FIG. 15
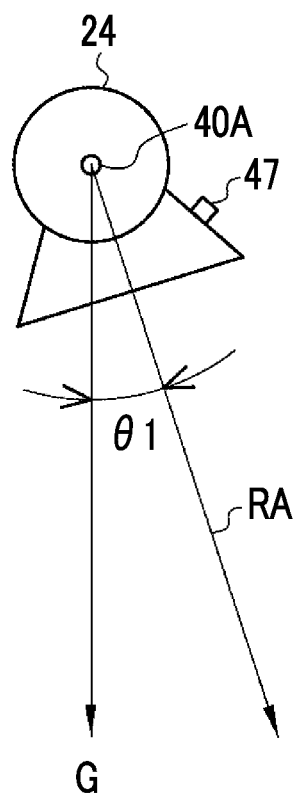
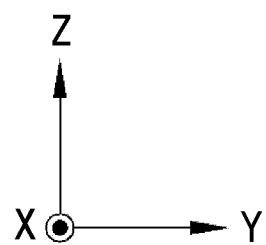

FIG. 17
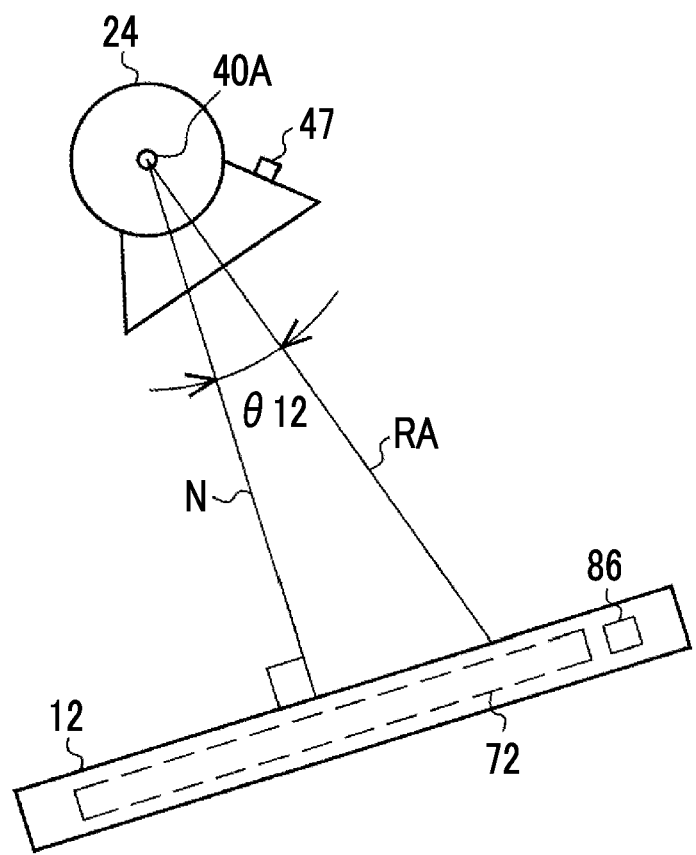
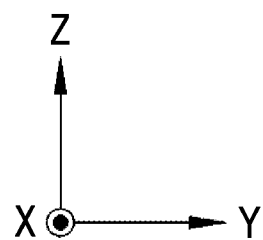

MOBILE RADIOGRAPHIC IMAGING SYSTEM AND RADIOGRAPHIC IMAGING CASSETTE

CROSS-REFERENCE TO RELATED APPLICATIONS

The present application claims priority under 35 U.S.C. § 119 to Japanese Patent Application No. 2018-225683 filed on Nov. 30, 2018. The above application is hereby expressly incorporated by reference, in its entirety, into the present application.

BACKGROUND

1. Technical Field

The technique of the present disclosure relates to a mobile radiographic imaging system and a radiographic imaging cassette.

2. Description of the Related Art

A mobile radiographic imaging apparatus that performs radiographic imaging while going around a patient room in a hospital is known (refer to JP2009-297517A and JP2011-245271A). The mobile radiographic imaging apparatus comprises a radiation emission unit and a carriage unit. The radiation emission unit has a radiation tube, and emits radiation. The radiation emission unit is mounted on the carriage unit, and the carriage unit can travel by rotation of wheels. For example, an arm and a column to which the radiation emission unit is attached are provided in the carriage unit. The direction and position of the radiation emission unit can be changed by expansion and contraction and rotation of the column and the arm.

The mobile radiographic imaging apparatus is used in combination with a radiographic imaging cassette. The radiographic imaging cassette is, for example, a portable radiographic image detector. At the time of imaging, positioning that is a relative alignment between the radiographic imaging cassette and the radiation emission unit is performed. Positioning is performed, for example, by positioning the radiographic imaging cassette at the imaging part of a patient, which is a subject, and then changing the direction and position of the radiation emission unit according to the posture and position of the radiographic imaging cassette positioned with respect to the patient.

The mobile radiographic imaging apparatus described in JP2009-297517A comprises a displacement mechanism that electrically displaces a radiation emission unit and an operation unit (user interfaces 40 to 44) that is provided in an apparatus main body to operate the displacement mechanism. The operator can change the direction and position of the radiation emission unit by operating the operation unit (paragraph 0019 and the like).

The mobile radiographic imaging apparatus described in JP2011-245271A comprises an apparatus main body and a handheld device capable of operating the apparatus main body by transmitting an operation instruction wirelessly to the apparatus main body. The handheld device can also transmit an operation instruction to move the carriage unit (X-ray base station 50) to the mobile radiographic imaging apparatus (paragraph 0018 and the like).

SUMMARY

The mobile radiographic imaging apparatus is often used by being carried into a patient room or the like in order to perform imaging for a patient who is difficult to move to the radiographic imaging room. Positioning in a patient room is often performed while supporting both the patient's body and the radiographic imaging cassette. For this reason, it may be difficult to release the hand from the radiographic imaging cassette at the time of positioning. In this state, there is a problem that it is difficult to adjust the direction and position of the radiation emission unit.

The mobile radiographic imaging apparatus described in JP2009-297517A can electrically displace the radiation emission unit, but the operation unit is provided in the apparatus main body. Therefore, in a case where the operator adjusts the direction and position of the radiation emission unit, the operator cannot operate the operation unit unless the operator releases his or her hands from the patient and the radiographic imaging cassette and goes to the location of the mobile radiographic imaging apparatus.

The mobile radiographic imaging apparatus described in JP2011-245271A comprises a handheld device, but the handheld device is present separately from the radiographic imaging cassette. Therefore, at least one hand should be released from the radiographic imaging cassette in order to operate the handheld device. For this reason, it is difficult to operate the handheld device in a state in which both hands are busy, for example, in a state in which the operator supports the patient's body with one hand while supporting the radiographic imaging cassette with the other hand.

It is an object of the technique of the present disclosure to provide a mobile radiographic imaging system and a radiographic imaging cassette capable of adjusting the direction and position of a radiation emission unit without releasing the hand from the radiographic imaging cassette at the time of positioning for radiographic imaging.

In order to achieve the aforementioned object, a mobile radiographic imaging system of the present disclosure is a mobile radiographic imaging system comprising a mobile radiographic imaging apparatus and a radiographic imaging cassette. The mobile radiographic imaging apparatus comprises: a radiation emission unit that emits radiation; a carriage unit in which the radiation emission unit is mounted and which is able to travel; a displacement mechanism that electrically displaces the radiation emission unit; and a displacement mechanism controller that controls an operation of the displacement mechanism. The radiographic imaging cassette comprises: a radiographic image detection unit that detects a radiographic image based on the radiation emitted from the radiation emission unit and transmitted through a subject; a housing in which the radiographic image detection unit is housed; a remote operation unit that is provided in the housing to remotely operate the displacement mechanism; and an operation instruction transmission unit that transmits an operation instruction for operating the displacement mechanism to the displacement mechanism controller in a case where the remote operation unit is operated.

It is preferable that a column erected on the carriage unit and an arm, which has a proximal end provided on the column and a free end that displaceably supports the radiation emission unit, are provided in the carriage unit. It is preferable that the displacement mechanism includes at least one sub-displacement mechanism of a first displacement mechanism that rotates the column around an axis, a second displacement mechanism that changes a position of the radiation emission unit attached to the arm in a vertical direction with respect to the carriage unit, a third displacement mechanism that changes a position of the radiation emission unit attached to the arm in a horizontal direction, which is perpendicular to the vertical direction, with respect to the carriage unit, a fourth displacement mechanism that rotates the radiation emission unit around an axis of the arm, a fifth displacement mechanism that rotates the radiation emission unit around an axis perpendicular to the axis of the arm, or a sixth displacement mechanism that changes the position of the radiation emission unit in the horizontal direction together with the carriage unit by making the carriage unit travel. It is preferable that the operation instruction includes an operation instruction for operating at least one of the plurality of sub-displacement mechanisms.

It is preferable that the remote operation unit comprises a mechanism selection unit that selects one of the plurality of sub-displacement mechanisms to be operated and a displacement amount adjustment unit that operates the sub-displacement mechanism selected by the mechanism selection unit.

It is preferable that the mobile radiographic imaging apparatus comprises a selected mechanism display unit that displays the sub-displacement mechanism selected by the mechanism selection unit.

It is preferable that the mobile radiographic imaging apparatus comprises an apparatus side operation unit for operating the displacement mechanism, the displacement mechanism controller is able to receive both a remote operation instruction, which is the operation instruction from the remote operation unit, and an apparatus side operation instruction from the apparatus side operation unit, and in a case of operating the displacement mechanism based on the remote operation instruction, the displacement mechanism controller lowers an operation speed of the displacement mechanism than in a case of operating the displacement mechanism based on the apparatus side operation instruction.

It is preferable that the radiographic imaging cassette is a wireless electronic cassette having an image detection panel as the radiographic image detection unit that electrically detects the radiographic image based on the radiation and an image transmission unit that wirelessly transmits the radiographic image to the mobile radiographic imaging apparatus and that the operation instruction transmission unit uses a wireless method.

It is preferable that the operation instruction transmission unit and the image transmission unit use the same transmission path.

It is preferable that the operation instruction transmission unit and the image transmission unit use different transmission paths.

It is preferable that the housing has a rectangular front surface that faces the radiation emission unit and receives the radiation, a rectangular back surface on a side opposite to the front surface, and a side surface around the front surface and the back surface and that the remote operation unit is provided on at least one of the front surface or the back surface.

It is preferable to further comprise: a posture detection mechanism that detects a first posture of the radiation emission unit and a second posture of the radiographic imaging cassette; a deriving unit that derives relative posture information regarding a relative posture between the radiation emission unit and the radiographic imaging cassette based on the first posture and the second posture detected by the posture detection mechanism; and a relative posture information display unit that displays the relative posture information derived by the deriving unit.

It is preferable that the displacement mechanism controller continues an operation of the displacement mechanism while the operation instruction is transmitted from the operation instruction transmission unit and stops the operation of the displacement mechanism in a case where transmission of the operation instruction is stopped and that the operation instruction transmission unit continues transmission of the operation instruction while an operation of an operator on the remote operation continues and stops transmission of the operation instruction in a case where the operation is stopped.

It is preferable that the displacement mechanism controller continues an operation of the displacement mechanism until a stop instruction from the operation instruction transmission unit is received after receiving the operation instruction once from the operation instruction transmission unit, monitors whether or not a data link for receiving the stop instruction is established between the operation instruction transmission unit and the displacement mechanism controller until the stop instruction is received after receiving the operation instruction, and stops the operation of the displacement mechanism even though the stop instruction is not received in a case where the data link is disconnected.

It is preferable that the mobile radiographic imaging apparatus has an irradiation conditions reception unit that receives irradiation conditions of the radiation emission unit and that the displacement mechanism controller allows a remote operation from the remote operation unit with respect to the displacement mechanism only until the radiation emission unit ends irradiation based on the received irradiation conditions after the irradiation conditions reception unit receives the irradiation conditions.

It is preferable to further comprise: a posture detection mechanism that detects a first posture of the radiation emission unit and a second posture of the radiographic imaging cassette; and a relative posture determination unit that determines whether or not a relative posture between the radiation emission unit and the radiographic imaging cassette is within an allowable range set in advance based on the first posture and the second posture detected by the posture detection mechanism. It is preferable that the displacement mechanism controller allows a remote operation from the remote operation unit with respect to the displacement mechanism only while the relative posture is within the allowable range.

It is preferable that the displacement mechanism controller prohibits a remote operation from the remote operation unit with respect to the displacement mechanism in any of a case where an irradiation instruction for the radiation emission unit is input, a case where an irradiation detection signal indicating that emission of the radiation has been detected in the radiographic imaging cassette is input, and a case where contact of an operator with the mobile radiographic imaging apparatus is detected.

It is preferable that the mobile radiographic imaging apparatus comprises a lock mechanism that locks at least some of the displacement mechanisms and that, while the operation instruction targeting some of the displacement mechanisms is input, the displacement mechanism controller prohibits a manual operation for at least some of the displacement mechanisms other than the operation target by operating the lock mechanism.

It is preferable that the mobile radiographic imaging apparatus comprises a notification unit that notifies that the displacement mechanism is remotely operated while the displacement mechanism is being operated by a remote operation from the remote operation unit.

It is preferable that the mobile radiographic imaging apparatus comprises an obstacle detection unit that detects whether or not there is an obstacle in a direction in which the radiation emission unit is displaced by an operation of the displacement mechanism.

A radiographic imaging cassette of the present disclosure is a radiographic imaging cassette capable of being used in combination with a mobile radiographic imaging apparatus comprising a carriage unit in which a radiation emission unit is mounted and which is able to travel, a displacement mechanism that electrically displaces the radiation emission unit, and a displacement mechanism controller that controls an operation of the displacement mechanism. The radiographic imaging cassette comprises: a radiographic image detection unit that detects a radiographic image based on radiation emitted from the radiation emission unit and transmitted through a subject; a housing in which the radiographic image detection unit is housed; a remote operation unit that is provided in the housing to remotely operate the displacement mechanism; and an operation instruction transmission unit that transmits an operation instruction for operating the displacement mechanism to the displacement mechanism controller in a case where the remote operation unit is operated.

According to the technique of the present disclosure, it is possible to provide a mobile radiographic imaging system and a radiographic imaging cassette capable of adjusting the direction and position of a radiation emission unit without releasing the hand from the radiographic imaging cassette at the time of positioning for radiographic imaging.

BRIEF DESCRIPTION OF THE DRAWINGS

Exemplary embodiments according to the technique of the present disclosure will be described in detail based on the following figures, wherein:

FIG. 10A is a side view and FIG. 10B is a cross-sectional view;

FIG. 15 is an explanatory diagram of the first posture of the radiation emission unit;

FIG. 17 is an explanatory diagram of the relative posture between the radiation emission unit and the electronic cassette;

FIG. 19A is a side view and FIG. 19B is a cross-sectional view;

DETAILED DESCRIPTION

First Embodiment

Figure 1:
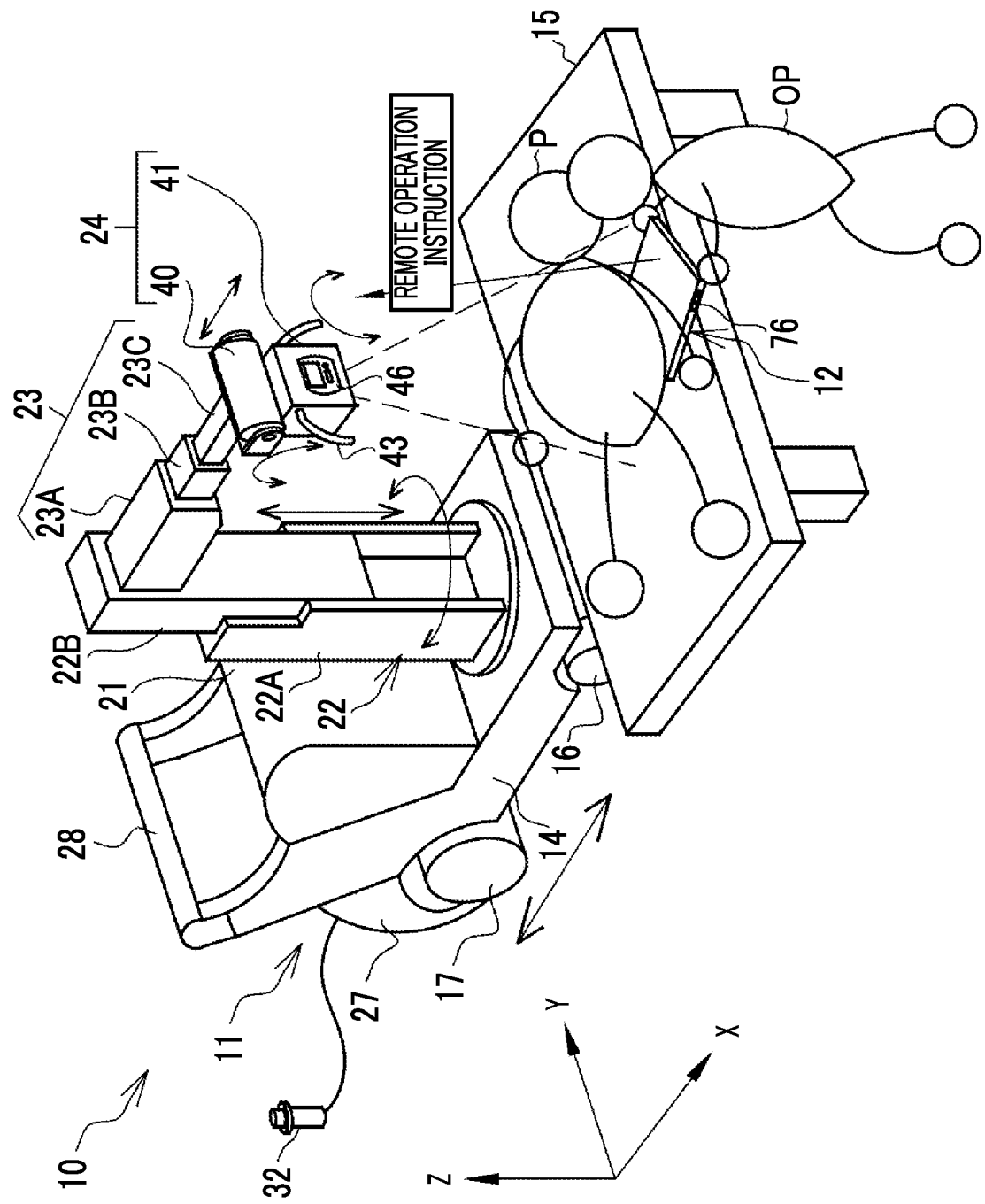
FIG. 1 is a diagram showing a mobile radiographic imaging apparatus.
Figure 2:
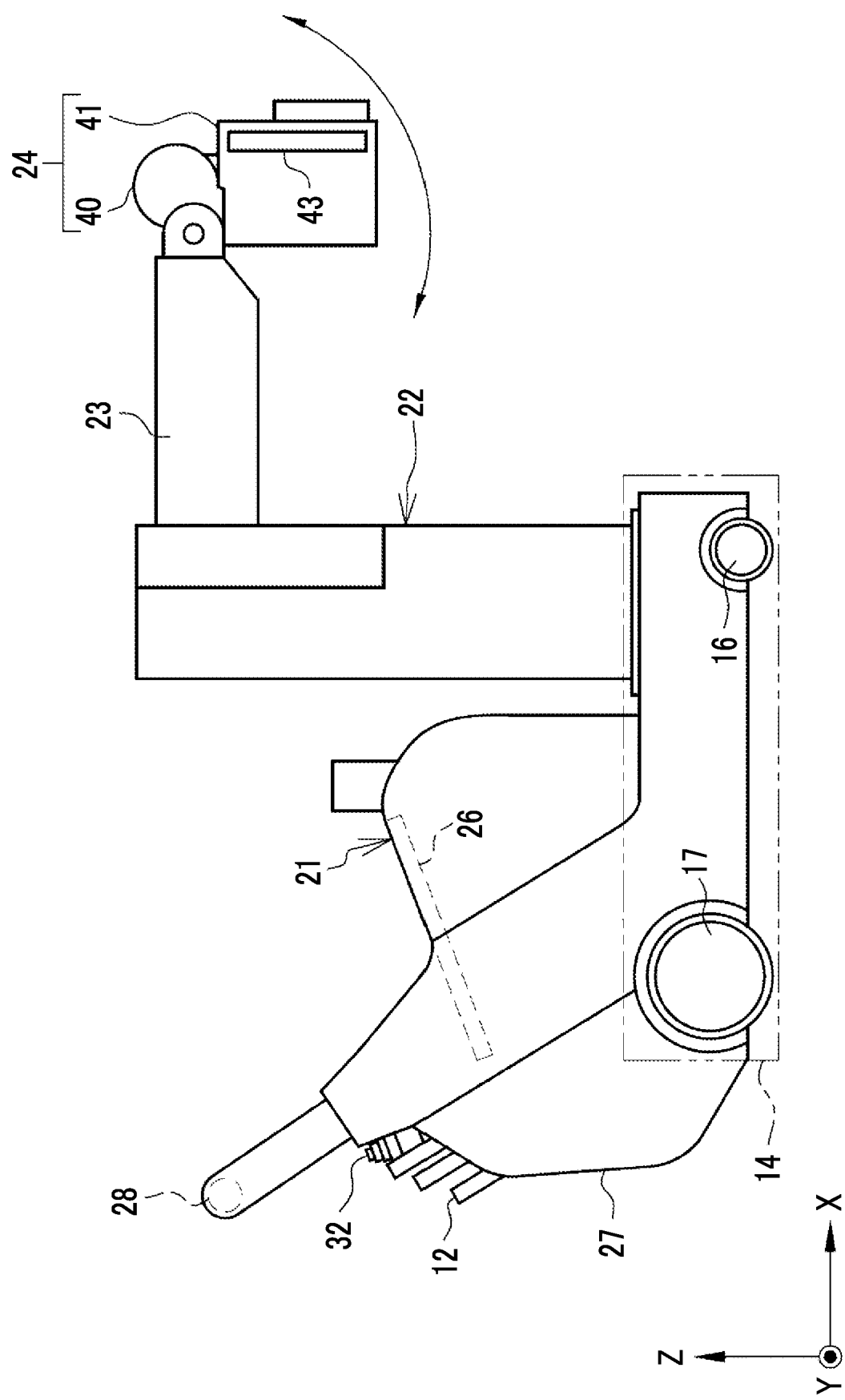
FIG. 2 is a diagram of the mobile radiographic imaging apparatus in a state in which a radiation emission unit is spread out.
Figure 3:
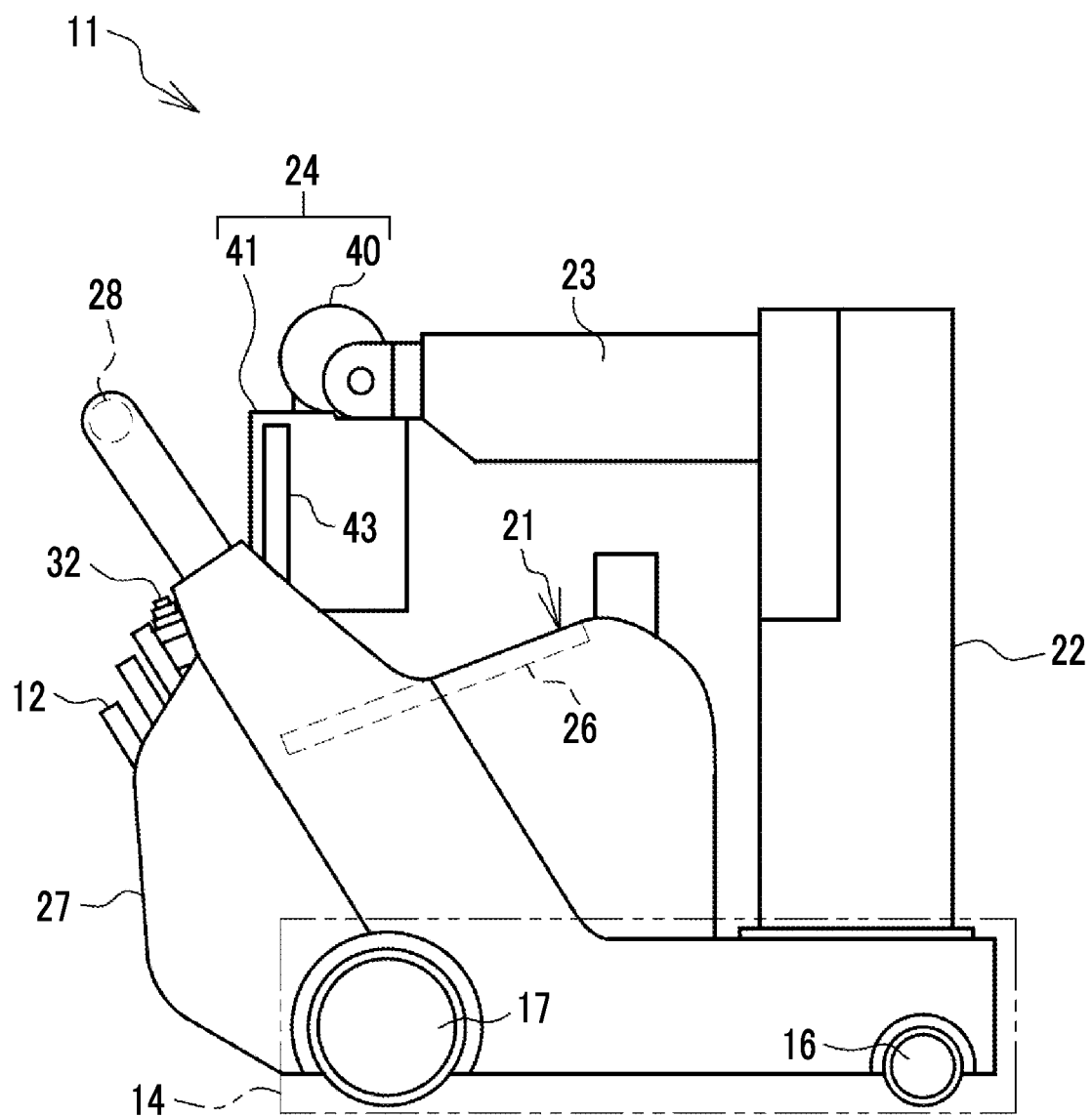
FIG. 3 is a diagram of the mobile radiographic imaging apparatus in a state in which the radiation emission unit is housed.

In FIGS. 1 to 3, a mobile radiographic imaging system 10 comprises a mobile radiographic imaging apparatus 11 and an electronic cassette 12. The electronic cassette 12 is an example of a radiographic imaging cassette according to the technique of the present disclosure.

The mobile radiographic imaging apparatus 11 comprises a carriage unit 14. The carriage unit 14 has four wheels of front wheels 16 and rear wheels 17, and can travel by rotation of the wheels. Here, "can travel" includes at least one of "can travel by manual operation of an operator OP" or "can travel based on electric driving or electric assist". The front wheels 16 revolve around the Z axis shown in FIG. 1, and function as steering wheels for changing the movement direction of the carriage unit 14.

The mobile radiographic imaging apparatus 11 can be moved in a hospital by the carriage unit 14, and is used for so-called round-visit imaging in which radiographic imaging is performed while going around a patient room. For this reason, the mobile radiographic imaging apparatus 11 is also called a round-visit car. The mobile radiographic imaging apparatus 11 is used by being carried into the patient room together with the electronic cassette 12 in order to image a patient P that is difficult to move to the imaging room. The mobile radiographic imaging apparatus 11 is placed beside a bed 15. The electronic cassette 12 is set at a position corresponding to the imaging part of the patient P on the bed 15 on which the patient P is supine. The patient P is an example of a subject. The mobile radiographic imaging apparatus 11 can also be used by being carried into an imaging room or an operating room other than the patient room.

A main body unit 21, a column 22, an arm 23, a radiation emission unit 24, and the like are mounted in the carriage unit 14. The main body unit 21 has a console 26, a cassette housing unit 27, and a handle 28. The console 26 is provided in a form embedded on the inclined upper surface of the main body unit 21. The console 26 is, for example, a tablet computer having a touch panel display. The console 26 is operated by the operator OP at the time of setting the irradiation conditions and the like. The console 26 displays various screens including an irradiation conditions setting screen, a radiographic image, and the like.

The cassette housing unit 27 is disposed on the back surface of the main body unit 21. The electronic cassette 12 is housed in the cassette housing unit 27. A plurality of electronic cassettes 12 can be housed in the cassette housing unit 27.

The handle 28 is provided in a form protruding above the main body unit 21, and is inclined toward the rear of the carriage unit 14. The handle 28 is gripped by the operator OP, such as a radiology technician, in order to steer the carriage unit 14.

As will be described later, the column 22 is attached so as to be rotatable around the Z axis extending in the height direction. The mobile radiographic imaging apparatus 11 is moved in a state shown in FIG. 3 in which the column 22 is rotated such that the radiation emission unit 24 is housed in the upper portion of the main body unit 21.

An irradiation switch 32 is attached to the upper portion of the cassette housing unit 27. The irradiation switch 32 is a switch for the operator OP to give an instruction to start the emission of radiation. A cable is connected to the irradiation switch 32, so that the irradiation switch 32 can be used by being detached from the main body unit 21. The irradiation switch 32 is, for example, a two-stage pressing type switch. The irradiation switch 32 generates a warm-up command signal in a case where the irradiation switch 32 is pressed to the first stage (half-pressed), and generates an irradiation start command signal in a case where the irradiation switch 32 is pressed to the second stage (fully pressed).

Although not shown, a battery for supplying power to each unit is built into the main body unit 21.

The column 22 has, for example, a prismatic shape, and is erected along the Z-axis direction on the carriage unit 14.

A proximal end of the arm 23 is provided on the column 22, and the free end of the arm 23 supports the radiation emission unit 24 so as to be freely displaced. In this example, the arm 23 extends in a horizontal direction with respect to the column 22 whose main part extends in a vertical direction.

The radiation emission unit 24 is configured to include a radiation tube 40 and an irradiation field limiter 41. The radiation tube 40 generates, for example, X-rays as radiation. The radiation tube 40 is, for example, a thermoelectron emission type tube including a filament, a target, and the like (none of these are shown). A tube voltage from a voltage generator 92 (refer to FIG. 12) is applied between the filament serving as a cathode and the target serving as an anode. The filament emits thermoelectrons according to the applied tube voltage toward the target. The target emits radiation by the impact of thermoelectrons from the filament. The flow rate of thermoelectrons from the filament toward the target is called a tube current. The tube voltage and the tube current are set as irradiation conditions together with the irradiation time.

In a case where the irradiation switch 32 is fully pressed to generate an irradiation start command signal, a tube voltage is applied from the voltage generator 92 and radiation is emitted from the radiation tube 40. The emitted radiation is emitted toward the patient P through the irradiation field limiter 41. In a case where the irradiation time set in the irradiation conditions has passed from the start of the emission of radiation, the application of the tube voltage is stopped and the emission of the radiation is ended.

The irradiation field limiter 41 limits the irradiation field of the radiation emitted from the radiation tube 40. The irradiation field limiter 41 has, for example, a configuration in which four shielding plates, such as lead for shielding radiation, are disposed on the sides of a quadrangle and a quadrangular exit opening that transmits radiation is formed in the central portion. The irradiation field limiter 41 changes the size of the exit opening by changing the position of each shielding plate, thereby changing the irradiation field.

The column 22 has a first column 22A and a second column 22B. The first column 22A is provided on the upper surface of the carriage unit 14. The first column 22A can rotate around the axis of the column 22 (around the Z axis) with respect to the carriage unit 14. Due to the rotation of the first column 22A around the axis, the entire column 22 rotates around the axis. The column 22 can expand and contract in the Z-axis direction extending in the vertical direction. That is, the second column 22B can move up and down along the Z-axis direction with respect to the first column 22A.

As described above, since the second column 22B moves in the Z-axis direction with respect to the first column 22A, the length of the column 22 is increased or decreased. By expanding and contracting the column 22, it is possible to change the vertical position of the radiation emission unit 24 with respect to the carriage unit 14.

The arm 23 has a first arm 23A, a second arm 23B, and a third arm 23C. The proximal end of the first arm 23A is attached to the second column 22B. The second arm 23B is attached to the distal end of the first arm 23A. That is, the first arm 23A connects the second column 22B and the second arm 23B to each other. The third arm 23C is attached to the distal end of the second arm 23B. The radiation emission unit 24 is attached to the distal end of the third arm 23C. The arm 23 can expand and contract in the horizontal direction (X-Y plane) perpendicular to the vertical direction. That is, the second arm 23B can move along the horizontal direction with respect to the first arm 23A. Then, the third arm 23C can move along the horizontal direction with respect to the second arm 23B.

As described above, since the second arm 23B and the third arm 23C move in the horizontal direction, the length of the arm 23 is increased or decreased. By expanding and contracting the arm 23, it is possible to change the horizontal position of the radiation emission unit 24 with respect to the carriage unit 14. In addition, since the column 22 can be made to rotate around the Z axis, it is possible to change the horizontal position of the radiation emission unit 24 by the rotation of the column 22.

Figure 4:
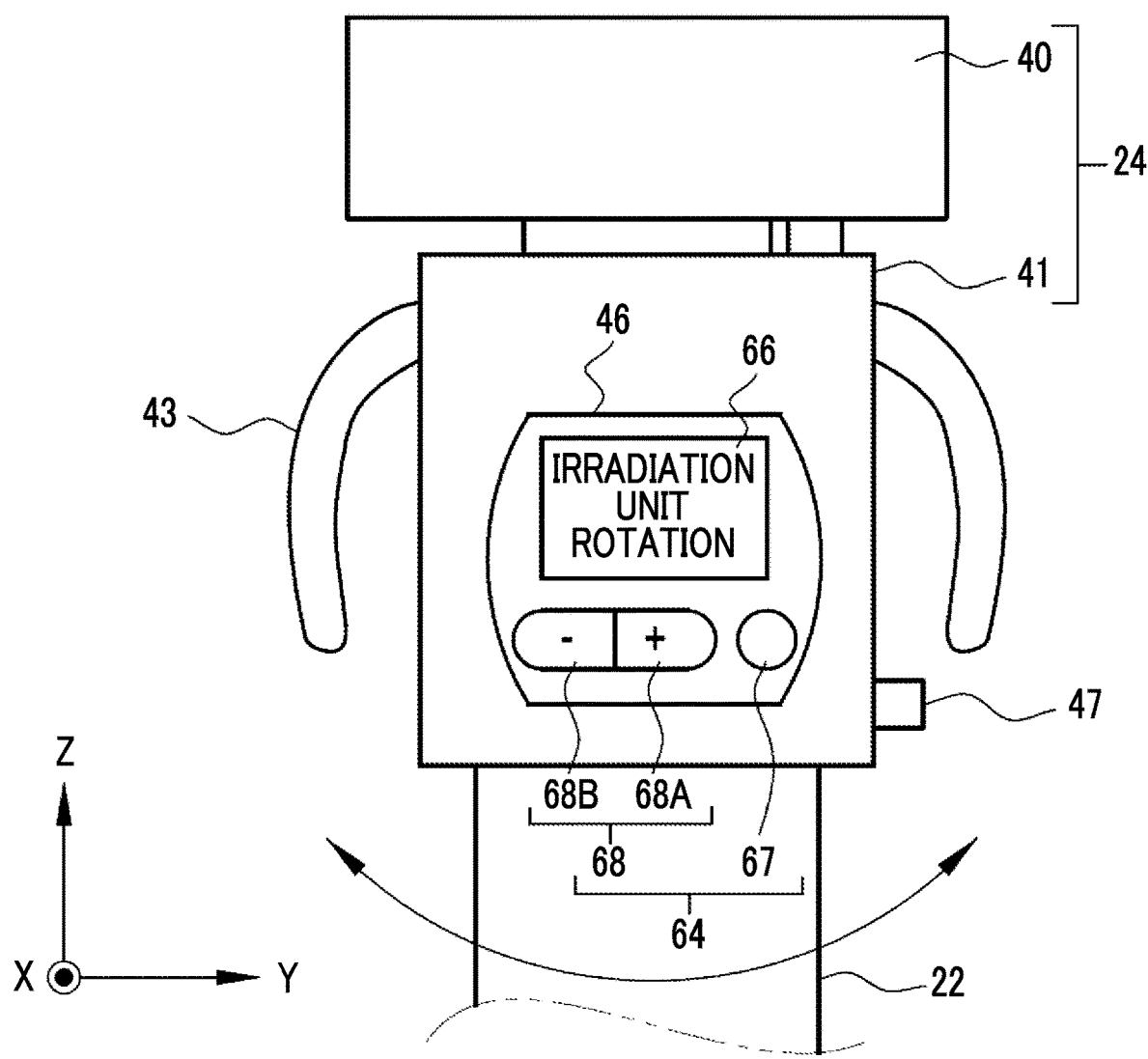
FIG. 4 is a diagram showing the rotation of the radiation emission unit.

As shown in FIG. 4, the radiation emission unit 24 is provided at the free end of the arm 23 so as to be rotatable around the axis of the arm 23, that is, around the X axis in FIGS. 1 to 4. In addition, the radiation emission unit 24 is provided so as to be rotatable around an axis perpendicular to the min 23 and parallel to the width direction of the radiation emission unit 24 (Y axis in FIGS. 1 to 4). Here, in order to distinguish the rotation of the radiation emission unit 24 around the X axis from the rotation of the radiation emission unit 24 around the Y axis, the rotation around the Y axis is referred to as tilt. Thus, by rotating the radiation emission unit 24 around the X axis and tilting the radiation emission unit 24 around the Y axis, it is possible to change the direction (irradiation direction) of the radiation emission unit 24.

A handgrip 43 is provided in the irradiation field limiter 41. The handgrip 43 is gripped by the operator OP in the case of rotating the radiation emission unit 24 around the X axis and tilting the radiation emission unit 24 around the Y axis.

As shown in FIG. 4, the operation panel 46 is provided on the front surface of the irradiation field limiter 41. In the mobile radiographic imaging apparatus 11, as described above, the position and direction of the radiation emission unit 24 can be not only manually changed but also electrically changed. The operation panel 46 is the operation panel 46 for operating a displacement mechanism for electrically changing the position and direction of the radiation emission unit 24. Reference numeral 47 denotes a posture detection sensor that detects the posture of the radiation emission unit 24, and the details thereof will be described later.

Figure 5:
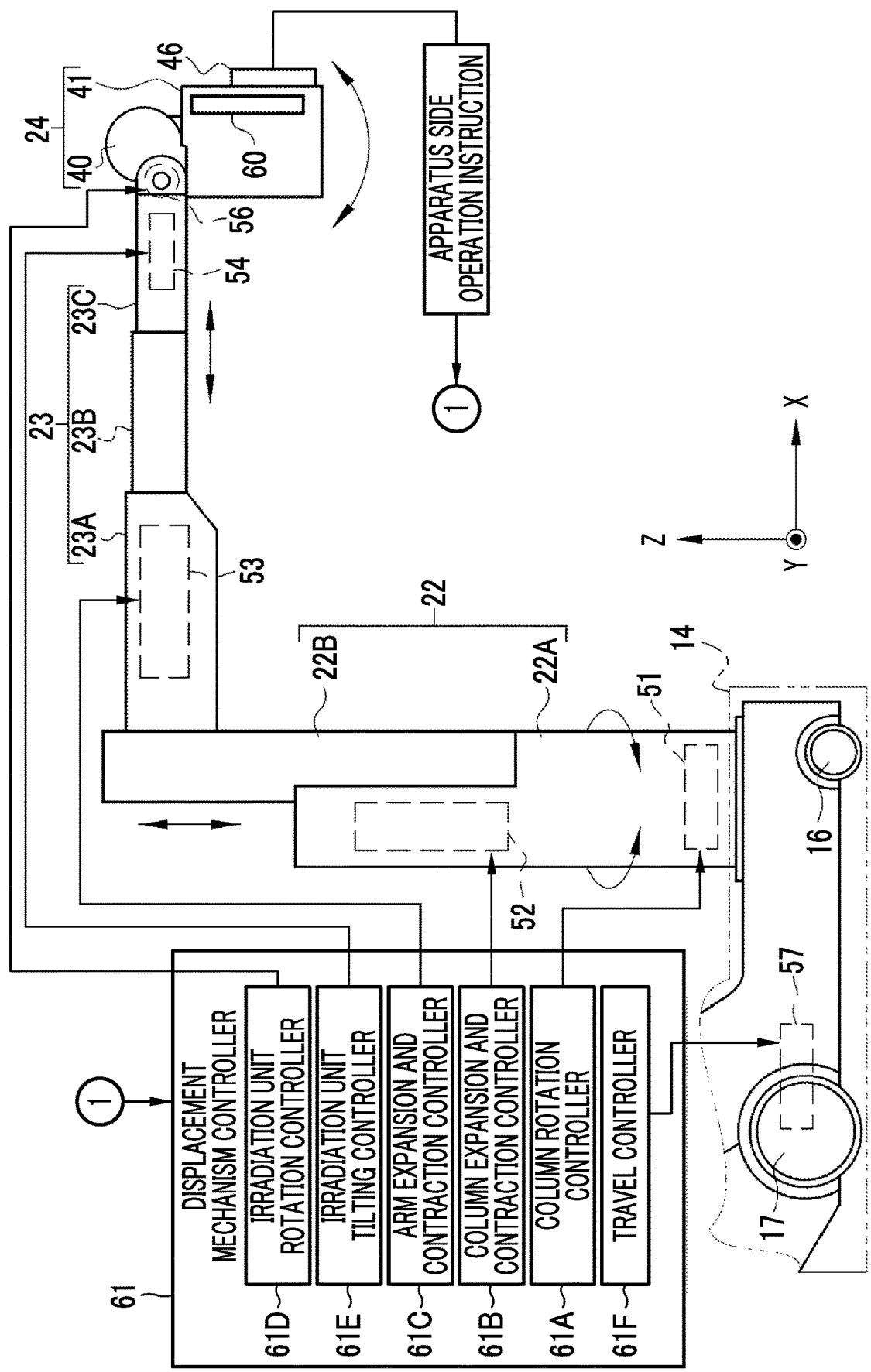
FIG. 5 is an explanatory diagram of a displacement mechanism.

As shown in FIG. 5, the displacement mechanism of the mobile radiographic imaging apparatus 11 has a plurality of sub-displacement mechanisms. In this example, there are six sub-displacement mechanisms including a column rotation mechanism 51, a column expansion and contraction mechanism 52, an arm expansion and contraction mechanism 53, an irradiation unit rotation mechanism 54, an irradiation unit tilting mechanism 56, and a carriage unit traveling mechanism 57.

The column rotation mechanism 51 is a mechanism for rotating the column 22 around the Z axis, and is an example of a first displacement mechanism according to the technique of the present disclosure. The column expansion and contraction mechanism 52 is a mechanism for expanding and contracting the column 22. The column expansion and contraction mechanism 52 changes the vertical position of the radiation emission unit 24 attached to the arm 23 with respect to the carriage unit 14. The column expansion and contraction mechanism 52 is an example of a second displacement mechanism according to the technique of the present disclosure. The arm expansion and contraction mechanism 53 is a mechanism for expanding and contracting the arm 23. The arm expansion and contraction mechanism 53 changes the horizontal position of the radiation emission unit 24 attached to the arm 23 with respect to the carriage unit 14. The arm expansion and contraction mechanism 53 is an example of a third displacement mechanism according to the technique of the present disclosure.

The irradiation unit rotation mechanism 54 is a mechanism for rotating the radiation emission unit 24 around the axis of the arm 23 (around the X axis in FIG. 5). The irradiation unit rotation mechanism 54 is an example of a fourth displacement mechanism according to the technique of the present disclosure. The irradiation unit tilting mechanism 56 is a mechanism for tilting the radiation emission unit 24 around an axis perpendicular to the axis of the arm 23 (around the Y axis in FIG. 5). The irradiation unit tilting mechanism 56 is an example of a fifth displacement mechanism according to the technique of the present disclosure. The carriage unit traveling mechanism 57 is a mechanism for rotating the rear wheel 17 of the carriage unit 14 so that the carriage unit 14 travels. By making the carriage unit 14 travel, the carriage unit traveling mechanism 57 changes the horizontal position of the radiation emission unit 24 together with the carriage unit 14. The carriage unit traveling mechanism 57 is an example of a sixth displacement mechanism according to the technique of the present disclosure.

Each of the sub-displacement mechanisms includes, for example, various electric actuators, such as a motor and a solenoid, and a driving force transmission mechanism (such as a gear and a link mechanism) for transmitting the driving force of the electric actuator to a displacement target.

A displacement mechanism controller 61 receives an operation instruction from the operation panel 46, and controls the driving of each sub-displacement mechanism. The displacement mechanism controller 61 comprises a column rotation controller 61A, a column expansion and contraction controller 61B, an arm expansion and contraction controller 61C, an irradiation unit rotation controller 61D, an irradiation unit tilting controller 61E, and a travel controller 61F. The column rotation controller 61A controls the driving of the column rotation mechanism 51. The column expansion and contraction controller 61B controls the driving of the column expansion and contraction mechanism 52. The arm expansion and contraction controller 61C controls the driving of the arm expansion and contraction mechanism 53. The irradiation unit rotation controller 61D controls the driving of the irradiation unit rotation mechanism 54. The irradiation unit tilting controller 61E controls the driving of the irradiation unit tilting mechanism 56. The travel controller 61F controls the driving of the carriage unit traveling mechanism 57.

In FIG. 4, the operation panel 46 comprises an apparatus side operation unit 64 and an indicator 66. The apparatus side operation unit 64 comprises a mechanism selection button 67 and a displacement amount adjustment button 68. The mechanism selection button 67 is an operation unit for selecting a sub-displacement mechanism to be operated among the six sub-displacement mechanisms. The displacement amount adjustment button 68 is an operation unit for operating the sub-displacement mechanism selected by the mechanism selection button 67. The displacement amount adjustment button 68 includes, for example, a plus button 68A and a minus button 68B.

The indicator 66 displays the sub-displacement mechanism selected by the mechanism selection button 67. The indicator 66 is, for example, a liquid crystal display (LCD). In FIG. 4, the indicator 66 is displayed as "irradiation unit rotation", and this means that the irradiation unit rotation mechanism 54 is selected as an operation target. Thus, the indicator 66 displays the name or abbreviation of the selected sub-displacement mechanism. The indicator 66 is an example of a selected mechanism display unit according to the technique of the present disclosure.

Figure 6:
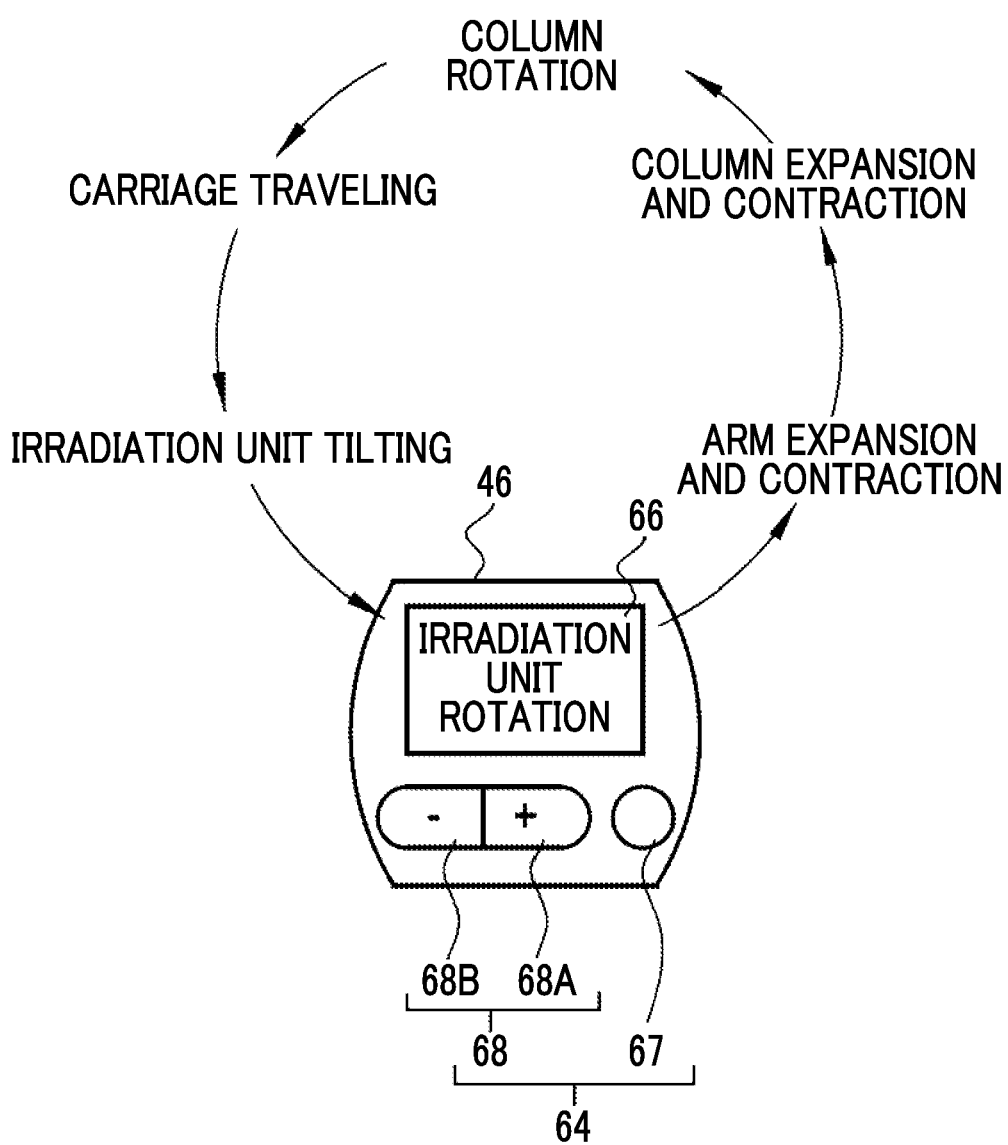
FIG. 6 is a diagram of an indicator showing a selected displacement mechanism.

As shown in FIG. 6, each time the mechanism selection button 67 is pressed once, the six sub-displacement mechanisms are cyclically switched. As shown as an example in FIG. 6, switching occurs in order of the irradiation unit rotation mechanism 54 indicated by "irradiation unit rotation", the irradiation unit tilting mechanism 56 indicated by "irradiation unit tilting", the carriage unit traveling mechanism 57 indicated by "carriage traveling", the column rotation mechanism 51 indicated by "column rotation", the column expansion and contraction mechanism 52 indicated by "column expansion and contraction", and the arm expansion and contraction mechanism 53 indicated by "arm expansion and contraction".

In a case where either the plus button 68A or the minus button 68B of the displacement amount adjustment button 68 is pressed in a state in which a sub-displacement mechanism to be operated is selected by the mechanism selection button 67, the selected sub-displacement mechanism operates. For example, in a case where the plus button 68A is pressed in a state in which the irradiation unit rotation mechanism 54 is selected, an operation instruction is input to the irradiation unit rotation controller 61D. In a case where the operation instruction is received, the irradiation unit rotation controller 61D controls the driving of the irradiation unit rotation mechanism 54 to rotate the radiation emission unit 24 clockwise around the axis of the arm 23. In a case where the minus button 68B is pressed, the irradiation unit rotation controller 61D rotates the radiation emission unit 24 counterclockwise around the axis of the arm 23. Here, in order to distinguish an operation instruction input from the apparatus side operation unit 64 from an operation instruction input from the electronic cassette 12 to be described later, operation instruction input from the apparatus side operation unit 64 is referred to as an apparatus side operation instruction.

Figure 7:
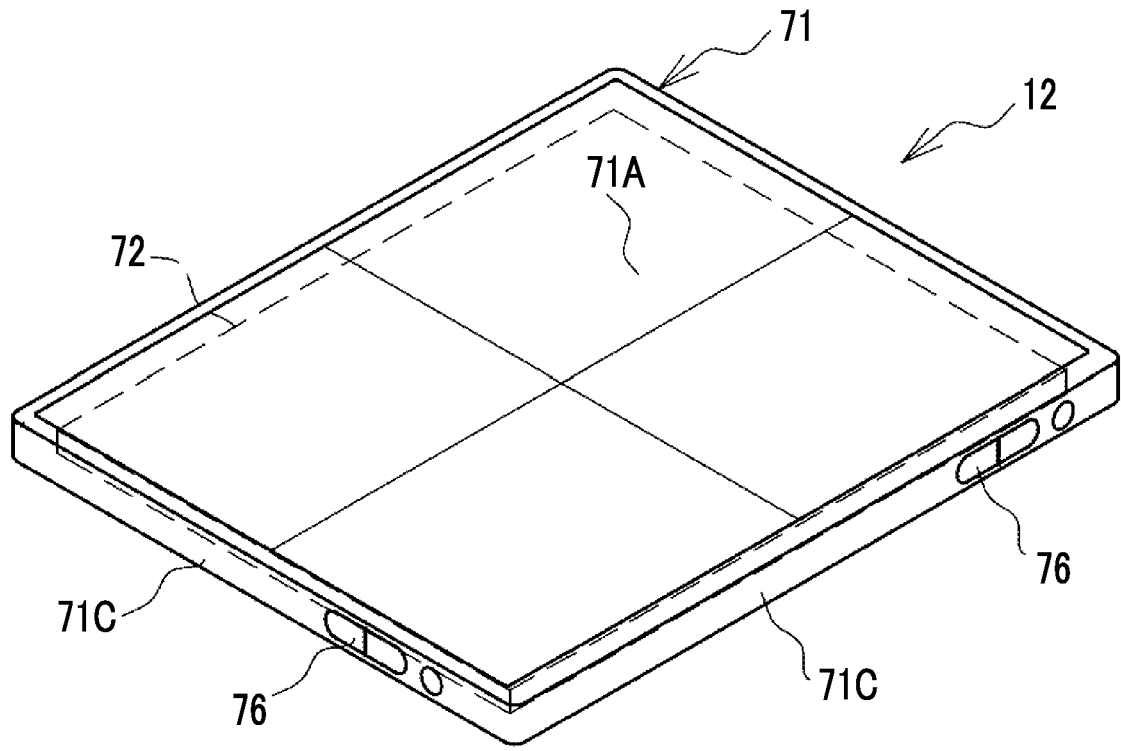
FIG. 7 is a perspective view of an electronic cassette.
Figure 8:
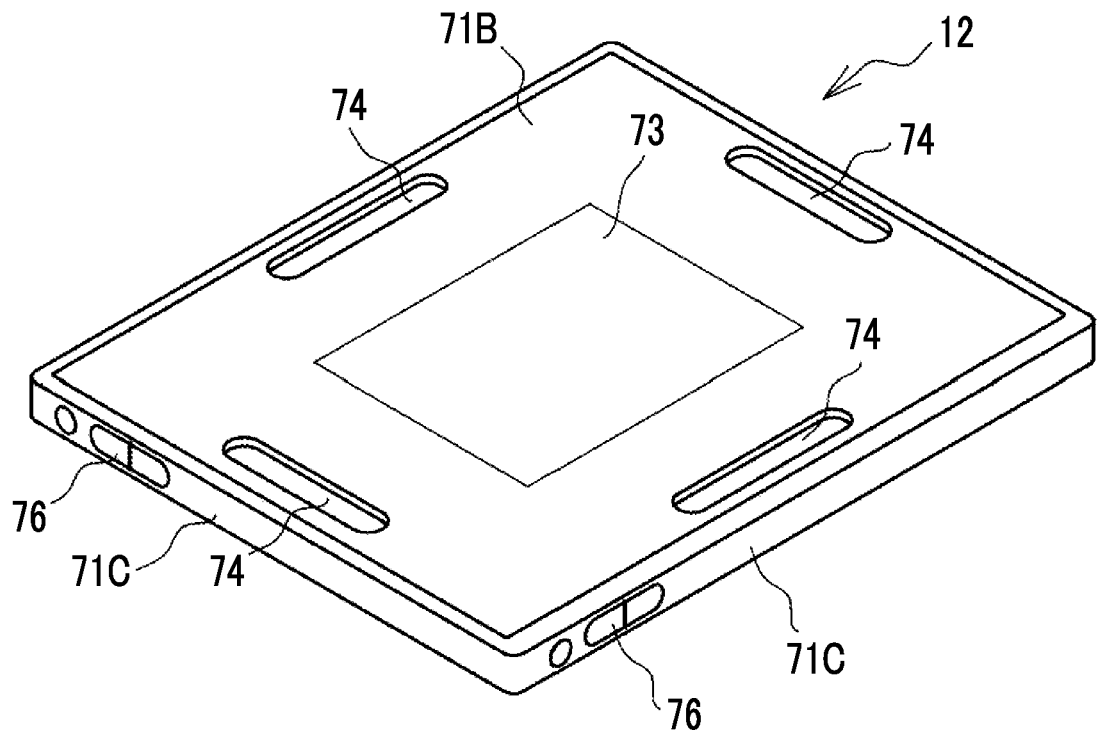
FIG. 8 is a perspective view of a back surface side of the electronic cassette.

As shown in FIGS. 7 and 8, the electronic cassette 12 comprises an image detection panel 72 and a housing 71 in which the image detection panel 72 is housed. As is well known, the image detection panel 72 electrically detects a radiographic image based on radiation transmitted through the subject. The image detection panel 72 has a detection surface on which pixels are arranged in a two-dimensional manner. The image detection panel 72 may be an indirect conversion type panel or may be a direct conversion type panel. The indirect conversion type panel has a scintillator, so that radiation is once converted into visible light by the scintillator and the converted visible light is photoelectrically converted. The direct conversion type panel converts radiation directly into an electrical signal. The image detection panel 72 is an example of a radiographic image detection unit. There are a plurality of types of electronic cassettes 12 having vertical and horizontal sizes of, for example, 17 inches×17 inches, 17 inches×14 inches, 12 inches×10 inches, and the like.

The housing 71 has a flat rectangular parallelepiped shape whose planar shape is an approximately rectangular shape. The housing 71 has a rectangular front surface 71A for receiving radiation, a rectangular back surface 71B opposite to the front surface 71A, and a side surface 71C around the front surface 71A and the back surface 71B. Four side surfaces 71C are provided corresponding to the sides of the front surface 71A and the back surface 71B.

As shown in FIG. 8, a detachable battery 73 is provided on the back surface 71B of the housing 71. The electronic cassette 12 is a wireless electronic cassette that can wirelessly transmit a radiographic image to the mobile radiographic imaging apparatus 11.

On the back surface 71B of the housing 71, a finger hanging portion 74 is provided along each side. As shown in FIG. 1, at the time of imaging, the electronic cassette 12 is disposed between the patient P and the bed 15. The finger hanging portion 74 is used to hang the finger of the operator OP, for example, at the time of pulling out the electronic cassette 12 from the gap between the patient P and the bed 15 and at the time of moving the position of the electronic cassette 12 disposed at the gap.

A remote operation unit 76 is provided on each side surface 71C of the housing 71. The remote operation unit 76 is an operation unit for remotely operating the displacement mechanism of the mobile radiographic imaging apparatus 11. That is, in the mobile radiographic imaging system 10, the electronic cassette 12 can function as a remote controller for changing the direction and position of the radiation emission unit 24.

Figure 9:
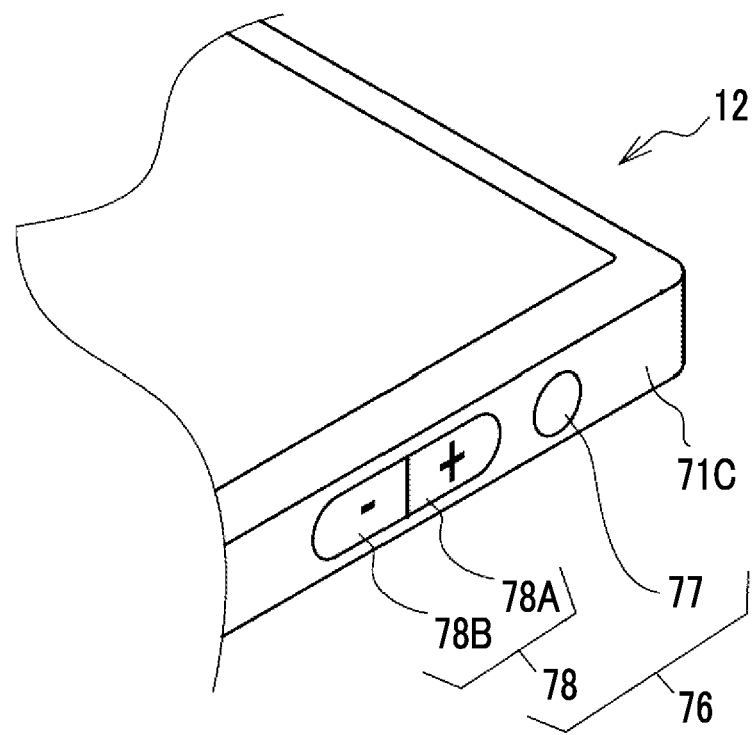
FIG. 9 is a diagram of a remote operation unit.

As shown in FIG. 9, the remote operation unit 76 comprises a mechanism selection button 77 and a displacement amount adjustment button 78 in the same manner as the apparatus side operation unit 64 shown in FIG. 4. The functions of the mechanism selection button 77 and the displacement amount adjustment button 78 are the same as those of the mechanism selection button 67 and the displacement amount adjustment button 68 of the apparatus side operation unit 64. The mechanism selection button 77 and the displacement amount adjustment button 78 are examples of a mechanism selection unit and a displacement amount adjustment unit according to the technique of the present disclosure. The display of an indicator 66 is also switched by operating the mechanism selection button 67 of the remote operation unit 76. The indicator 66 is an example of a selected mechanism display unit that displays a sub-displacement mechanism selected by the mechanism selection button 67 according to the technique of the present disclosure.

Figures 10A, 10B:
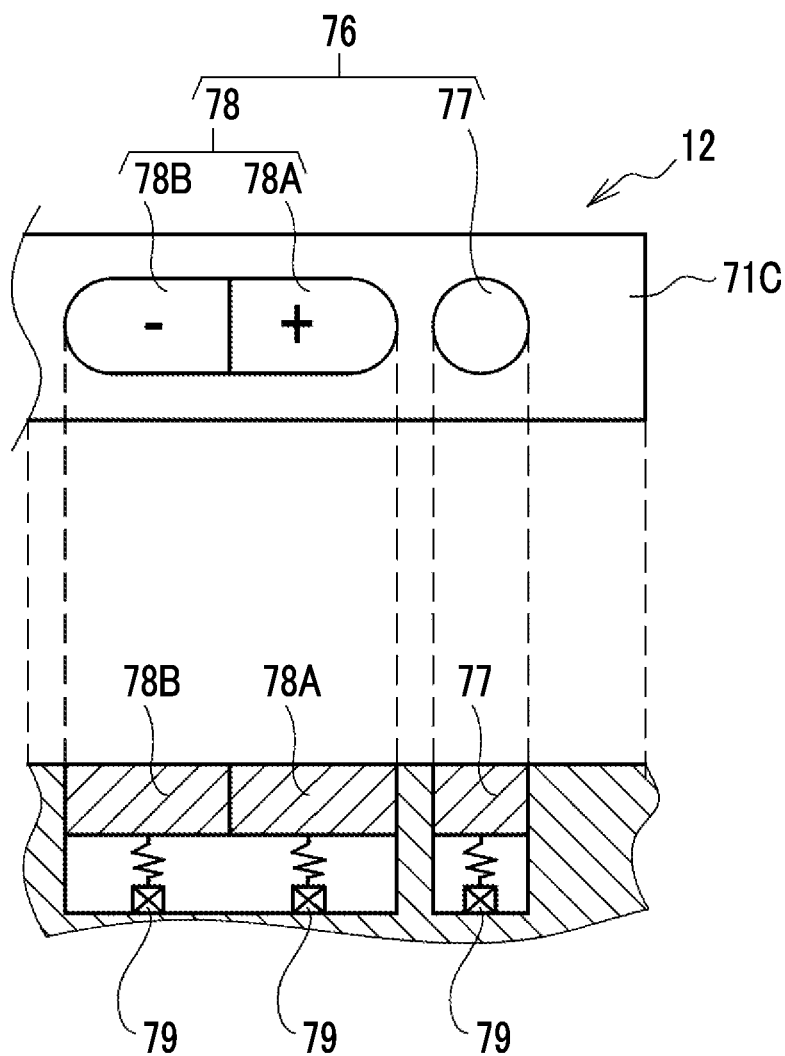
FIGS. 10A and 10B are explanatory diagrams of the remote operation unit, where

As shown as an example in FIGS. 10A and 10B, the mechanism selection button 77 and the displacement amount adjustment button 78 are push buttons. FIG. 10A is a plan view of the remote operation unit 76 disposed on the side surface 71C. As shown in the cross-sectional view of FIG. 10B, a microswitch 79 is provided corresponding to each of the mechanism selection button 77 and the displacement amount adjustment button 78. The mechanism selection button 77 and the displacement amount adjustment button 78 are biased toward the side surface 71C by a spring provided between the microswitch 79 and each of the mechanism selection button 77 and the displacement amount adjustment button 78.

Figure 11:
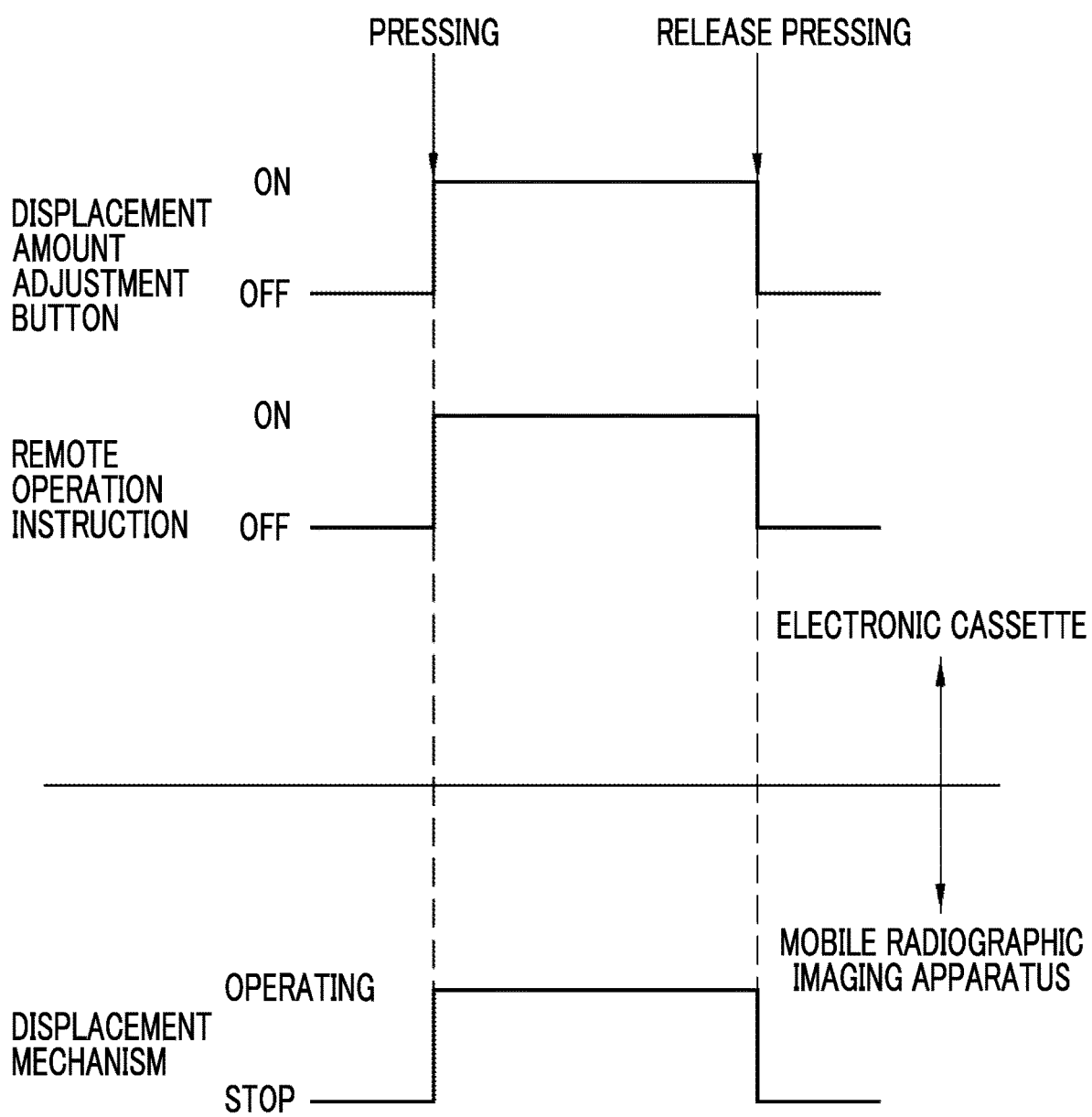
FIG. 11 is a diagram showing the output form of a signal of a remote operation instruction.

As shown in FIG. 11, the microswitch 79 provided corresponding to each of the plus button 78A and the minus button 78B of the displacement amount adjustment button 78 continues to output a signal while being turned on. Therefore, in a case where the displacement amount adjustment button 78 is pressed, the microswitch 79 is turned on to output (ON) an operation instruction. Then, the microswitch 79 continues to output the operation instruction until the pressing of the displacement amount adjustment button 78 is released. Here, in order to distinguish an operation instruction output by the operation of the remote operation unit 76 from an apparatus side operation instruction output by the operation of the apparatus side operation unit 64, the operation instruction output by the operation of the remote operation unit 76 is referred to as a remote operation instruction.

Figure 12:
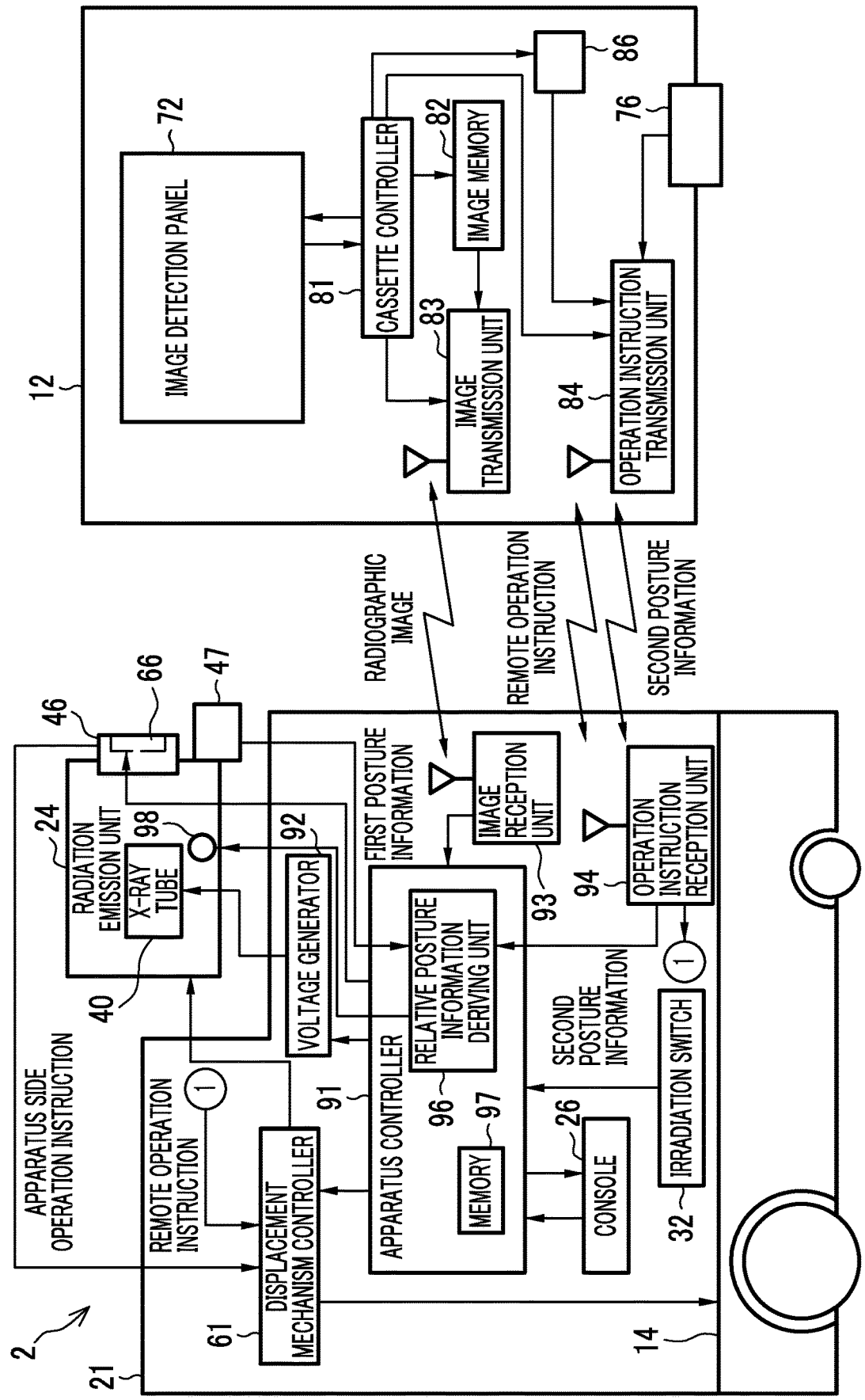
FIG. 12 is a block diagram showing the electric configuration of a mobile radiographic imaging system.

The remote operation instruction is transmitted to the displacement mechanism controller 61 of the mobile radiographic imaging apparatus 11 by an operation instruction transmission unit 84 shown in FIG. 12. The operation instruction transmission unit 84 continues to transmit the remote operation instruction while an operation of the operator OP with respect to the remote operation unit 76 is continued, and stops the transmission of the remote operation instruction in a case where the operation is stopped.

Therefore, the displacement mechanism controller 61 continues the operation of the displacement mechanism while the remote operation instruction is transmitted by the operation of pressing the displacement amount adjustment button 78. Then, in a case where the transmission of the remote operation instruction is stopped by releasing the pressing of the displacement amount adjustment button 78, the operation of the displacement mechanism is stopped.

As shown in FIG. 12, the electronic cassette 12 comprises a cassette controller 81, an image memory 82, an image transmission unit 83, the operation instruction transmission unit 84, and a posture detection sensor 86 in addition to the image detection panel 72 and the remote operation unit 76. The cassette controller 81 performs overall control of the respective units of the image detection panel 72, such as the electronic cassette 12. In addition, the electronic cassette 12 has an irradiation detection function for detecting that radiation has been emitted. The cassette controller 81 monitors an output signal, which is output according to the incident radiation by the image detection panel 72, to detect the start and end of radiation emission.

The image memory 82 stores a radiographic image detected by the image detection panel 72. The image transmission unit 83 transmits the radiographic image stored in the image memory 82 to the mobile radiographic imaging apparatus 11. The operation instruction transmission unit 84 transmits the remote operation instruction, which is output by the operation of the remote operation unit 76, to the mobile radiographic imaging apparatus 11.

The image transmission unit 83 is a wireless communication unit that uses a wireless method. The image transmission unit 83 is, for example, a communication interface based on a wireless local area network (LAN) standard of the institute of electrical and electronics engineers, inc. (IEEE) 802.11.

The operation instruction transmission unit 84 is also a wireless communication unit that uses a wireless method. The operation instruction transmission unit 84 is, for example, a short-range wireless communication interface based on the Bluetooth (registered trademark) standard. Thus, in the electronic cassette 12, the image transmission unit 83 and the operation instruction transmission unit 84 use different transmission paths.

The posture detection sensor 86 detects the posture of the electronic cassette 12. The posture detection sensor 86 is, for example, a nine-axis motion sensor in which an acceleration sensor, a gyro sensor (angular rate sensor), and a geomagnetic sensor are combined. The posture detection sensor 86 detects the posture of the electronic cassette 12 in the three-dimensional space of the X axis, the Y axis, and the Z axis, specifically, a posture indicating which direction the front surface 71A of the electronic cassette 12 faces in the three-dimensional space. Here, in order to distinguish from the posture of the radiation emission unit 24 to be described later, the posture of the radiation emission unit 24 is referred to as a first posture, and the posture of the electronic cassette 12 is referred to as a second posture.

Second posture information indicating the second posture of the electronic cassette 12 is transmitted to the mobile radiographic imaging apparatus 11 through the operation instruction transmission unit 84, for example.

The mobile radiographic imaging apparatus 11 comprises an apparatus controller 91, the voltage generator 92, an image reception unit 93, an operation instruction reception unit 94, and a posture detection sensor 47 in addition to the radiation emission unit 24, the console 26, the irradiation switch 32, and the displacement mechanism controller 61. The voltage generator 92 generates a tube voltage applied to the radiation tube 40 as described above. The apparatus controller 91 controls each unit of the mobile radiographic imaging apparatus 11.

The image reception unit 93 receives the radiographic image transmitted from the image transmission unit 83 by communicating with the image transmission unit 83. The image reception unit 93 is a communication interface based on the same wireless LAN standard as in the case of the image transmission unit 83. The operation instruction reception unit 94 receives the remote operation instruction and the second posture information transmitted from the operation instruction transmission unit 84 by communicating with the operation instruction transmission unit 84. The operation instruction reception unit 94 is the same short-range wireless communication interface as in the case of the operation instruction transmission unit 84.

The posture detection sensor 47 detects a first posture that is the posture of the radiation emission unit 24. The posture detection sensor 47 is the same nine-axis motion sensor as the posture detection sensor 86. The posture detection sensor 47 detects the first posture of the radiation emission unit 24 in the three-dimensional space of the X axis, the Y axis, and the Z axis, specifically, a first posture indicating the irradiation direction of the radiation emission unit 24 in the three-dimensional space. The posture detection sensor 47 outputs first posture information indicating the first posture to the apparatus controller 91. The posture detection sensor 47 and the posture detection sensor 86 form a posture detection mechanism according to the technique of the present disclosure.

A relative posture information deriving unit 96 is provided in the apparatus controller 91. The relative posture information deriving unit 96 derives relative posture information regarding the relative posture between the radiation emission unit 24 and the electronic cassette 12 based on the first posture and the second posture detected by the posture detection mechanism. The relative posture information deriving unit 96 is an example of a deriving unit according to the technique of the present disclosure.

The apparatus controller 91 determines whether or not the relative posture between the radiation emission unit 24 and the electronic cassette 12 is within an appropriate range based on the relative posture information derived by the relative posture information deriving unit 96. In the apparatus controller 91, information of the appropriate range is stored in a memory 97. Then, in a case where the relative posture between the radiation emission unit 24 and the electronic cassette 12 is within the appropriate range, notification that the relative posture is within the appropriate range is provided by changing the brightness of an irradiation field lamp 98 in the radiation emission unit 24.

Figure 13:
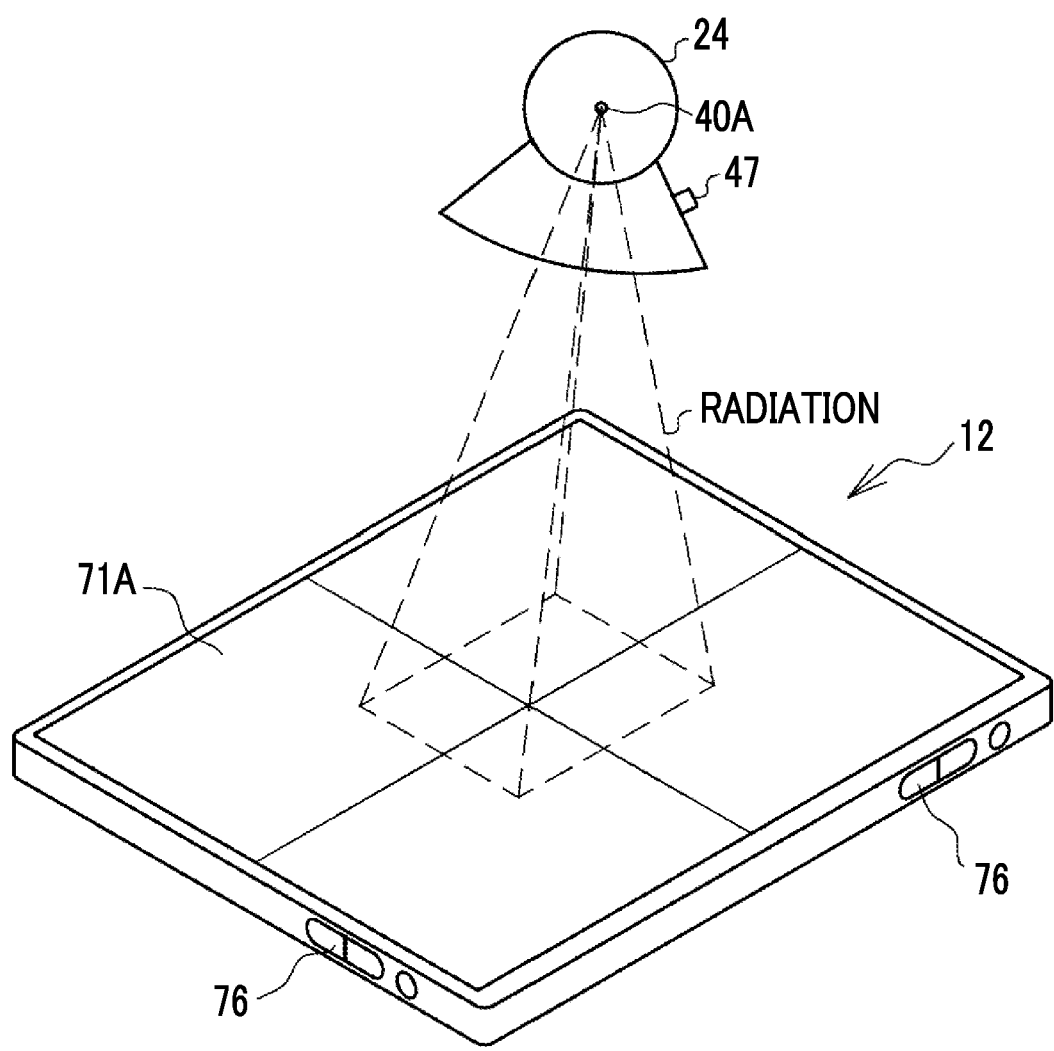
FIG. 13 is a diagram showing the opposite postures of the radiation emission unit and the electronic cassette.

Specifically, as shown in FIG. 13, at the time of imaging, the relative posture is adjusted such that the irradiation direction of the radiation emission unit 24 faces the front surface 71A of the electronic cassette 12. Positioning in radiographic imaging refers to positioning work for adjusting the relative positional relationship between the electronic cassette 12 and the imaging part of the patient P, which is a subject, and positioning work for adjusting the relative positional relationship between the electronic cassette 12 and the radiation emission unit 24.

Figure 14:
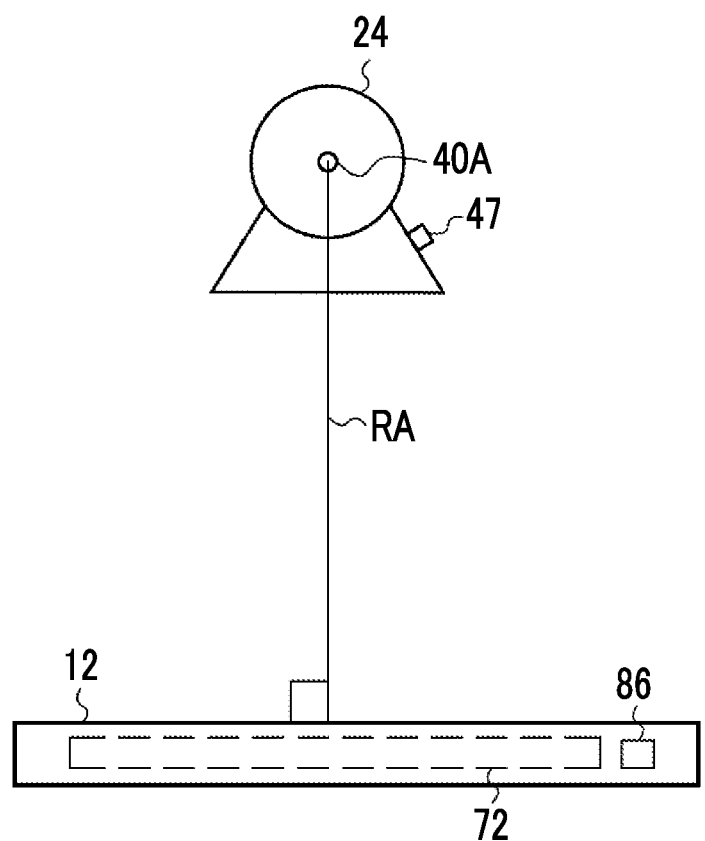
FIG. 14 is a diagram showing an appropriate range of the relative posture between the radiation emission unit and the electronic cassette.

As shown in FIG. 14, the appropriate positional relationship between the radiation emission unit 24 and the electronic cassette 12 is a state in which the incidence axis RA of radiation emitted from the radiation emission unit 24 is disposed so as to be perpendicular to the front surface 71A of the electronic cassette 12. The incidence axis RA is the central axis of a radiation flux emitted from the radiation emission unit 24. Reference numeral 40A denotes a focal point of an X-ray tube 40.

As shown in FIG. 15, for example, as the first posture in the three-dimensional space of the radiation emission unit 24, an inclination $\theta 1$ of the incidence axis RA of the radiation emission unit 24 with respect to a gravity direction G is detected by the posture detection sensor 47.

Figure 16:
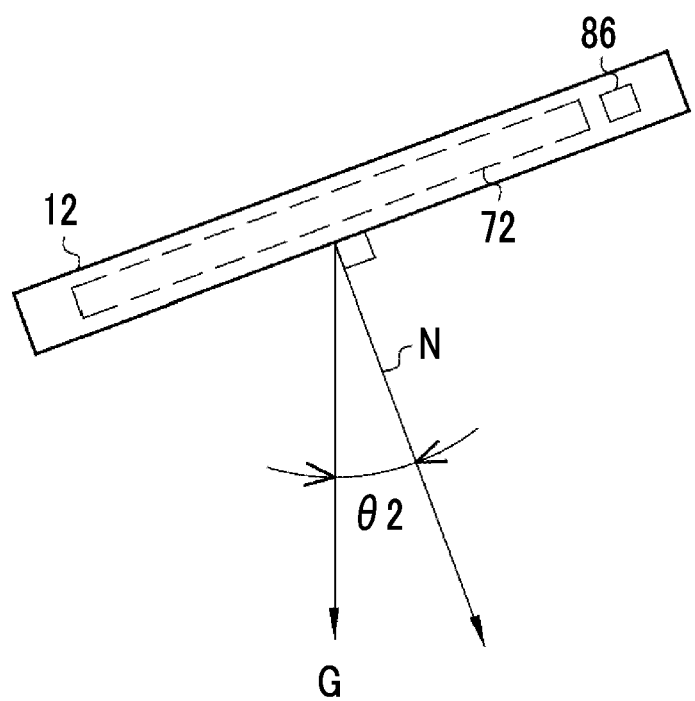
FIG. 16 is an explanatory diagram of the second posture of the electronic cassette.

On the other hand, as shown in FIG. 16, for example, as the second posture in the three-dimensional space of the electronic cassette 12, an inclination $\theta 2$ between a normal N of the front surface 71A and the back surface 71B of the electronic cassette 12 and the gravity direction G is detected by the posture detection sensor 86.

As shown in FIG. 17, based on the inclination $\theta 1$ that is the first posture of the radiation emission unit 24 and the inclination $\theta 2$ that is the second posture of the electronic cassette 12, the relative posture information deriving unit 96 derives an angle $\theta 12$ formed by the normal N and the incidence axis RA as a relative posture between the radiation emission unit 24 and the electronic cassette 12, for example.

Figure 18:
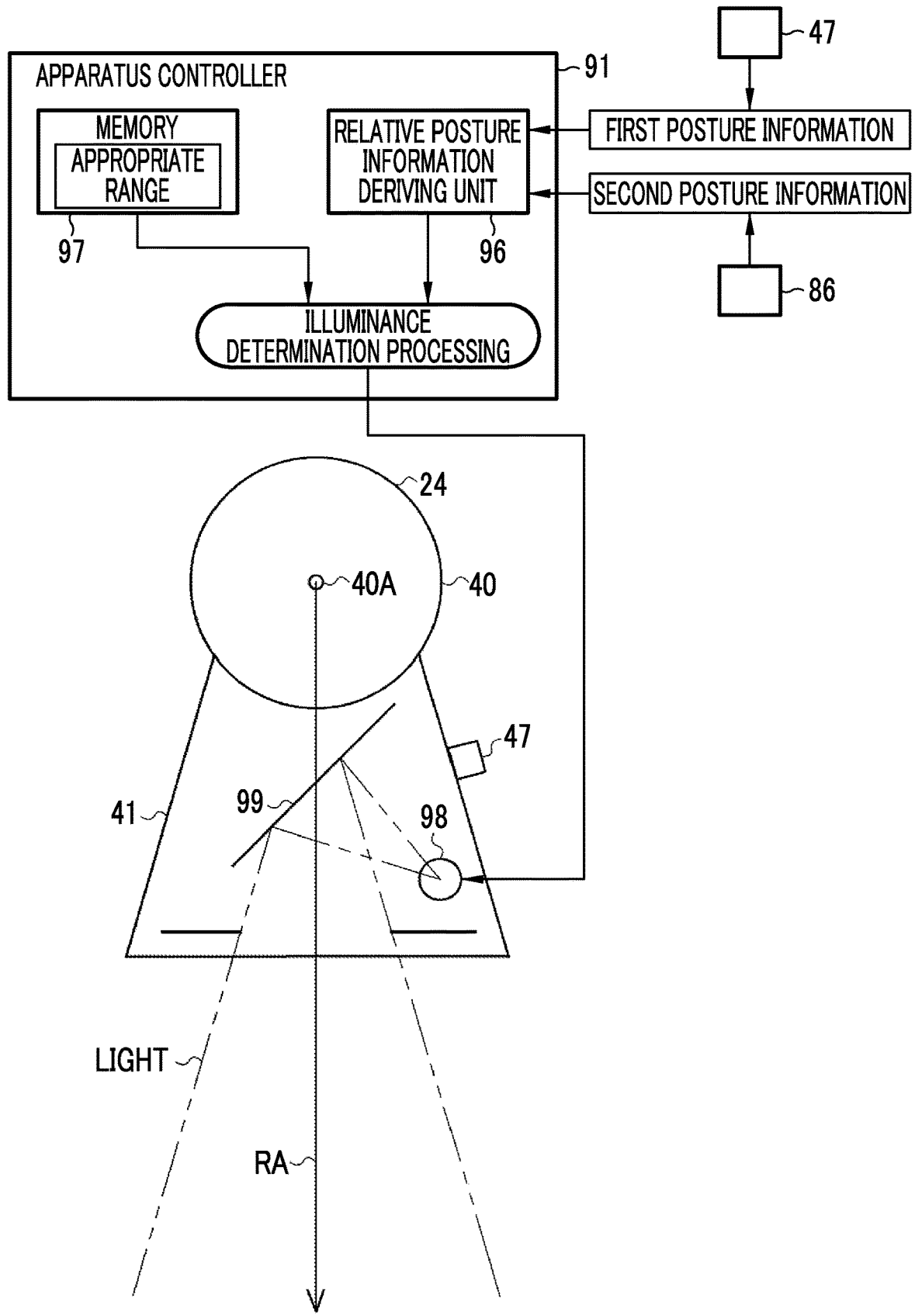
FIG. 18 is an explanatory diagram of an example in which notification that the relative posture between the radiation emission unit and the electronic cassette falls within the appropriate range is provided by using an irradiation field lamp.

As shown in FIG. 18, the apparatus controller 91 compares the angle $\theta 12$ derived by the relative posture information deriving unit 96 with the appropriate range in the memory 97, and executes illuminance determination processing for determining the illuminance of the irradiation field lamp 98 according to whether or not the angle $\theta 12$ is within the appropriate range. The appropriate range is, for example, a range of about $\pm 10°$ with a position where the angle $\theta 12$ shown in FIG. 14 is $0°$ as a reference.

For the sake of convenience, the inclinations $\theta 1$ and $\theta 2$ and the angle $\theta 12$ shown in FIGS. 14 to 17 are shown as inclinations and an angle within the XZ plane. In practice, however, the inclinations $\theta 1$ and $\theta 2$ and the angle $\theta 12$ shown in FIGS. 14 to 17 are inclinations and an angle in a three-dimensional space.

The radiation emission unit 24 comprises the irradiation field lamp 98 and a mirror 99 that reflects light emitted from the irradiation field lamp 98 toward an exit opening defined by the irradiation field limiter 41. The light from the irradiation field lamp 98 is projected onto the body of the patient P who is a subject. The apparatus controller 91 relatively increases the illuminance of the irradiation field lamp 98 in a case where the angle $\theta 12$ is within the appropriate range, and relatively reduces the illuminance in a case where the angle $\theta 12$ is outside the appropriate range. By such a brightness change of the irradiation field lamp 98, the operator OP can grasp whether or not the relative posture between the radiation emission unit 24 and the electronic cassette 12 is within the appropriate range. Whether or not the relative posture between the radiation emission unit 24 and the electronic cassette 12 is within the appropriate range is an example of relative posture information, and the irradiation field lamp 98 corresponds to a relative posture information display unit according to the technique of the present disclosure.

Hereinafter, the operation of the above configuration will be described. In the case of imaging the patient P in a patient room using the mobile radiographic imaging system 10, as shown in FIG. 1, the operator OP moves the mobile radiographic imaging apparatus 11 to the side of a bed 15 first. Then, in a case where the radiation emission unit 24 is in a housing state as shown in FIG. 3, the radiation emission unit 24 is moved to the front of the carriage unit 14 as shown in FIG. 2 by manually rotating the column 22. Then, for example, the operator OP sets the irradiation conditions by operating the console 26, and then starts positioning.

In positioning, for example, first, the approximate position of the radiation emission unit 24 is determined above the bed 15 by manually rotating the column 22, expanding and contracting the column 22, and expanding and contracting the arm 23.

Then, the operator OP performs relative positioning between the electronic cassette 12 and the patient P on the bed 15. The position of the electronic cassette 12 is determined according to the imaging part of the patient P, so that the imaging part and the front surface 71A of the electronic cassette 12 face each other. The operator OP adjusts the direction and position of the electronic cassette 12 with the other hand while supporting the body of the patient P with one hand as necessary.

After the positioning between the patient P and the electronic cassette 12 is completed, relative positioning between the electronic cassette 12 and the radiation emission unit 24 is performed. In this case, the operator OP operates the remote operation unit 76 of the electronic cassette 12 to adjust the direction and position of the radiation emission unit 24. The operator OP operates the mechanism selection button 77 of the remote operation unit 76 to select a sub-displacement mechanism to be operated.

As shown in FIG. 6, the name or abbreviation of the selected sub-displacement mechanism is displayed on the indicator 66 of the radiation emission unit 24. The operator OP views the display to check whether or not the sub-displacement mechanism matching the intention of the operator OP has been selected. Then, after checking the selected sub-displacement mechanism, the operator OP operates the displacement amount adjustment button 78. As a result, the remote operation instruction is wirelessly transmitted to the mobile radiographic imaging apparatus 11 through the operation instruction transmission unit 84. In the mobile radiographic imaging apparatus 11, the displacement mechanism controller 61 controls the driving of the sub-displacement mechanism according to the received remote operation instruction. As a result, the direction and position of the radiation emission unit 24 are adjusted.

In a case where the relative posture between the radiation emission unit 24 and the electronic cassette 12 falls within the appropriate range, the illuminance of the irradiation field lamp 98 is increased. Therefore, the operator OP can check whether or not the relative posture between the radiation emission unit 24 and the electronic cassette 12 is within the appropriate range.

In a case where the positioning is completed, the irradiation switch 32 is operated to start irradiation. In a case where the irradiation switch 32 is operated, radiation is emitted from the radiation emission unit 24 toward the patient P. The electronic cassette 12 detects a radiographic image based on the radiation transmitted through the patient P. The detected radiographic image is transmitted from the image memory 82 to the mobile radiographic imaging apparatus 11 through the image transmission unit 83. In the mobile radiographic imaging apparatus 11, the received radiographic image is displayed on the console 26. The operator OP checks whether or not appropriate imaging has been performed by checking the radiographic image captured by the console 26.

As described above, in the mobile radiographic imaging system 10, the operator OP can transmit a remote operation instruction, which is for operating the displacement mechanism of the radiation emission unit 24, to the mobile radiographic imaging apparatus 11 through the operation instruction transmission unit 84 by operating the remote operation unit 76 of the electronic cassette 12. For this reason, the operator OP can adjust the position and direction of the radiation emission unit 24 without releasing the hand from the electronic cassette 12 at the time of positioning for radiographic imaging.

In many cases, the patient P who is to be imaged using the mobile radiographic imaging system 10 needs the assistance of the operator OP at the time of positioning. In such a case, both hands of the operator OP are busy, for example, one hand of the operator OP is on the patient P and the other hand is on the electronic cassette 12. For this reason, as in the mobile radiographic imaging system 10, the advantage of the technique of the present disclosure capable of adjusting the position and direction of the radiation emission unit 24 without releasing the hand from the electronic cassette 12 is great.

In this example, the displacement mechanism of the mobile radiographic imaging apparatus 11 has six sub-displacement mechanisms including the column rotation mechanism 51, the column expansion and contraction mechanism 52, the arm expansion and contraction mechanism 53, the irradiation unit rotation mechanism 54, the irradiation unit tilting mechanism 56, and the carriage unit traveling mechanism 57, and each of the sub-displacement mechanisms can be remotely operated. Therefore, the position and direction of the radiation emission unit 24 can be finely adjusted.

In addition, since the remote operation unit 76 in this example comprises the mechanism selection button 77 that is an example of a mechanism selection unit and the displacement amount adjustment button 78 that is an example of a displacement amount adjustment unit, it is not necessary to provide a displacement amount adjustment unit for each sub-displacement mechanism. Therefore, it is possible to simplify the configuration of the remote operation unit 76.

In this example, since the indicator 66 that displays a sub-displacement mechanism selected as an operation target is provided as an example of a selected mechanism display unit, the operator OP can easily check the selected sub-displacement mechanism. Therefore, the operability is improved.

In this example, the electronic cassette 12 is a wireless electronic cassette, and the operation instruction transmission unit 84 uses a wireless method. Therefore, since there is no cable that becomes an obstacle, positioning becomes easy.

In this example, the image transmission unit 83 and the operation instruction transmission unit 84 use different transmission paths. That is, the image transmission unit 83 and the operation instruction transmission unit 84 are different communication interfaces. Therefore, since it is only necessary to improve the operation instruction transmission unit 84 without modifying the communication interface of the existing image transmission unit 83, the design is easy.

In this example, in the housing 71 of the electronic cassette 12, the remote operation unit 76 is provided on the back surface 71B. Since the remote operation unit 76 is provided in addition to the front surface 71A of the electronic cassette 12 that becomes in contact with the body of the patient P at the time of positioning, the operation is easy.

In this example, the posture detection sensor 47 and the posture detection sensor 86, which are examples of a posture detection mechanism that detects the first posture of the radiation emission unit 24 and the second posture of the electronic cassette 12, are provided. The relative posture information deriving unit 96 that is an example of a deriving unit and the irradiation field lamp 98 that is an example of a posture information display unit are provided. Therefore, it is easy to check whether or not the relative posture between the radiation emission unit 24 and the electronic cassette 12 is within the appropriate range.

Aspect of a Remote Operation Unit

Figure 19:
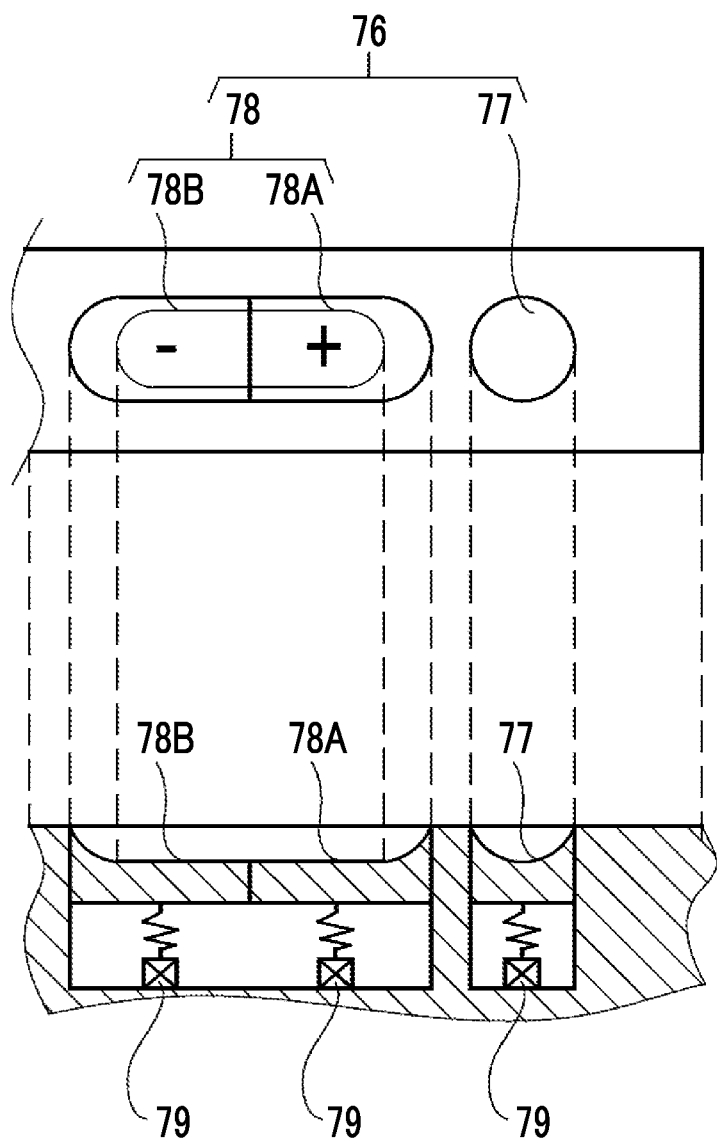
FIGS. 19A and 19B are diagrams showing a modification example of the remote operation unit, where

The aspect of the remote operation unit 76 is not limited to the above examples, but various modifications can be made. For example, as in Modification example 1 shown in FIGS. 19A and 19B, the mechanism selection button 77 and the displacement amount adjustment button 78 of the remote operation unit 76 may be formed in a recessed shape that is recessed with respect to the outer peripheral surface of the housing 71. By adopting the recessed shape, an erroneous operation in which the remote operation unit 76 is unintentionally operated is suppressed.

In the above example, an example has been described in which the remote operation unit 76 is provided on all of the four side surfaces 71C of the housing 71. However, the remote operation unit 76 may not be provided on all of the four side surfaces 71C, and may be provided on at least one side surface 71C.

Figure 20:
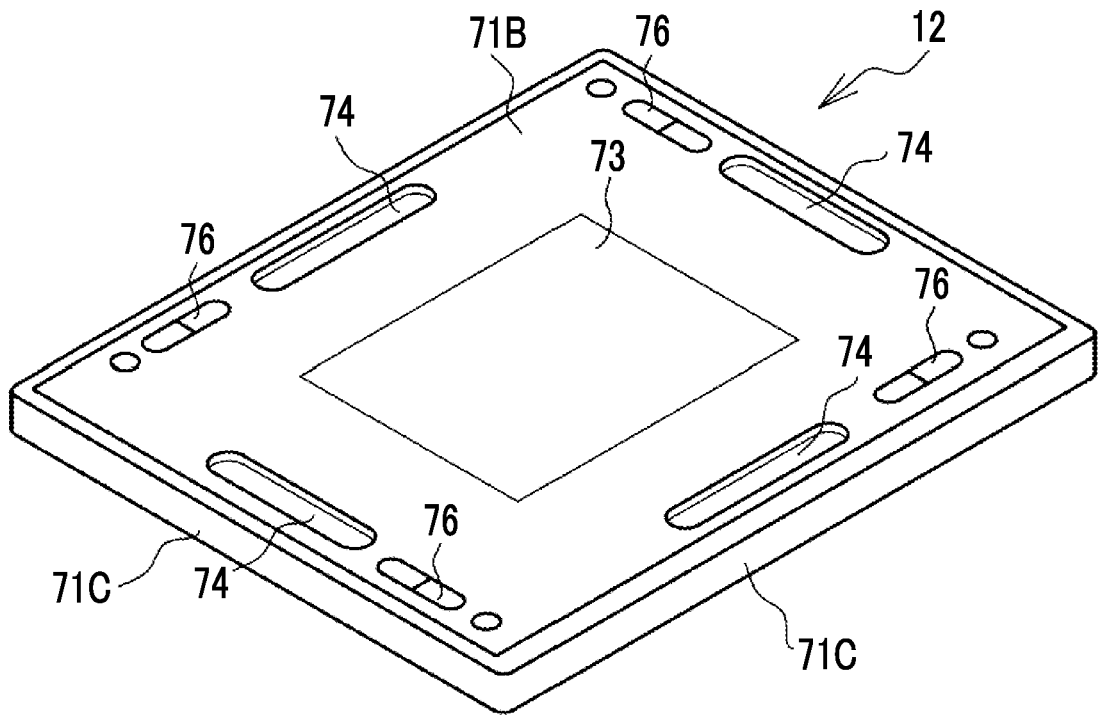
FIG. 20 is a diagram showing an example in which the remote operation unit is provided on a back surface.

As in Modification example 2 shown in FIG. 20, the remote operation unit 76 may be provided on the back surface 71B of the housing 71. In the example shown in FIG. 20, four remote operation units 76 are provided corresponding to the four sides of the back surface 71B. Since the back surface 71B is other than the front surface 71A, the operation is easy as in the case where the remote operation unit 76 is provided on the side surface 71C.

Figure 21:
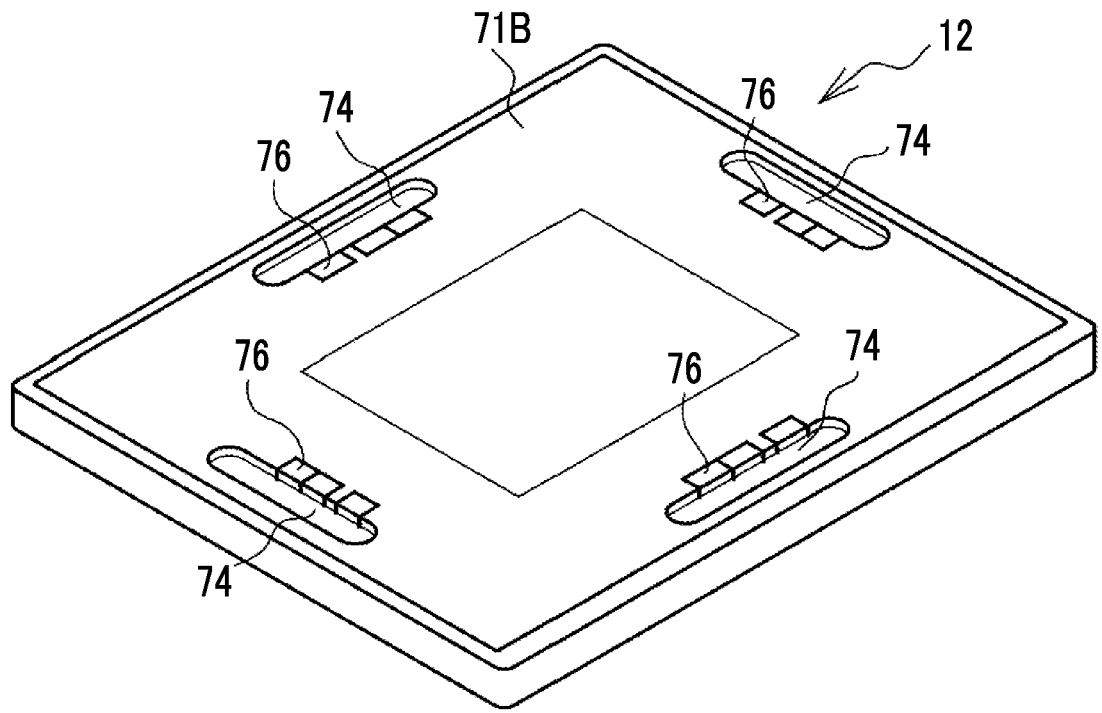
FIG. 21 is a diagram showing an example in which the remote operation unit is provided on the heel of a finger hanging portion.
Figure 22:
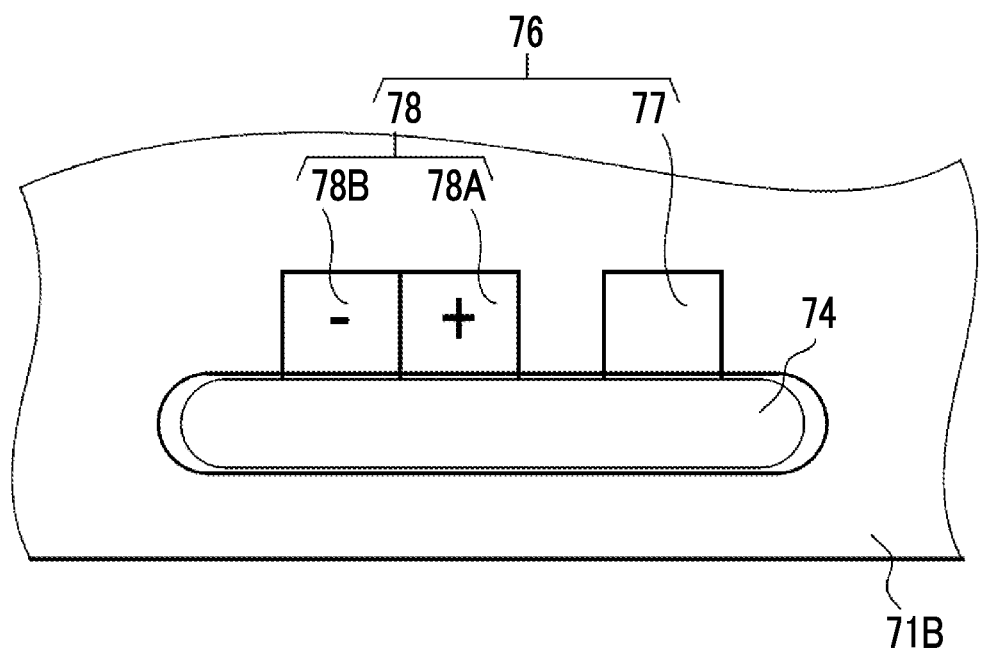
FIG. 22 is a plan view of the remote operation unit shown in FIG. 21.

As in Modification example 3 shown in FIGS. 21 and 22, the remote operation unit 76 may be provided on the heel of the finger hanging portion 74. The finger hanging portion 74 is a recessed portion, and the location can be checked by tactile sense. Therefore, in a case where the remote operation unit 76 is provided on the heel of the finger hanging portion 74, the finger hanging portion 74 and the remote operation unit 76 can be found by fumbling even in a case where the back surface 71B is hidden in a state in which the electronic cassette 12 is inserted between the patient P and the bed 15.

Figure 23:
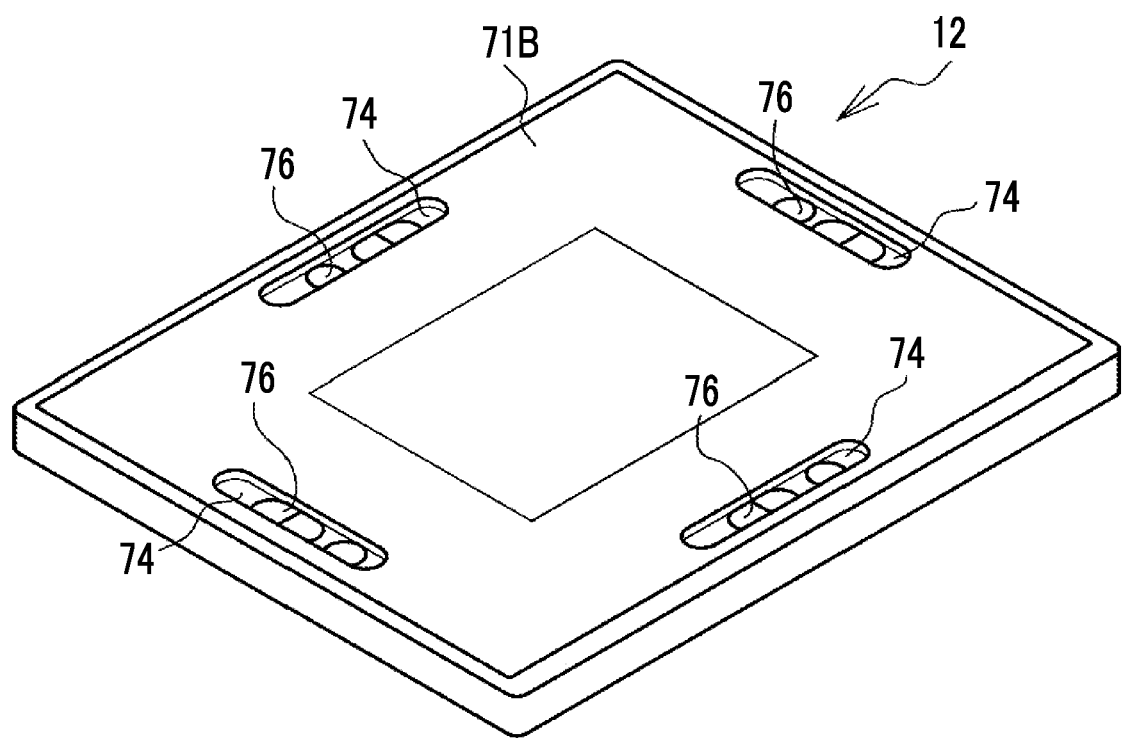
FIG. 23 is a diagram showing an example in which the remote operation unit is provided inside the finger hanging portion.

As in Modification example 4 shown in FIG. 23, the remote operation unit 76 may be provided inside the finger hanging portion 74. Since the finger hanging portion 74 is a recessed portion and is recessed one step from the outer peripheral surface, an erroneous operation is suppressed by providing the remote operation unit 76 inside the finger hanging portion 74.

The remote operation unit 76 in Modification example 3 shown in FIGS. 21 and 22 and Modification example 4 shown in FIG. 23 is the same as the remote operation unit 76 shown in FIGS. 10A and 10B and 19A and 19B in that the remote operation unit 76 is formed by the mechanism selection button 77 and the displacement amount adjustment button 78.

Figure 24:
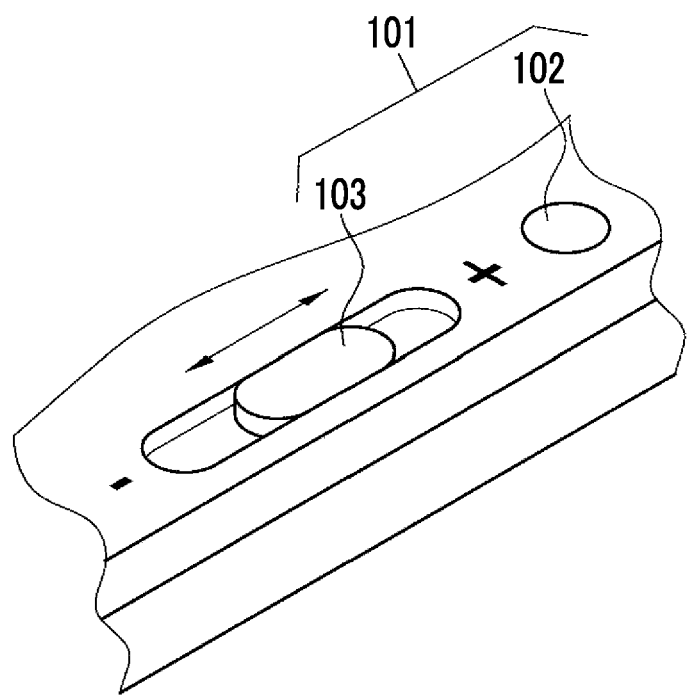
FIG. 24 is a diagram of an example in which a displacement amount adjustment button is a slide switch.

Alternatively, a remote operation unit 101 in Modification example 5 shown in FIG. 24 may be used. The remote operation unit 101 is configured to include a mechanism selection button 102 and a displacement amount adjustment button 103. The mechanism selection button 102 is the same push button type as the mechanism selection button 77. On the other hand, the displacement amount adjustment button 103 is not a push button type but a slide switch. The displacement amount adjustment button 103 is provided in an oval groove so as to be slidable in both the left and right directions in FIG. 24. In FIG. 24, an operation instruction is given with the amount of displacement on a positive side in a case where the displacement amount adjustment button 103 is made to slide in the right direction, and an operation instruction is given with the amount of displacement on a negative side in a case where the displacement amount adjustment button 103 is made to slide in the left direction.

Modification Example of Operation Instruction Transmission Unit

Figure 25:
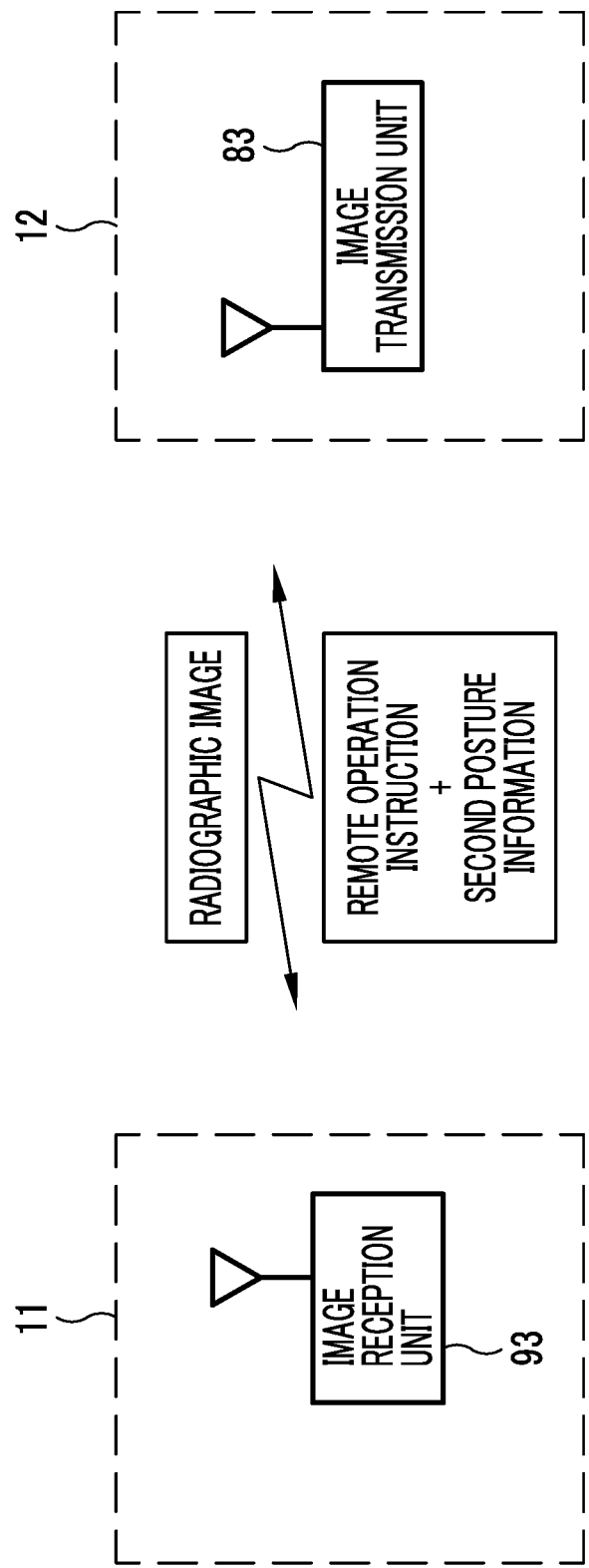
FIG. 25 is a diagram of an example in which an operation instruction transmission unit also serves as an image transmission unit.

In the above example, as shown in FIG. 12, an example has been described in which different transmission paths are used with the image transmission unit 83 and the operation instruction transmission unit 84 as different communication interfaces. However, as in Modification example 1 shown in FIG. 25, the image transmission unit 83 may also be used as the operation instruction transmission unit 84 that transmits the remote operation instruction and the second posture information. That is, by using the image transmission unit 83 as the operation instruction transmission unit 84, the image transmission unit 83 and the operation instruction transmission unit 84 may use the same transmission path. In this case, since it is not necessary to separately provide the operation instruction transmission unit 84, component costs are reduced.

Modification Example 1 of Relative Posture Information Display Unit

Figure 26:
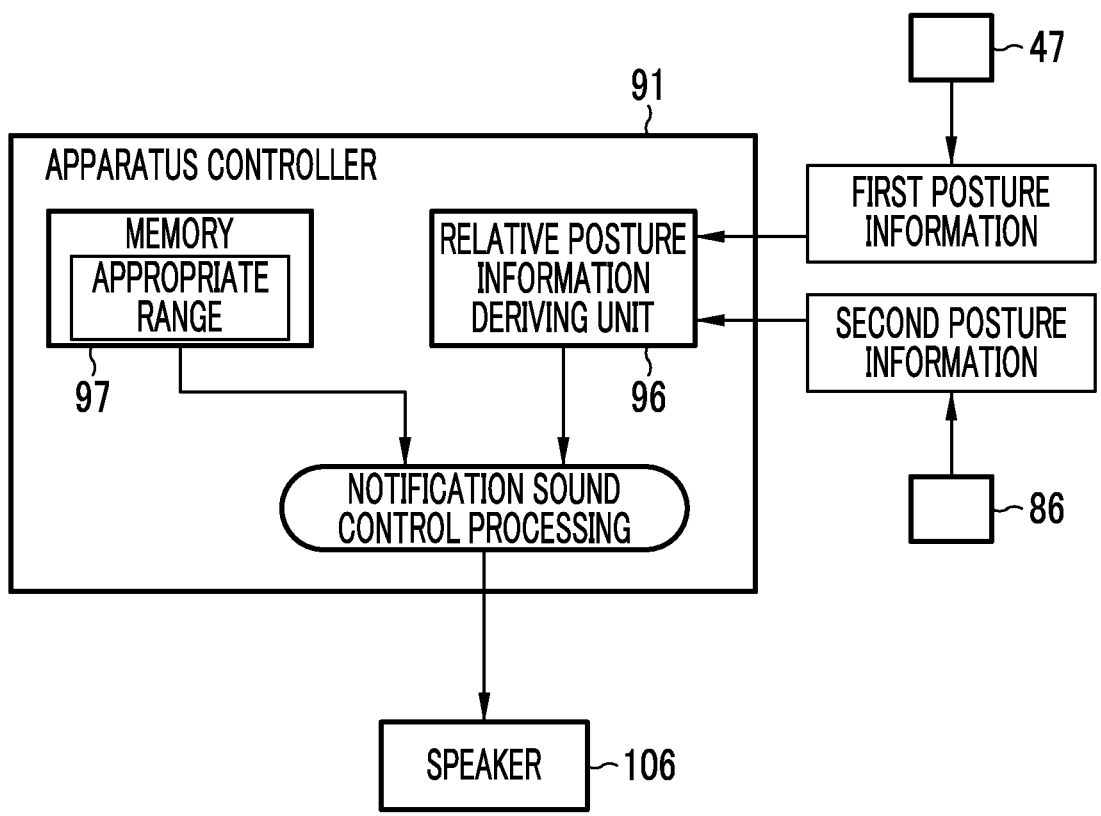
FIG. 26 is an explanatory diagram of an example in which notification that the relative posture between the radiation emission unit and the electronic cassette falls within the appropriate range is provided by using a speaker.

In the above example, a form has been described in which the irradiation field lamp 98 is used as a relative posture information display unit and the relative posture information between the radiation emission unit 24 and the electronic cassette 12 are displayed by changing the illuminance of the irradiation field lamp 98. As in a modification example shown in FIG. 26, a speaker 106 may be used as a relative posture information display unit. In this case, the apparatus controller 91 executes notification sound control processing for controlling the notification sound of the speaker 106. Specifically, the volume of the speaker 106 is increased as the relative posture between the radiation emission unit 24 and the electronic cassette 12 approaches the appropriate range, and, for example, the volume is maximized in a case where the relative posture between the radiation emission unit 24 and the electronic cassette 12 falls within the appropriate range. By such a change in volume, the operator OP can grasp the relative posture information between the radiation emission unit 24 and the electronic cassette 12.

Modification Example 2 of Relative Posture Information Display Unit

Figure 27:
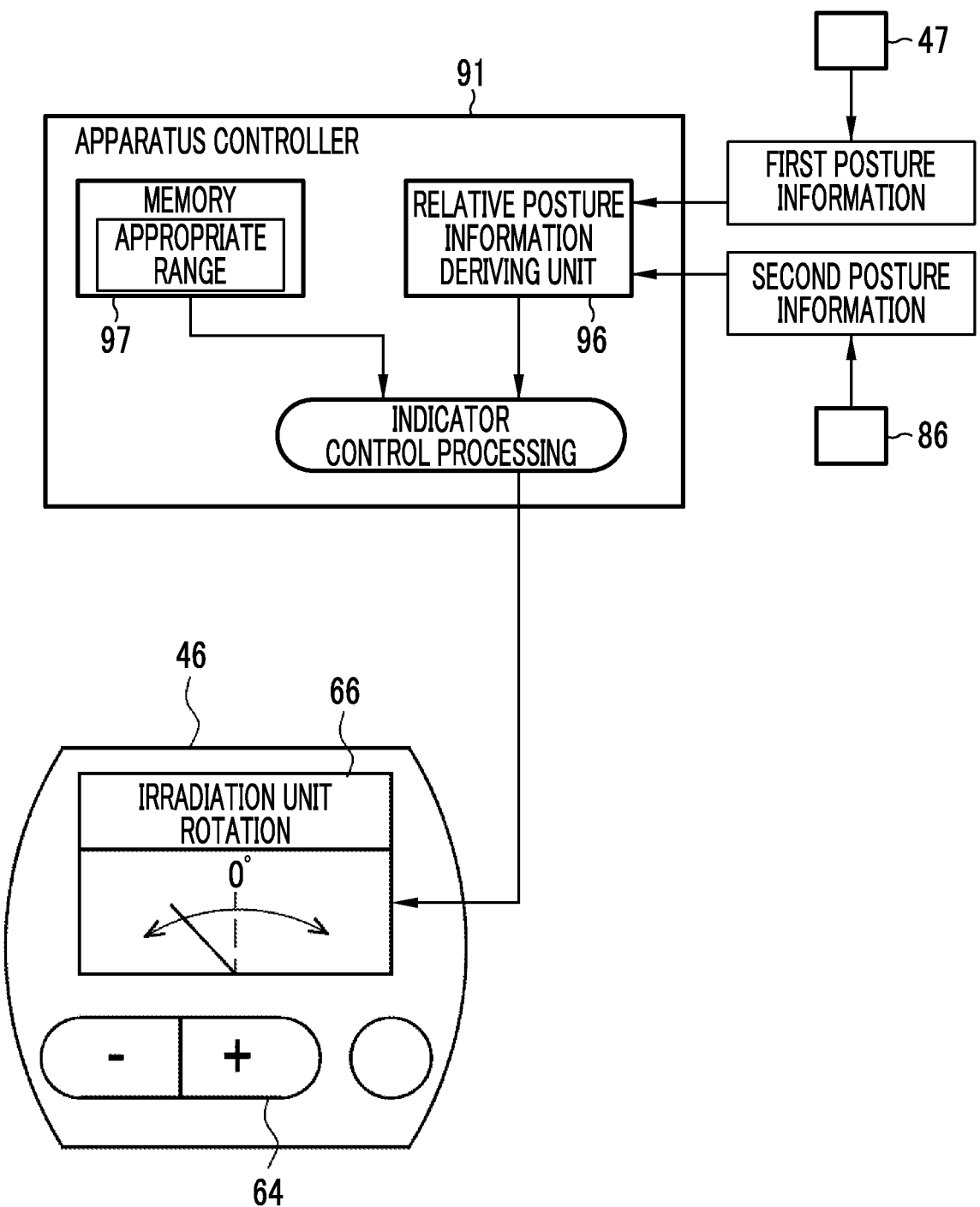
FIG. 27 is an explanatory diagram of an example in which notification that the relative posture between the radiation emission unit and the electronic cassette falls within the appropriate range is provided by using an indicator.

As in Modification example 2 shown in FIG. 27, the indicator 66 of the operation panel 46 may be used as a relative posture information display unit. In addition to the name of the sub-displacement mechanism selected as an operation target, relative posture information is displayed on the indicator 66. As the relative posture information, the angle $\theta 12$ formed by the incidence axis RA of the radiation emission unit 24 and the normal N of the electronic cassette 12 is displayed. The apparatus controller 91 executes indicator control processing for displaying relative posture information. In the indicator control processing, as a display mode of the angle $\theta 12$, for example, the scale of an appropriate position where the angle $\theta 12$ is 0° is displayed at the center position. Then, a current angle indicating the value of the current angle $\theta 12$ is displayed in the form of a meter, and a difference between the meter indicating the current angle and the scale of the appropriate position is shown, thereby displaying whether or not the relative posture is within the appropriate range.

Modification Example 1 of Remote Operation Instruction

Figure 28:
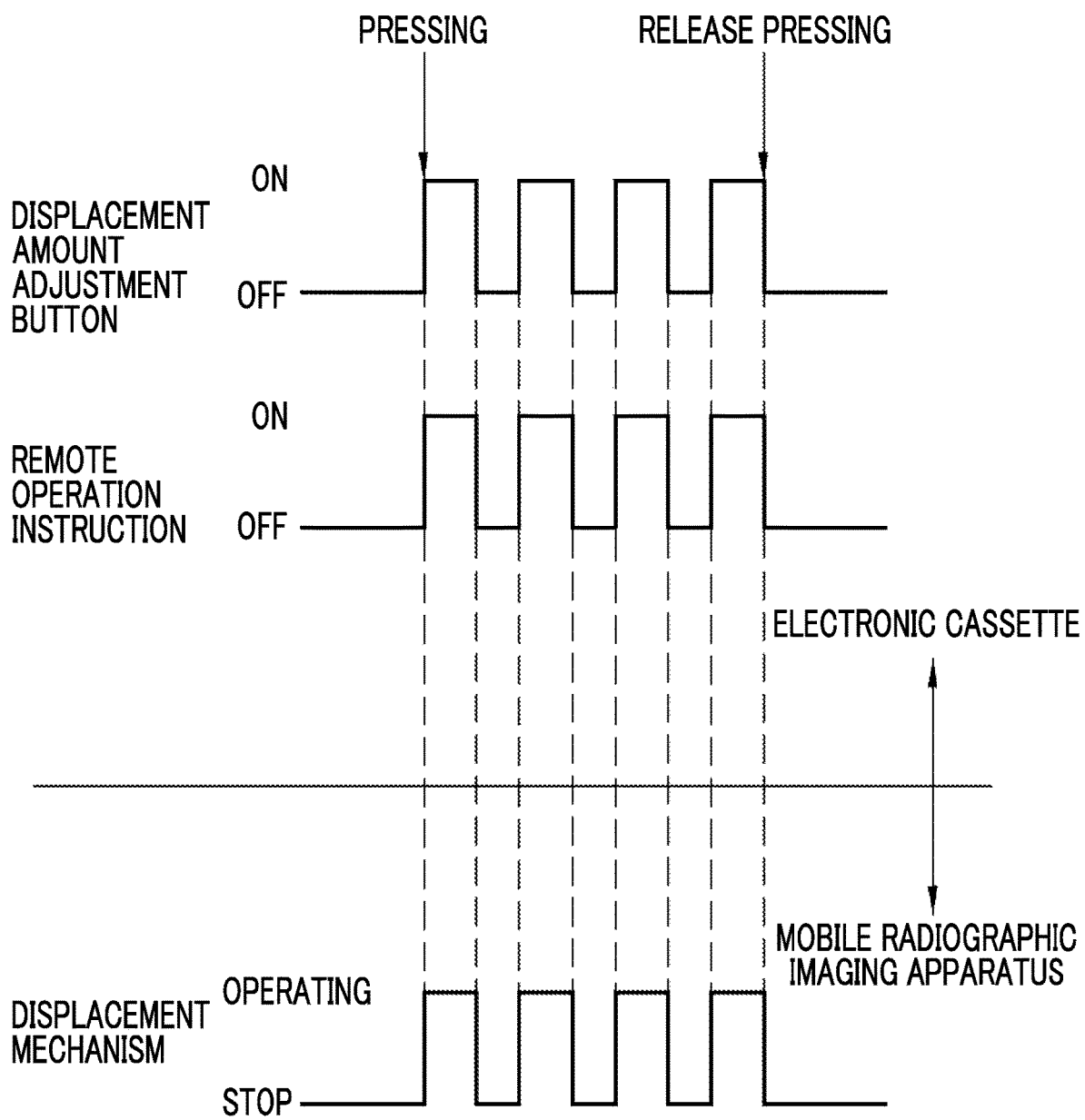
FIG. 28 is a diagram showing a modification example of the output form of the signal of the remote operation instruction.

In the above example, as shown in FIG. 11, an output form in which the remote operation instruction is continuously turned on while the displacement amount adjustment button 78 is pressed has been described as the output form of the signal of the remote operation instruction. Instead of the output form, as shown in FIG. 28, an output form may be adopted in which a pulse signal that is repeatedly turned on and off at a cycle set in advance as a remote operation instruction continues while the displacement amount adjustment button 78 is pressed. The output form shown in FIG. 28 is the same as the output form shown in FIG. 11 in that the transmission of the remote operation instruction is continued while an operation of pressing the displacement amount adjustment button 78 is continued. However, since the operation of the displacement mechanism is step-driven by using a pulse signal shown in FIG. 28, the radiation emission unit 24 is displaced stepwise. Therefore, it is easy to finely adjust the direction and position of the radiation emission unit 24.

Modification Example 2 of Remote Operation Instruction

Figure 29:
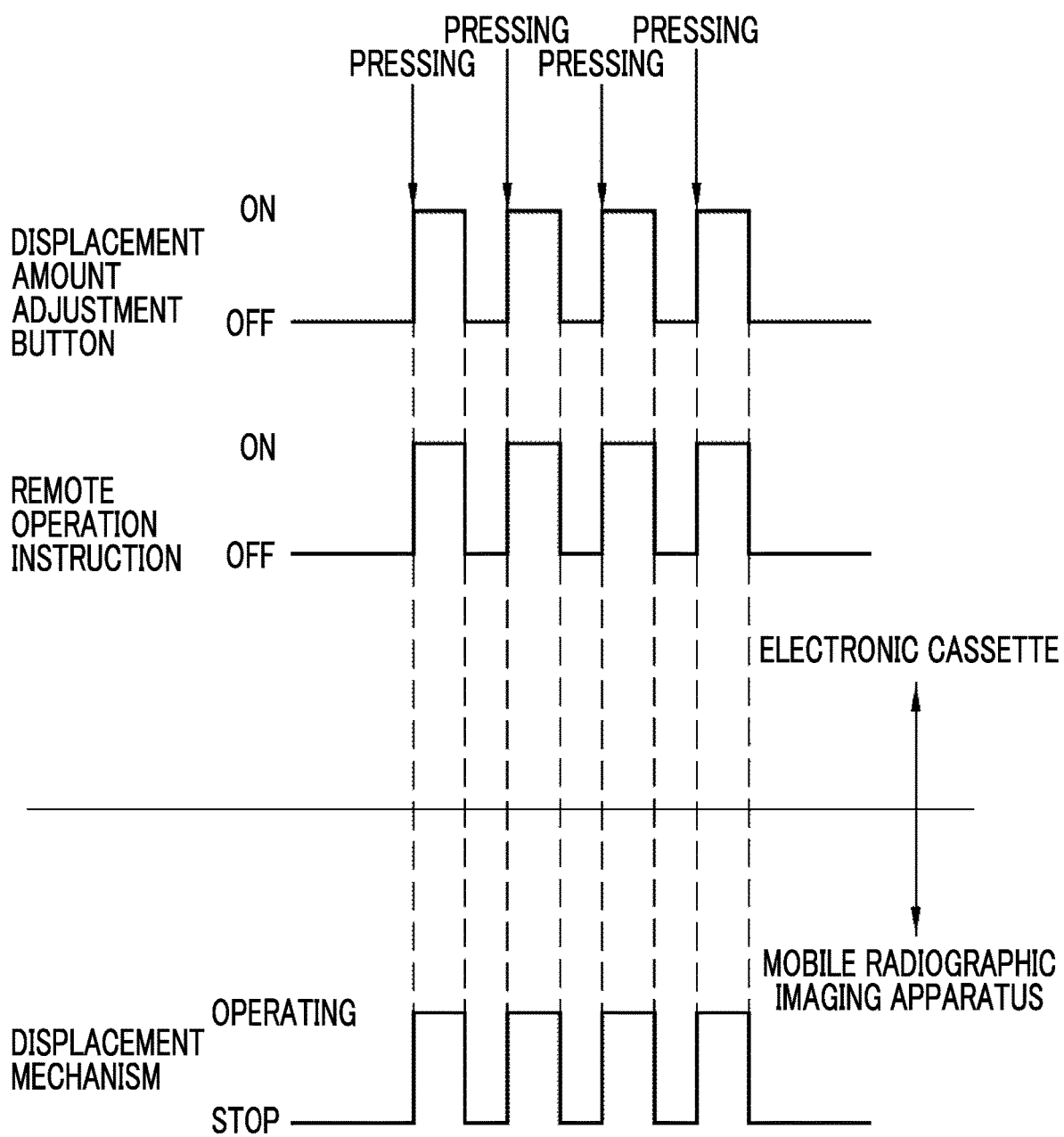
FIG. 29 is a diagram showing another modification example of the output form of the signal of the remote operation instruction.

In addition, as shown in FIG. 29, an output form in which one pulse signal is transmitted by one pressing operation may be adopted. In the output form shown in FIG. 29, even in a case where the pressing operation is continued, the pulse signal is not continuously output. Therefore, the direction and position of the radiation emission unit 24 can be easily finely adjusted.

Modification Example 3 of Remote Operation Instruction

Figure 30:
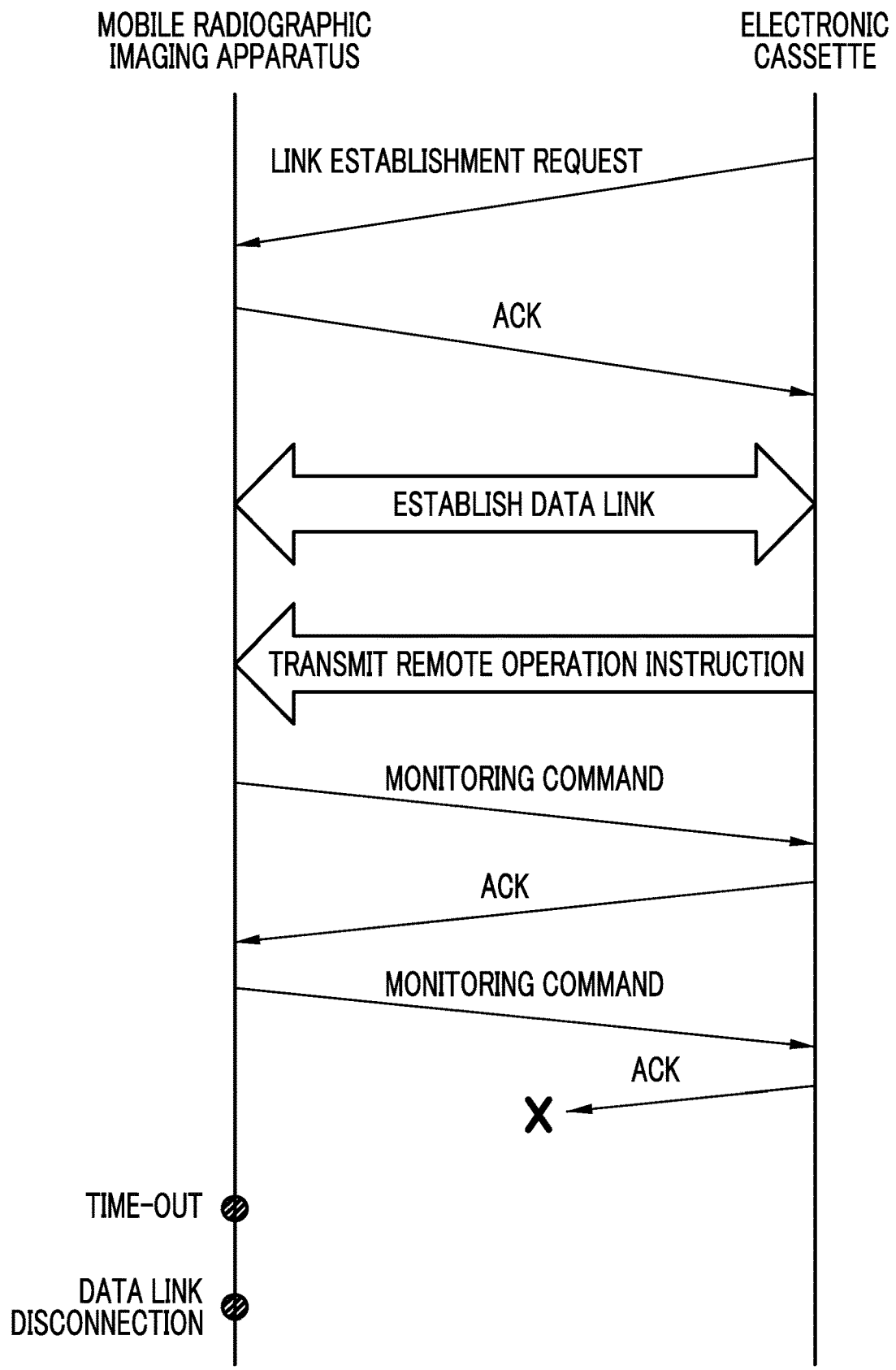
FIG. 30 is an explanatory diagram of a form in which a data link is established to transmit a remote operation instruction.

As shown in FIG. 30, in the communication of the remote operation instruction, remote operation instruction communication may be performed after a data link is established between the electronic cassette 12 and the mobile radiographic imaging apparatus 11. In this case, the displacement mechanism controller 61 of the mobile radiographic imaging apparatus 11 receives a remote operation instruction once from the operation instruction transmission unit 84 of the electronic cassette 12 and then continues the operation of the displacement mechanism until a stop instruction from the operation instruction transmission unit 84 is received. After receiving the remote operation instruction, the displacement mechanism controller 61 monitors whether or not a data link is established until the stop instruction is received, and stops the operation of the displacement mechanism even though the stop instruction is not received in a case where the data link is disconnected.

In the example shown in FIG. 30, in a case where the displacement amount adjustment button 78 is pressed, first, the operation instruction transmission unit 84 of the electronic cassette 12 performs a handshake to establish a data link between the operation instruction transmission unit 84 and the operation instruction reception unit 94 of the mobile radiographic imaging apparatus 11. Specifically, the handshake is a transmission of a link establishment request and an exchange of an ACK signal that is a positive response thereto.

After the data link is established, in the mobile radiographic imaging apparatus 11, the displacement mechanism controller 61 transmits a monitoring command, which is for monitoring whether or not a data link is established, to the operation instruction transmission unit 84 of the electronic cassette 12 through the operation instruction reception unit 94. In a case where there is an ACK signal, which is a positive response from the electronic cassette 12, with respect to the monitoring command, the displacement mechanism controller 61 continues the operation of the displacement mechanism.

On the other hand, in a case where there is no response of the ACK signal with respect to the monitoring command and time-out occurs, the displacement mechanism controller 61 disconnects the data link of the operation instruction reception unit 94. In this case, the displacement mechanism controller 61 stops the operation of the displacement mechanism even though the stop instruction is not received.

According to the example shown in FIG. 30, the mobile radiographic imaging apparatus 11 continues the operation of the displacement mechanism on condition that the data link is established. For example, in a case where the operation of the displacement mechanism is continued in a state in which communication is unstable due to communication failure or the like, a stop instruction from the electronic cassette 12 may not reach the mobile radiographic imaging apparatus 11 even though the operator OP has performed an operation. As a result, the operation of the displacement mechanism may continue. Such inconvenience can be avoided by monitoring the data link.

Second Embodiment

Figure 31:
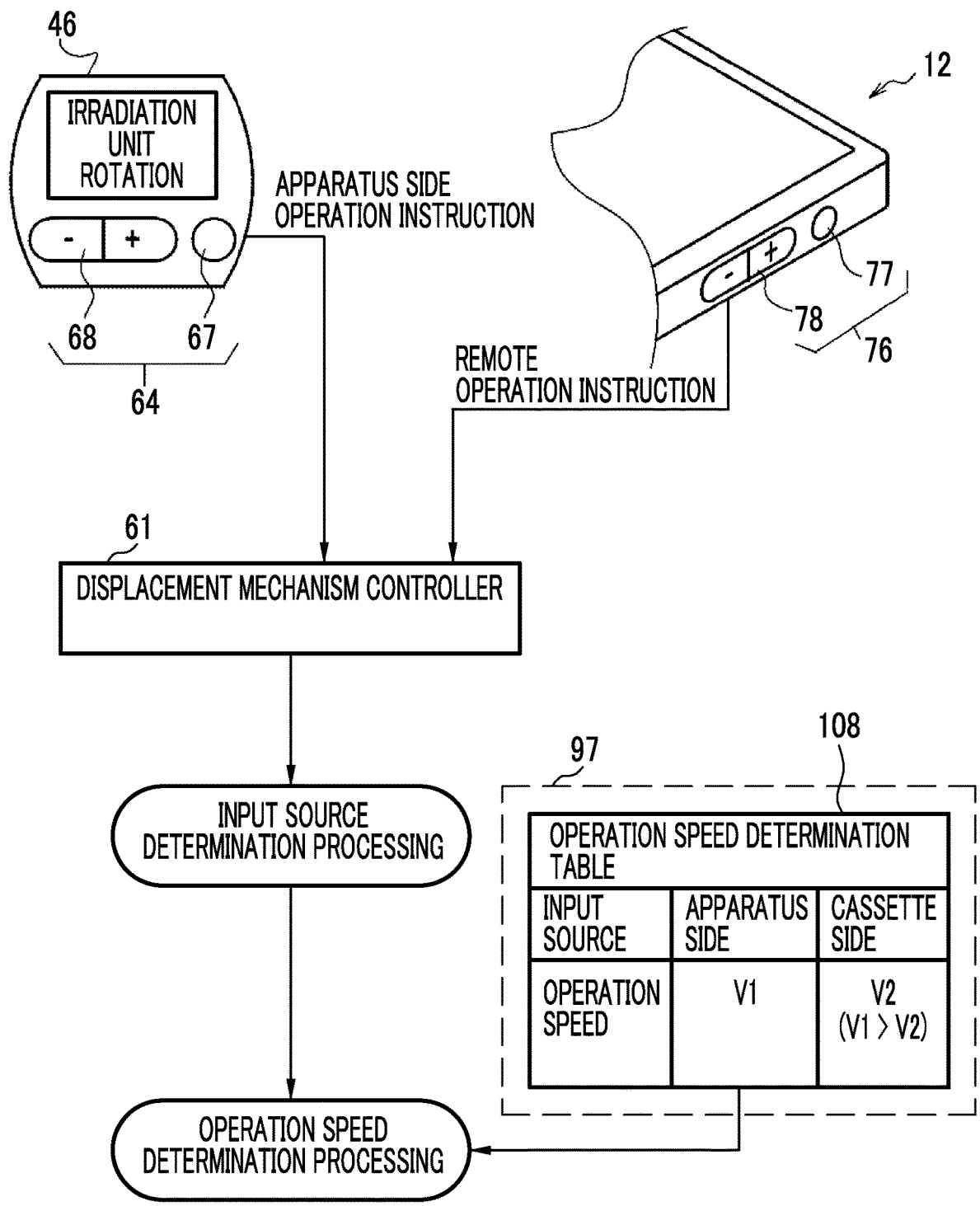
FIG. 31 is a diagram showing a second embodiment.

A second embodiment shown in FIG. 31 is a form in which the operation speed of a displacement mechanism is changed according to the input source of an operation instruction with respect to the displacement mechanism. As described above, the mobile radiographic imaging system 10 comprises the apparatus side operation unit 64 of the mobile radiographic imaging apparatus 11 and the remote operation unit 76 of the electronic cassette 12. The displacement mechanism controller 61 can receive both an apparatus side operation instruction from the apparatus side operation unit 64 and a remote operation instruction from the remote operation unit 76.

In the second embodiment shown in FIG. 31, in the case of operating the displacement mechanism based on the remote operation instruction, the displacement mechanism controller 61 performs control to lower the operation speed of the displacement mechanism than in the case of operating the displacement mechanism based on the apparatus side operation instruction. An operation speed determination table 108 is stored in the memory 97 of the apparatus controller 91. In the operation speed determination table 108, operation speeds V1 and V2 corresponding to the input source of the operation instruction are set. The operation speed V2 is an operation speed in a case where the input source of the operation instruction is the remote operation unit 76 of the electronic cassette 12, and is set to be lower than the operation speed V1 in a case where the input source is the apparatus side operation unit 64. In a case where the operation instruction is the remote operation instruction from the remote operation unit 76, the displacement mechanism controller 61 operates the displacement mechanism at the operation speed V2 with reference to the operation speed determination table 108.

In many cases, the remote operation from the electronic cassette 12 with respect to the displacement mechanism of the mobile radiographic imaging apparatus 11 is for the purpose of fine adjustment after the end of rough registration. Therefore, fine adjustment can be easily performed by setting the operation speed V2 to be lower than the operation speed V1. In addition, in the case of operating the displacement mechanism by operating the apparatus side operation unit 64, the operation is performed in a state in which the operator OP is near the mobile radiographic imaging apparatus 11. On the other hand, in a case where the displacement mechanism is remotely operated from the electronic cassette 12, the distance between the mobile radiographic imaging apparatus 11 and the operator OP is relatively larger than that in a case where the apparatus side operation unit 64 is operated. For this reason, setting the operation speed V2 to be lower than the operation speed V1 is advantageous in that the safety against unexpected situations can be further improved.

Third Embodiment

Figure 32:
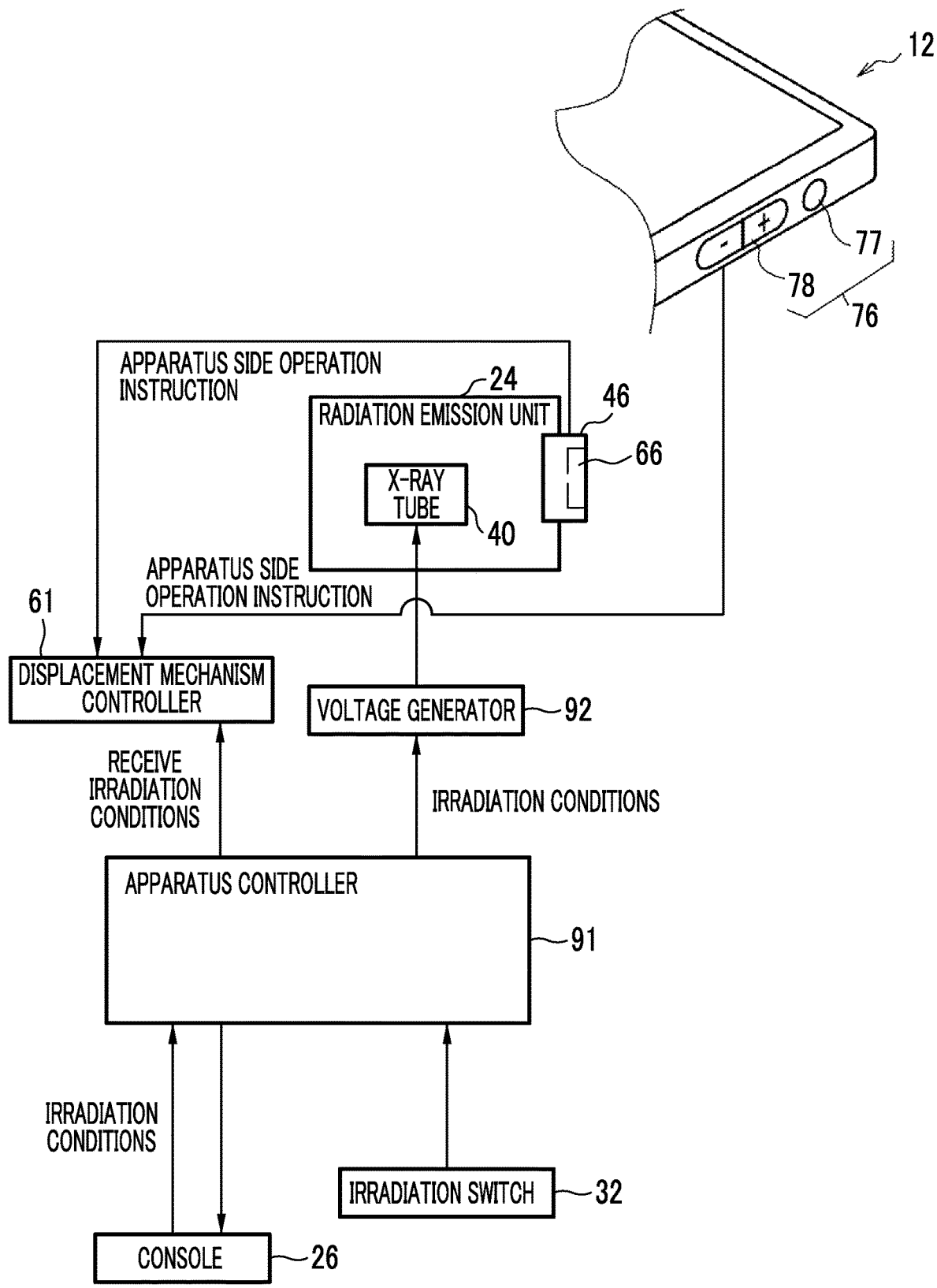
FIG. 32 is a schematic diagram showing a third embodiment.
Figure 33:
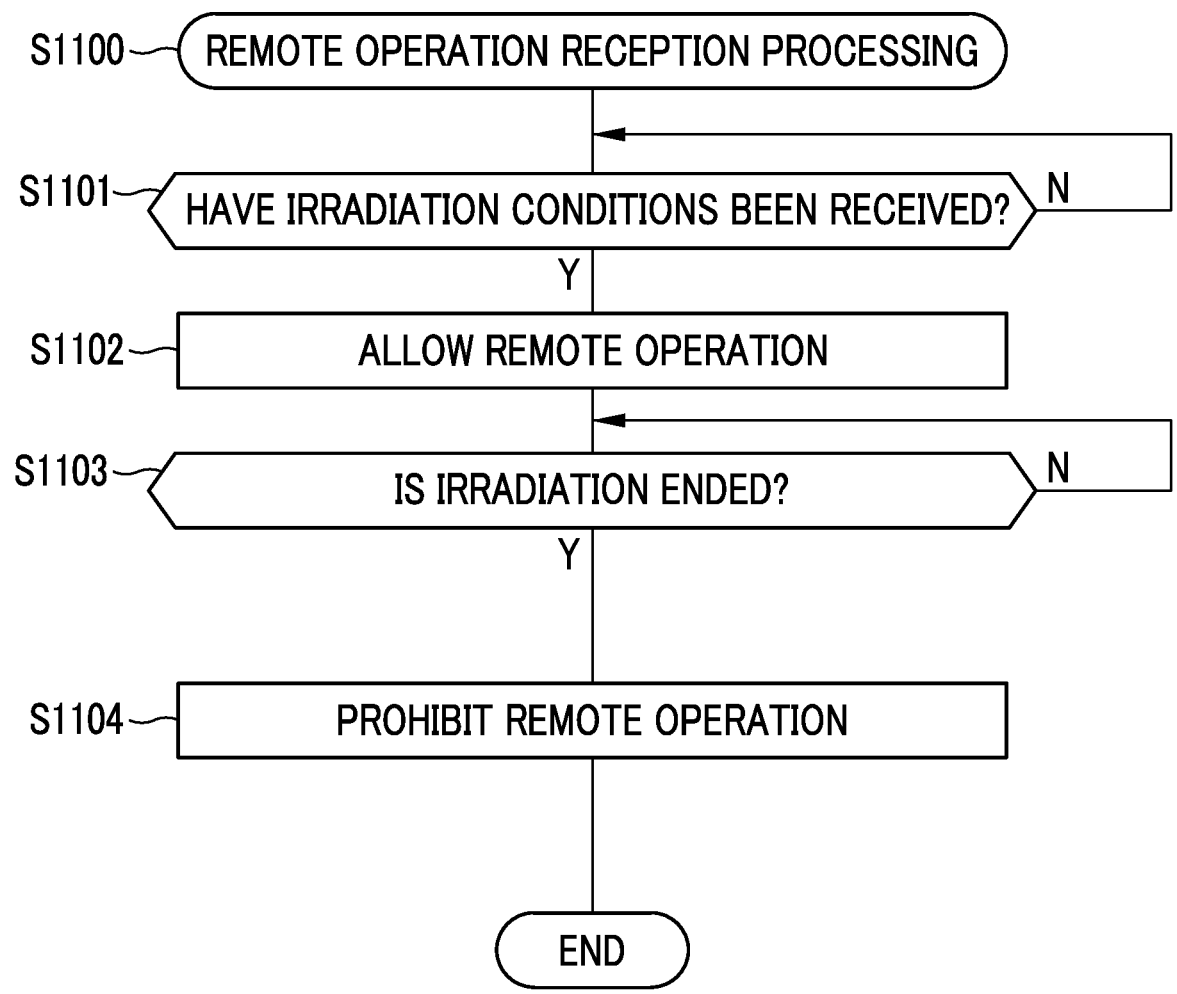
FIG. 33 is a flowchart of the third embodiment.

A third embodiment shown in FIGS. 32 and 33 is a form in which a remote operation on the displacement mechanism is allowed only in a case where it is considered that positioning is being performed. In imaging, before positioning is performed, the irradiation conditions of the X-ray tube 40 are set by the operation of the operator OP in many cases. The irradiation conditions are set through the console 26. The console 26 is an example of an irradiation conditions reception unit. In a case where the console 26 receives the irradiation conditions, the console 26 inputs the received irradiation conditions to the apparatus controller 91. In addition, the console 26 inputs reception information, which indicates that the irradiation conditions have been received, to the displacement mechanism controller 61.

The apparatus controller 91 sets the irradiation conditions in the voltage generator 92. In a case where the irradiation switch 32 is operated, radiation corresponding to the irradiation conditions from the radiation emission unit 24 is emitted. The apparatus controller 91 transmits to the displacement mechanism controller 61 that the emission of radiation has ended.

After the console 26 receives the irradiation conditions, the displacement mechanism controller 61 allows the remote operation from the remote operation unit 76 with respect to the displacement mechanism only until the radiation emission unit 24 ends the irradiation based on the received irradiation conditions.

Specifically, as shown in the flowchart of FIG. 33, the displacement mechanism controller 61 determines whether or not the irradiation conditions have been received in step S1101 of remote operation reception processing shown in step S1100. In a case where the irradiation conditions are received (Y in step S1101), the process proceeds to step S1102 in which the displacement mechanism controller 61 allows a remote operation. Then, in step S1103, the end of the emission of radiation is awaited. In a case where the emission of radiation has ended, the process proceeds to step S1104 to prohibit the remote operation.

Thus, in the third embodiment, the remote operation is allowed only in a case where it is considered that positioning is being performed. That is, since the remote operation from the electronic cassette 12 with respect to the displacement mechanism is an operation required only during positioning, a period during which the remote operation is allowed is limited to the necessary minimum. In this manner, an unintentional remote operation is suppressed.

Modification Example of Third Embodiment

Figure 34:
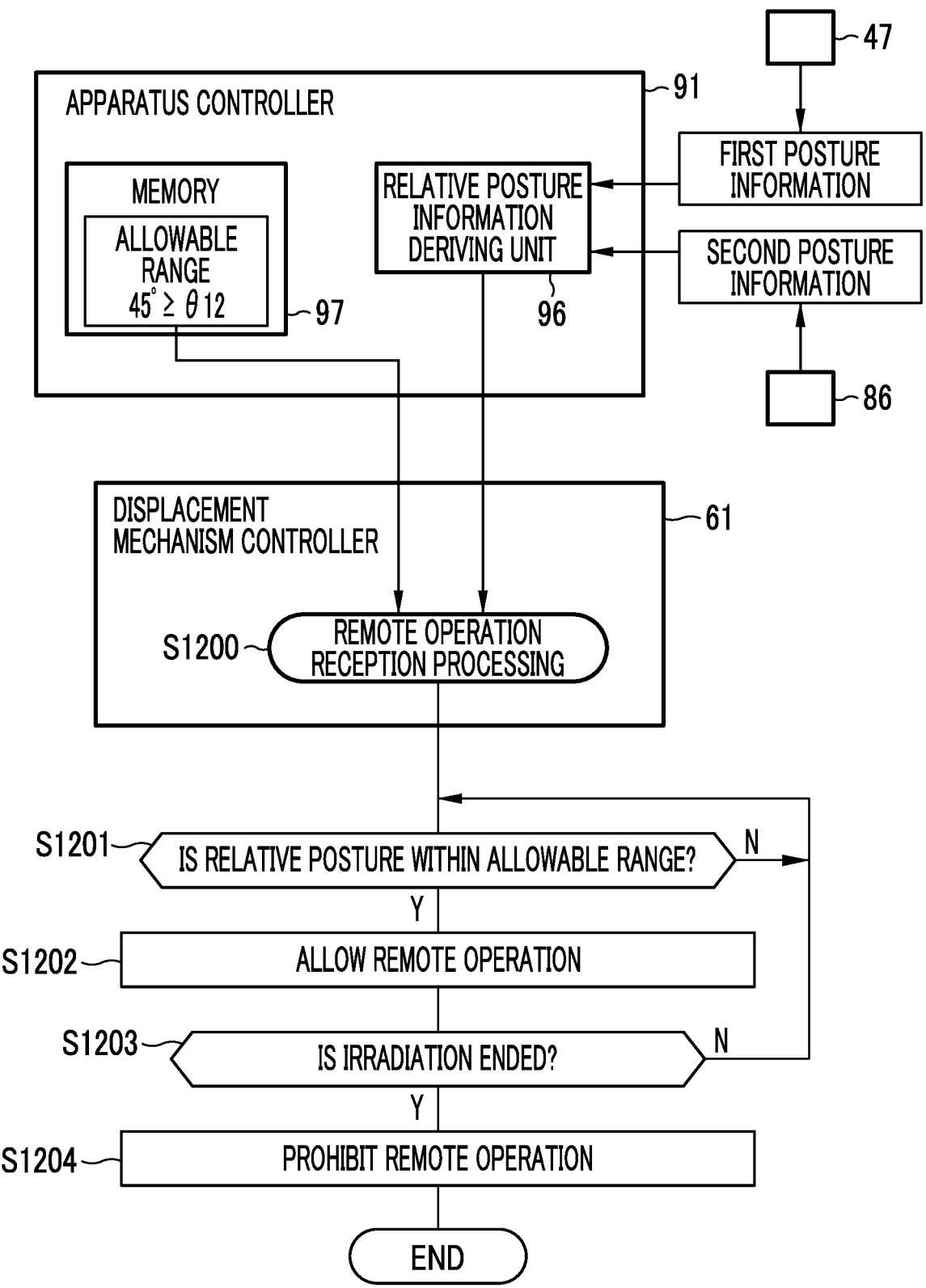
FIG. 34 is a diagram showing a modification example of the third embodiment.

A modification example of the third embodiment shown in FIG. 34 is an example in which the conditions of whether or not the relative posture between the radiation emission unit 24 and the electronic cassette 12 is within an allowable range set in advance are used as conditions for estimating that positioning is being performed.

That is, at a stage in which rough registration between the radiation emission unit 24 and the electronic cassette 12 has ended, it is considered that the relative posture between the radiation emission unit 24 and the electronic cassette 12 is in a positional relationship in which the radiation emission unit 24 and the electronic cassette 12 face each other to some extent even outside the appropriate range. In a case where the relative posture is in such a state, it can be estimated that positioning is being performed. For example, the allowable range is set such that the angle θ12 is equal to or less than 45°. The allowable range is stored in the memory 97.

In this example, the displacement mechanism controller 61 executes remote operation reception processing shown in step S1200. In step 1201, the displacement mechanism controller 61 determines whether or not the relative posture indicated by the angle θ12 calculated by the relative posture information deriving unit 96 is within the allowable range read from the memory 97. In a case where the determination is positive in step S1201, the process proceeds to step S1202 to allow the remote operation. In this manner, the remote operation is allowed only while the relative posture is within the allowable range. The remote operation is allowed until irradiation ends (Y in step S1203). In a case where the irradiation has ended, the remote operation is prohibited in step S1204. The displacement mechanism controller 61 and the relative posture information deriving unit 96 are examples of a relative posture determination unit.

As described above, also in the example shown in FIG. 34, as in the example in FIGS. 32 and 33, the period during which the remote operation is allowed is limited to a necessary period, so that it is possible to suppress an unintentional remote operation.

Fourth Embodiment

Figure 35:
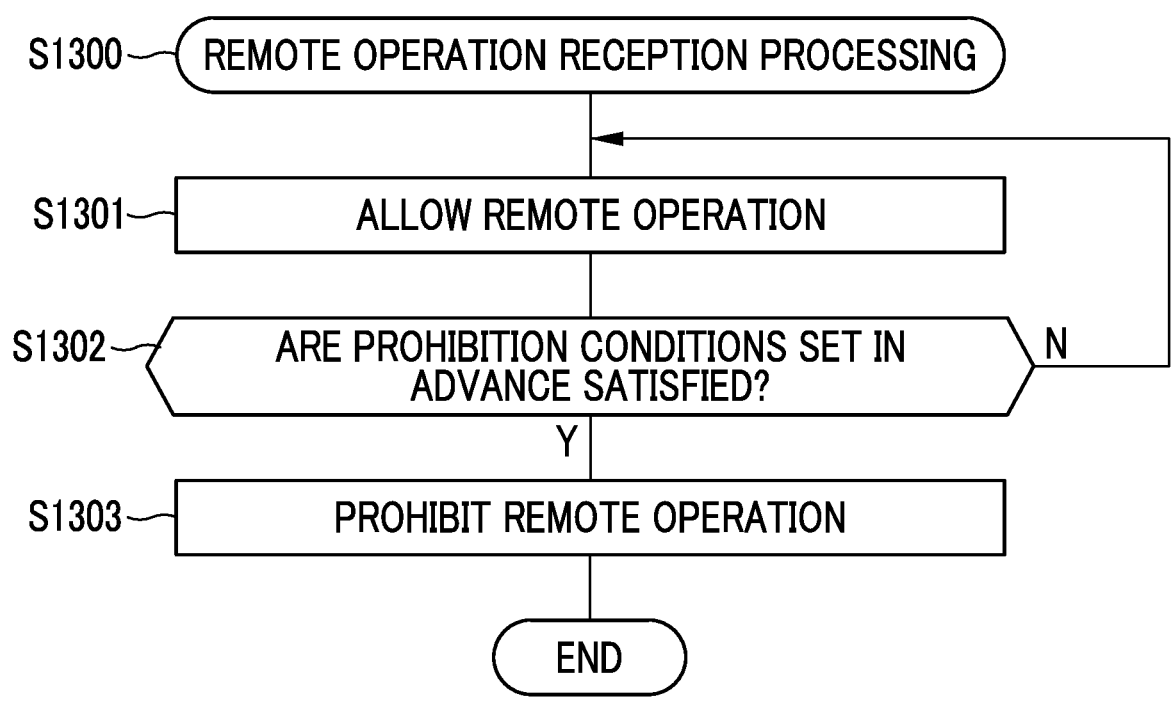
FIG. 35 is a flowchart of a fourth embodiment.
Figure 36:
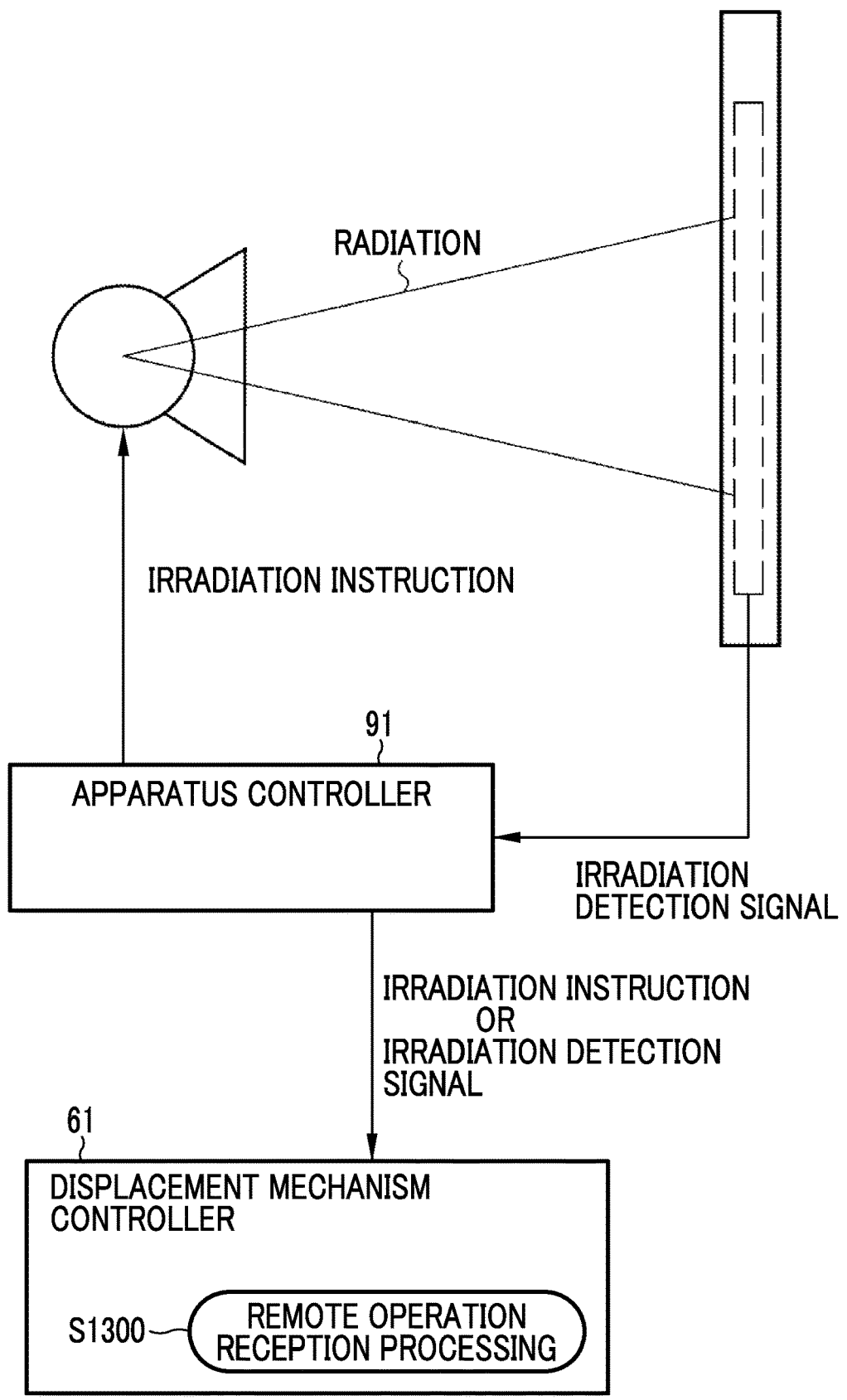
FIG. 36 is a diagram showing an example of the prohibition conditions of the fourth embodiment.
Figure 37:
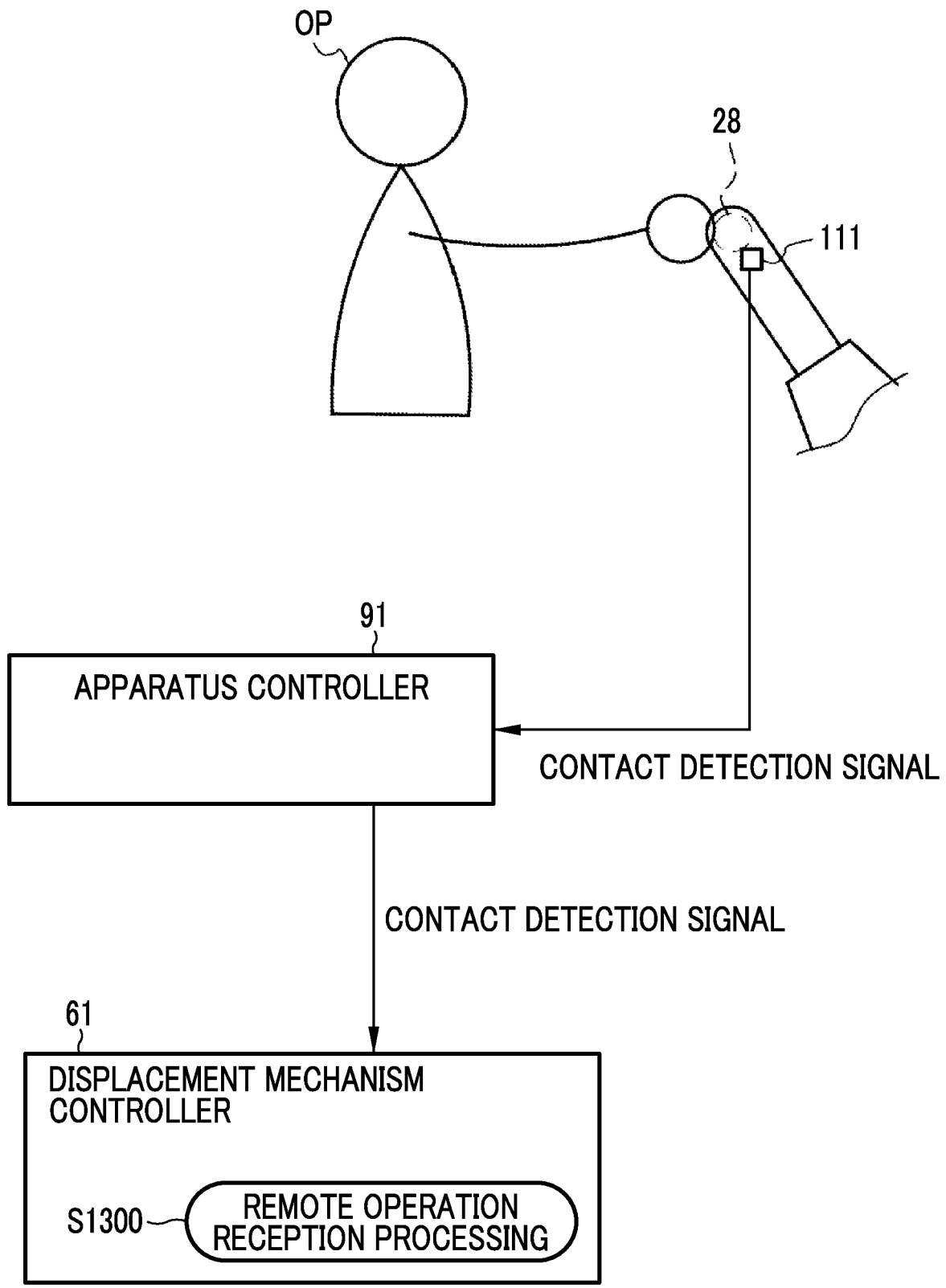
FIG. 37 is a diagram showing another example of the prohibition conditions of the fourth embodiment.
Figure 38:
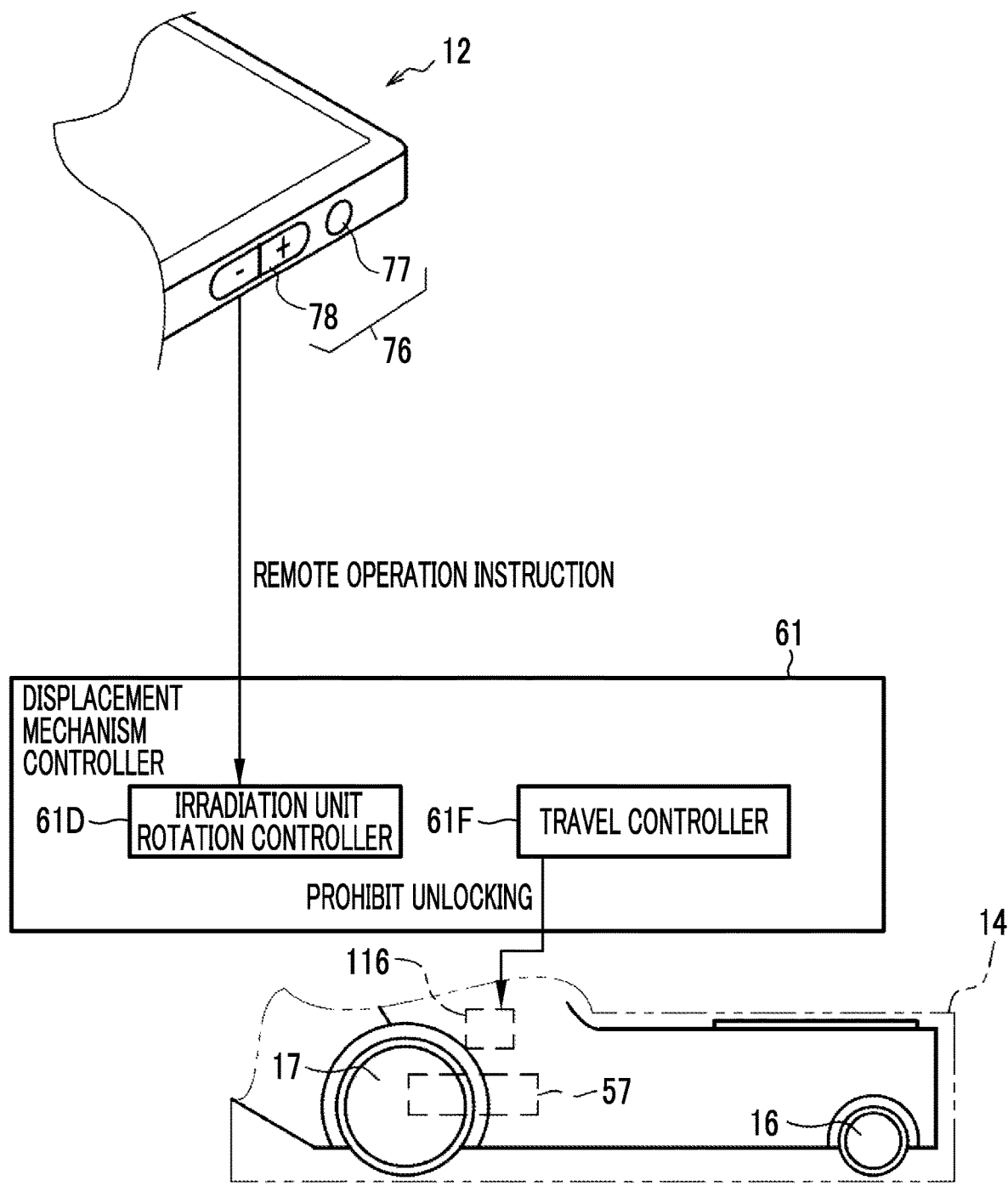
FIG. 38 is a schematic diagram showing a fifth embodiment.

A fourth embodiment shown in FIGS. 35 to 37 is a form in which a remote operation is prohibited in a case where prohibition conditions set in advance are satisfied. The third embodiment is a form that defines conditions under which the remote operation is allowed, while the fourth embodiment is a form that defines conditions under which the remote operation is actively prohibited.

As shown in the flowchart of FIG. 35, the displacement mechanism controller 61 executes remote operation reception processing shown in step S1300. In a case where the remote operation is allowed in step S1301, the displacement mechanism controller 61 monitors whether or not the prohibition conditions set in advance are satisfied in step S1302. In a case where the prohibition conditions are satisfied (Y in step S1202), the displacement mechanism controller 61 proceeds to step S1303 to prohibit the remote operation. In a case where the conditions under which the remote operation is allowed are satisfied again, the process returns to step S1301. Such processing is continued until the mobile radiographic imaging apparatus 11 or the electronic cassette 12 is turned off.

FIGS. 36 and 37 show specific examples of prohibition conditions. FIG. 36 shows, as an example of prohibition conditions, a case where an irradiation instruction from the irradiation switch 32 is input or a case where the start or end of the emission of radiation is detected by the electronic cassette 12 and an irradiation detection signal is input. The displacement mechanism controller 61 acquires an irradiation instruction or an irradiation detection signal through the apparatus controller 91. The displacement mechanism controller 61 prohibits the remote operation in a case where the irradiation instruction or the irradiation detection signal is acquired. The stage in which the irradiation instruction or the irradiation detection signal is generated is considered to be a stage in which the positioning ends. Therefore, by setting the generation of the irradiation instruction or the irradiation detection signal as prohibition conditions, the period during which the remote operation is allowed can be limited to a necessary period. In this manner, it is possible to suppress an unintentional remote operation.

FIG. 37 is an example in which the contact of the operator OP with the mobile radiographic imaging apparatus 11 is prohibition conditions. A contact detection sensor 111 is provided in the handle 28 of the mobile radiographic imaging apparatus 11. The contact detection sensor 111 is configured by, for example, a piezoelectric element. The displacement mechanism controller 61 acquires a contact detection signal through the apparatus controller 91. Then, the remote operation is prohibited with the generation of the contact detection signal as prohibition conditions.

The case where the operator OP is in contact with the handle 28 of the mobile radiographic imaging apparatus 11 is considered to be a stage in which imaging has ended or a case where the operator OP directly operates the mobile radiographic imaging apparatus 11 to move the mobile radiographic imaging apparatus 11. In any of the cases, there is little need to allow the remote operation from the electronic cassette 12. Therefore, by setting these as prohibition conditions, it is possible to suppress an unintentional remote operation.

Fifth Embodiment

A fifth embodiment shown in FIGS. 36 and 37 is a form in which a manual operation is prohibited for at least some of displacement mechanisms other than the operation target while a remote operation instruction targeting some of the displacement mechanisms is input. In the mobile radiographic imaging apparatus 11 of the fifth embodiment, for example, a lock mechanism 116 that functions as a brake for the rear wheel 17 is provided in addition to the carriage unit traveling mechanism 57. At the time of positioning, the lock mechanism 116 is normally activated so that the carriage unit 14 of the mobile radiographic imaging apparatus 11 does not travel unintentionally.

Figure 39:
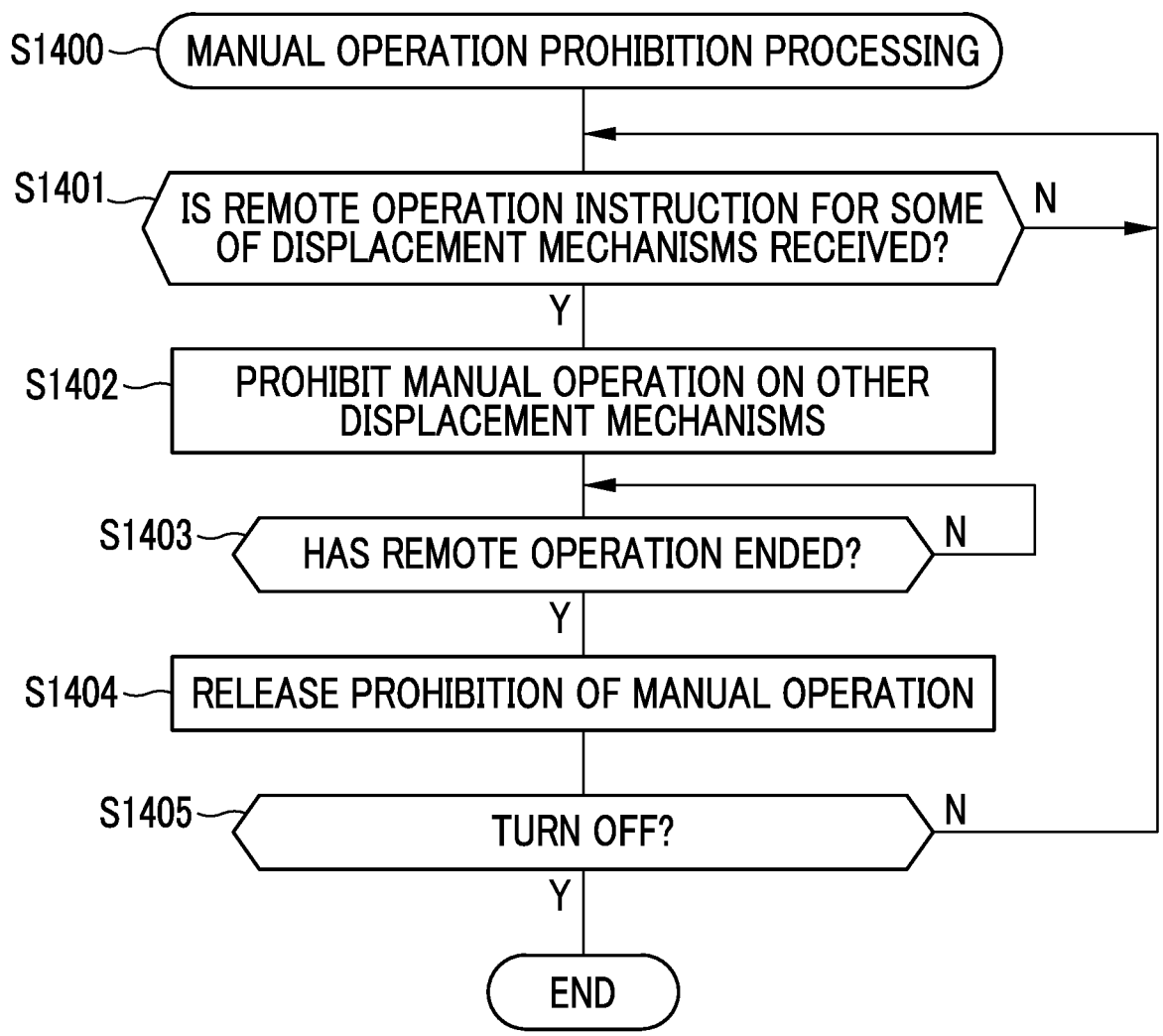
FIG. 39 is a flowchart of the fifth embodiment.

In the fifth embodiment, as shown in FIG. 39, the displacement mechanism controller 61 executes manual operation prohibition processing shown in step S1400. For example, in a case where a remote operation instruction for some of the displacement mechanisms is received in step S1401, the displacement mechanism controller 61 prohibits a manual operation on some of the displacement mechanisms other than the operation target in step S1402.

For example, it is assumed that the displacement mechanism controller 61 receives a remote operation instruction for the irradiation unit rotation mechanism 54. In this case, the displacement mechanism controller 61 drives the irradiation unit rotation mechanism 54 through the irradiation unit rotation controller 61D. In step S1402, the displacement mechanism controller 61 prohibits a manual operation on the carriage unit traveling mechanism 57 that is one of the displacement mechanisms other than the irradiation unit rotation mechanism 54 to be remotely operated. Specifically, by prohibiting unlocking of the lock mechanism 116 of the carriage unit 14, a manual operation, such as manual travel of the carriage unit 14, is prohibited.

Then, in a case where it is determined that the remote operation has ended in step S1403, the displacement mechanism controller 61 proceeds to step S1404 to release the prohibition of the manual operation. In this example, lock release of the lock mechanism 116 is allowed. Such processing is continued until the mobile radiographic imaging apparatus 11 or the electronic cassette 12 is turned off (step S1405).

By prohibiting the manual operation in a state in which the remote operation is performed as described above, the workability of positioning can be improved. For example, according to the fifth embodiment, it is possible to prohibit the traveling of the carriage unit 14 by manual operation of a third party other than the operator OP in a case where the operator OP remotely operates the displacement mechanism from the electronic cassette 12 during positioning. Therefore, since it is possible to reduce repeated positioning, workability is improved. In addition, since it is not preferable from the viewpoint of safety that manual operation is performed simultaneously with remote operation being performed, safety can be improved by prohibiting simultaneous operations of the remote operation and the manual operation.

Needless to say, in the fifth embodiment, the purpose is to prohibit simultaneous operations of the remote operation and the manual operation. In order to change the direction of the radiation emission unit 24, it is allowed to manually operate a plurality of sub-displacement mechanisms at the same time, such as manually operating two sub-displacement mechanisms of the irradiation unit rotation mechanism 54 and the irradiation unit tilting mechanism 56. In addition, it may be allowed to remotely operate a plurality of sub-displacement mechanisms at the same time.

Six Embodiment

Figure 40:
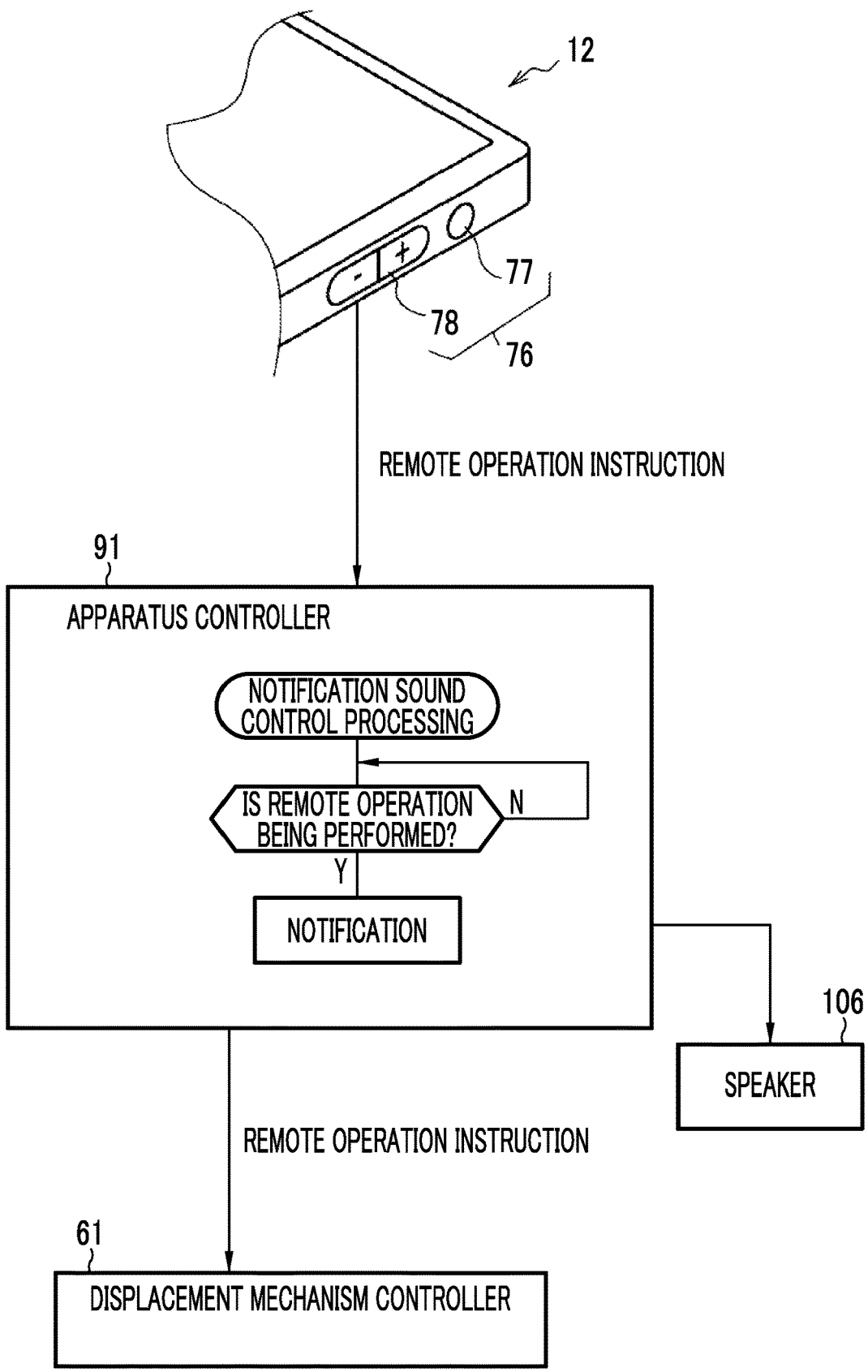
FIG. 40 is a schematic diagram showing a sixth embodiment.

A sixth embodiment shown in FIG. 40 is a form in which a notification unit, which notifies that a displacement mechanism is being remotely operated while the displacement mechanism is being operated by a remote operation from the remote operation unit 76, is provided. The speaker 106 is an example of a notification unit.

In the sixth embodiment, the apparatus controller 91 executes notification sound control processing based on a remote operation instruction. In a case where a remote operation is being performed, the apparatus controller 91 emits sound indicating that the remote operation is being performed through the speaker 106. In this manner, it is possible to call attention to people around the mobile radiographic imaging apparatus 11. Even in a case where the operator OP comes in contact with the remote operation unit 76 accidentally and the displacement mechanism is operating regardless of the intention of the operator OP, the operator OP can be notified through the speaker 106 that the displacement mechanism is operating. Therefore, safety is further improved.

The notification unit may be other than the speaker 106, for example, a warning light. Alternatively, a vibration mechanism that vibrates the electronic cassette 12 may be used as the notification unit. Needless to say, the speaker 106, the warning light, and the vibration mechanism may be appropriately combined.

Seventh Embodiment

Figure 41:
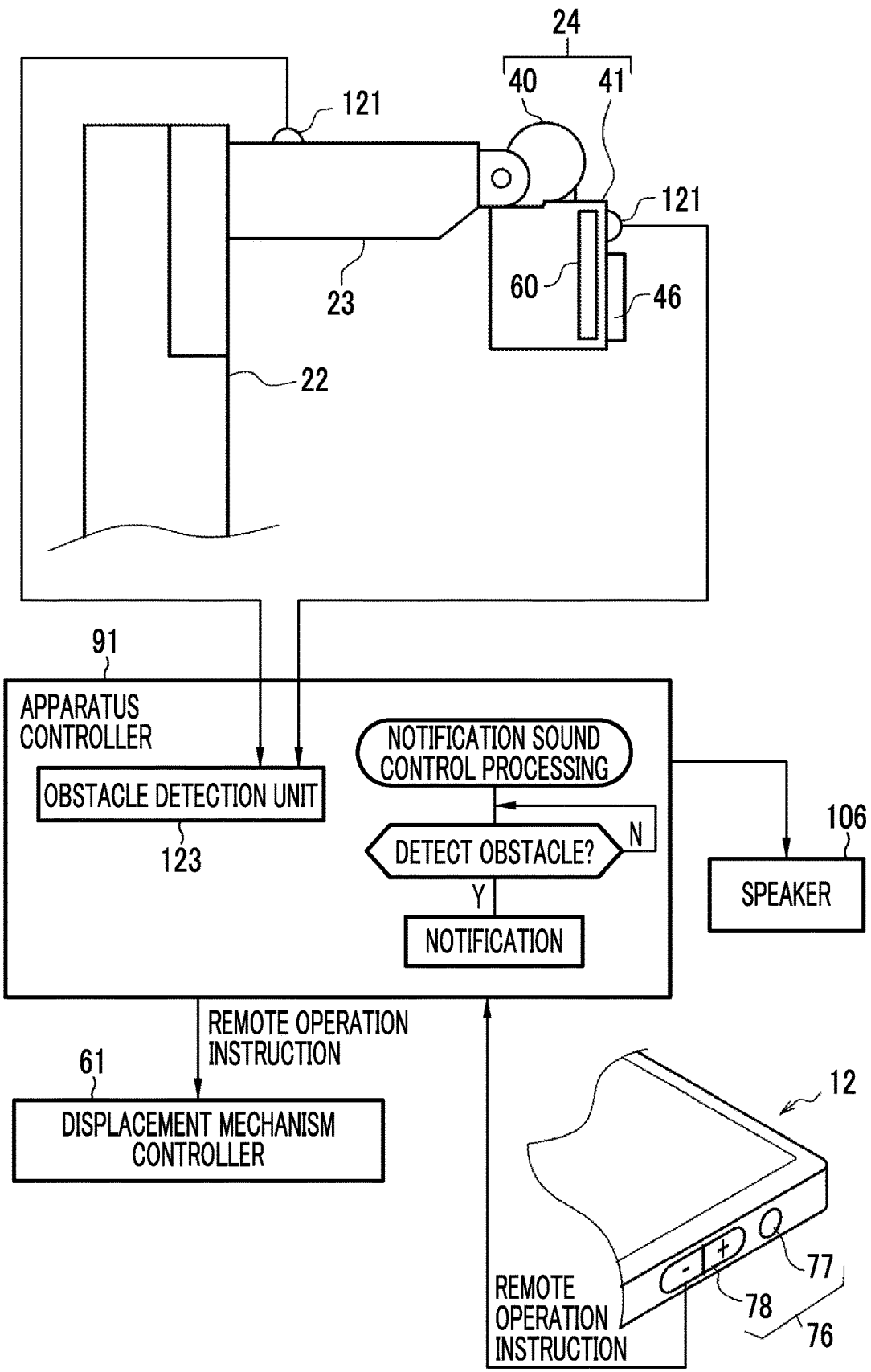
FIG. 41 is a schematic diagram showing a seventh embodiment.

A seventh embodiment shown in FIG. 41 is a form in which an obstacle detection unit 123, which detects whether or not there is an obstacle in a direction in which the radiation emission unit 24 is displaced by the operation of the displacement mechanism, is provided. In the seventh embodiment, a camera 121 is provided in the radiation emission unit 24 and the column 22 of the mobile radiographic imaging apparatus 11. The camera 121 captures an image around the radiation emission unit 24. The apparatus controller 91 acquires the image captured by the camera 121. The apparatus controller 91 comprises the obstacle detection unit 123. The obstacle detection unit 123 detects the presence or absence of an obstacle by analyzing the image captured by the camera 121. The apparatus controller 91 executes notification sound control processing, and provides notification using the speaker 106 in a case where an obstacle is detected.

As described above, the operator OP can grasp that an obstacle is present in a direction in which the radiation emission unit 24 is displaced. In this manner, for example, since collision between the radiation emission unit 24 and an obstacle is avoided or suppressed, safety is further improved.

In a case where an obstacle is detected, the operation of the displacement mechanism may be stopped in addition to notifying that the obstacle has been detected. The notification unit may be other than the speaker 106. In addition, as in the sixth embodiment, a warning light or a vibration mechanism may be used as the notification unit, or these may be appropriately combined.

In each of the embodiments described above, the electronic cassette 12 has been described as an example of the radiographic imaging cassette, the radiographic imaging cassette may be other the electronic cassette 12, or may be a computed radiography (CR) cassette or a film cassette. The CR cassette uses an imaging plate as a radiographic image detection unit. The film cassette uses a silver salt photosensitive material as a radiographic image detection unit.

In each of the embodiments described above, an example has been described in which six sub-displacement mechanisms are provided as displacement mechanisms of the mobile radiographic imaging apparatus 11. However, all of the six sub-displacement mechanisms may not be provided, and at least one of the six sub-displacement mechanisms may be provided. Alternatively, six or more displacement mechanisms may be provided. In addition, all of the plurality of sub-displacement mechanisms may not be operated electrically, and at least one of plurality of sub-displacement mechanisms may be operated electrically.

The sub-displacement mechanisms shown in the above embodiments are examples, and various other sub-displacement mechanisms can be considered. As displacement mechanisms, mechanisms other than the sub-displacement mechanisms exemplified in the above embodiments may be included.

Figure 42:
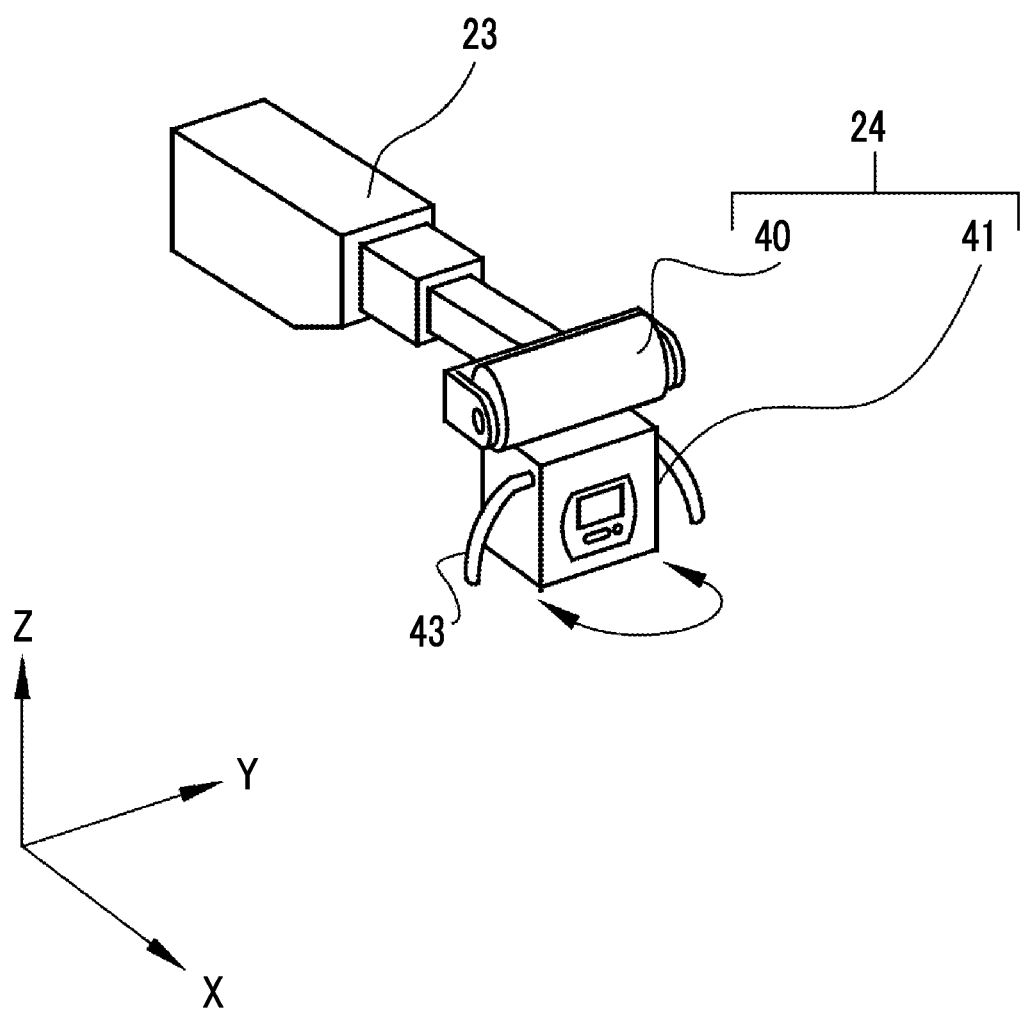
FIG. 42 is a diagram showing an example of the rotation of an irradiation field limiter.

For example, as shown in FIG. 42, in the radiation emission unit 24, a sub-displacement mechanism that rotates the irradiation field limiter 41 around the Z axis with respect to the X-ray tube 40 may be provided.

Figure 43:
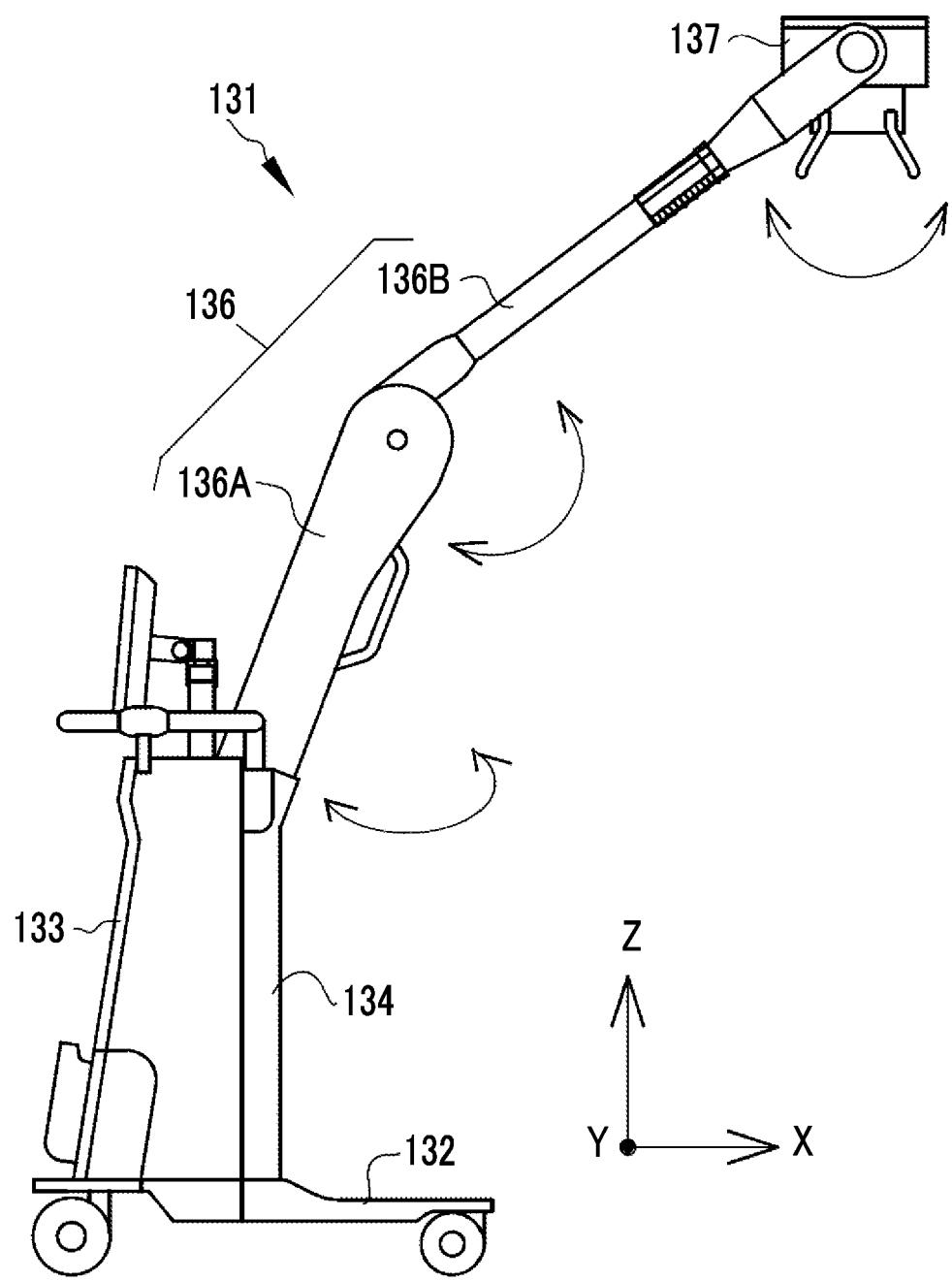
FIG. 43 is a diagram showing another form of the mobile radiographic imaging apparatus.

The forms of the column and the arm may not be the forms shown in the above embodiments. For example, forms of a column 134 and an arm 136 of a mobile radiographic imaging apparatus 131 shown in FIG. 43 may be adopted. The mobile radiographic imaging apparatus 131 has a carriage unit 132, a main body unit 133, the column 134, the arm 136, and a radiation emission unit 137. In the mobile radiographic imaging apparatus 131, the column 134 is erected on the carriage unit 132.

The arm 136 is configured to include a first arm 136A and a second arm 136B. The proximal end of the first arm 136A is attached to the upper end of the column 134 in a posture in which the first arm 136A is inclined forward. The first arm 136A rotates around the Z axis with respect to the column 134 with the proximal end as the center. The proximal end of the second arm 136B is attached to the upper end of the first arm 136A, and the second arm 136B rotates around the Y axis with the proximal end as the center.

The radiation emission unit 137 is provided at the free end of the second arm 136B. The radiation emission unit 137 can rotate around the Y axis. By rotating the arm 136, the vertical position and the horizontal position of the radiation emission unit 137 can be changed. That is, the mechanism for rotating the arm 136 in this example serves as a second displacement mechanism and a third displacement mechanism according to the technique of the present disclosure.

In such a mobile radiographic imaging apparatus 131, it is not necessary to provide a sub-displacement mechanism for electrically displacing all of the column 134, the arm 136, and the radiation emission unit 137. For example, a sub-displacement mechanism capable of electrically performing only the rotation of the radiation emission unit 137 may be provided without providing a sub-displacement mechanism for electrically displacing the column 134 and the arm 136.

Although the remote operation unit comprising the mechanism selection unit and the displacement amount adjustment unit has been described as an example, a plurality of displacement amount adjustment units corresponding to respective sub-displacement mechanisms may be provided without providing the mechanism selection unit, for example.

Although the indicator 66 that displays the name or abbreviation of the selected sub-displacement mechanism has been described as an example of the selected mechanism display unit, the selected mechanism display unit is not limited thereto. For example, instead of displaying the name or abbreviation of the sub-displacement mechanism on the indicator 66, a schematic diagram of the selected sub-displacement mechanism may be displayed. Alternatively, a display lamp, such as a light emitting diode (LED), may be provided for each sub-displacement mechanism, and the display lamp of the selected sub-displacement mechanism may be turned on. Alternatively, notification regarding the selected sub-displacement mechanism may be provided by sound.

The wireless electronic cassette has been described as an example of the electronic cassette, and the wireless method has been described as an example of the operation instruction transmission unit 84. However, a wired electronic cassette may be used, and the operation instruction transmission unit 84 may also use a wired method. The wireless method includes not only a method of transmitting information using radio waves as a medium but also an optical communication method of transmitting information using light as a medium.

In each embodiment described above, for example, various processors shown below can be used as the hardware structures of processing units for executing various kinds of processing, such as the displacement mechanism controller 61, the apparatus controller 91, and the cassette controller 81. The various processors include a central processing unit (CPU) that is a general-purpose processor that executes software to function as various processing units, a programmable logic device (PLD) that is a processor whose circuit configuration can be changed after manufacture, such as a field programmable gate array (FPGA), and/or a dedicated electric circuit that is a processor having a circuit configuration that is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs and/or a combination of a CPU and an FPGA). Alternatively, a plurality of processing units may be configured by one processor.

First, as an example of configuring a plurality of processing units using one processor, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, as the hardware structure of these various processors, it is possible to use an electrical circuit (circuitry) in which circuit elements, such as semiconductor elements, are combined.

In this specification, "A and/or B" is synonymous with "at least one of A or B". That is, "A and/or B" may be only A, only B, or a combination of A and B. In addition, in this specification, the same concept as "A and/or B" is applied to a case where three or more things are expressed with "and/or".

The described content and the illustrated content above are detailed descriptions of portions relevant to the technique of the present disclosure, and are merely examples of the technique of the present disclosure. For example, the above descriptions regarding the configurations, functions, operations, and effects are descriptions regarding examples of the configurations, functions, operations, and effects of portions relevant to the technique of the present disclosure. Therefore, it is needless to say that unnecessary portions may be deleted, new elements may be added, or replacement may be performed for the described content and the illustrated content above without departing from the spirit of the technique of the present disclosure. In addition, in order to avoid complications and facilitate understanding of the portions relevant to the technique of the present disclosure, descriptions regarding common technical knowledge and the like for which descriptions for enabling the implementation of the technique of the present disclosure are not required in particular are omitted.

Explanation of References

What is claimed is:
1. A mobile radiographic imaging system, comprising:
a mobile radiographic imaging apparatus; and
a radiographic imaging cassette,
wherein the mobile radiographic imaging apparatus comprises:
a radiation emission unit that emits radiation;
a carriage unit on which a column, an arm and the radiation emission unit are mounted and which is able to travel, wherein the column is erected on the carriage unit, and the arm has a proximal end provided on the column and a free end that displaceably supports the radiation emission unit;
a displacement mechanism that electrically displaces the radiation emission unit; and
a displacement mechanism controller that controls an operation of the displacement mechanism, and
the radiographic imaging cassette comprises:
a radiographic image detection unit that detects a radiographic image based on the radiation emitted from the radiation emission unit and transmitted through a subject;
a housing in which the radiographic image detection unit is housed;
a remote operation unit that is embedded in the housing and exposed by a surface of the housing so as to remotely operate the displacement mechanism; and
an operation instruction transmission unit that transmits an operation instruction for operating the displacement mechanism to the displacement mechanism controller in a case where the remote operation unit is operated,
wherein the displacement mechanism controller continues an operation of the displacement mechanism until a stop instruction from the operation instruction transmission unit is received by the displacement mechanism controller after receiving the operation instruction once from the operation instruction transmission unit, monitors whether or not a data link between the operation instruction transmission unit and the displacement mechanism controller is established until the stop instruction is received by the displacement mechanism controller after receiving the operation instruction, and stops the operation of the displacement mechanism even though the stop instruction is not received by the displacement mechanism controller in a case where the data link is disconnected.

2. The mobile radiographic imaging system according to claim 1,
wherein the displacement mechanism includes at least one sub-displacement mechanism of a first displacement mechanism that rotates the column around an axis, a second displacement mechanism that changes a position of the radiation emission unit attached to the arm in a vertical direction with respect to the carriage unit, a third displacement mechanism that changes a position of the radiation emission unit attached to the arm in a horizontal direction, which is perpendicular to the vertical direction, with respect to the carriage unit, a fourth displacement mechanism that rotates the radiation emission unit around an axis of the arm, a fifth displacement mechanism that rotates the radiation emission unit around an axis perpendicular to the axis of the arm, or a sixth displacement mechanism that changes the position of the radiation emission unit in the horizontal direction together with the carriage unit by making the carriage unit travel, and the operation instruction transmitted to the displacement mechanism controller by the operation instruction transmission unit includes an operation instruction for operating at least one of the sub-displacement mechanism in the case where the remote operation unit is used.

3. The mobile radiographic imaging system according to claim 1,
wherein the mobile radiographic imaging apparatus comprises an apparatus side operation unit for operating the displacement mechanism, wherein the apparatus side operation unit comprises at least one operation button,
the displacement mechanism controller is able to receive both a remote operation instruction, which is the operation instruction from the remote operation unit, and an apparatus side operation instruction from the apparatus side operation unit, and
in a case of operating the displacement mechanism based on the remote operation instruction, the displacement mechanism controller lowers an operation speed of the displacement mechanism than in a case of operating the displacement mechanism based on the apparatus side operation instruction.

4. The mobile radiographic imaging system according to claim 1,
wherein the radiographic imaging cassette is a wireless electronic cassette having an image detection panel as the radiographic image detection unit that electrically detects the radiographic image based on the radiation and an image transmission unit that wirelessly transmits the radiographic image to the mobile radiographic imaging apparatus, and
the operation instruction transmission unit uses a wireless method.

5. The mobile radiographic imaging system according to claim 1,
wherein the housing has a rectangular front surface that faces the radiation emission unit and receives the radiation, a rectangular back surface on a side opposite to the front surface, and a side surface around the front surface and the back surface, and
the remote operation unit is embedded in the housing at a same side as the back surface or at the side surface.

6. The mobile radiographic imaging system according to claim 1, further comprising:
a posture detection mechanism that detects a first posture of the radiation emission unit and a second posture of the radiographic imaging cassette;
a deriving unit that derives relative posture information regarding a relative posture between the radiation emission unit and the radiographic imaging cassette based on the first posture and the second posture detected by the posture detection mechanism; and
a relative posture information display unit that displays the relative posture information derived by the deriving unit.

7. The mobile radiographic imaging system according to claim 1,
wherein the mobile radiographic imaging apparatus has an irradiation conditions reception unit that receives irradiation conditions of the radiation emission unit, and
the displacement mechanism controller allows a remote operation from the remote operation unit with respect to the displacement mechanism only until the radiation emission unit ends irradiation based on the received irradiation conditions after the irradiation conditions reception unit receives the irradiation conditions.

8. The mobile radiographic imaging system according to claim 1, further comprising:
   a posture detection mechanism that detects a first posture of the radiation emission unit and a second posture of the radiographic imaging cassette; and
   a relative posture determination unit that determines whether or not a relative posture between the radiation emission unit and the radiographic imaging cassette is within an allowable range set in advance based on the first posture and the second posture detected by the posture detection mechanism,
   wherein the displacement mechanism controller allows a remote operation from the remote operation unit with respect to the displacement mechanism only while the relative posture is within the allowable range.

9. The mobile radiographic imaging system according to claim 1,
   wherein the displacement mechanism controller prohibits a remote operation from the remote operation unit with respect to the displacement mechanism when: an irradiation instruction for the radiation emission unit is input, an irradiation detection signal indicating that emission of the radiation has been detected in the radiographic imaging cassette is input, or an operator with the mobile radiographic imaging apparatus is detected.

10. The mobile radiographic imaging system according to claim 1,
   wherein the mobile radiographic imaging apparatus comprises a lock mechanism that locks at least some of the displacement mechanisms, and
   while the operation instruction targeting some of the displacement mechanisms is input, the displacement mechanism controller prohibits a manual operation for at least some of the displacement mechanisms other than the operation target by operating the lock mechanism.

11. The mobile radiographic imaging system according to claim 1,
   wherein the mobile radiographic imaging apparatus comprises a notification unit that notifies that the displacement mechanism is remotely operated while the displacement mechanism is being operated by a remote operation from the remote operation unit.

12. The mobile radiographic imaging system according to claim 1,
   wherein the mobile radiographic imaging apparatus comprises an obstacle detection unit that detects whether or not there is an obstacle in a direction in which the radiation emission unit is displaced by an operation of the displacement mechanism.

13. The mobile radiographic imaging system according to claim 2,
   wherein the at least one sub-displacement mechanism comprises a plurality of displacement mechanisms, and the remote operation unit comprises a mechanism selection unit that selects one of the sub-displacement mechanisms to be operated and a displacement amount adjustment unit that operates the sub-displacement mechanism selected by the mechanism selection unit.

14. The mobile radiographic imaging system according to claim 13,
   wherein the mobile radiographic imaging apparatus comprises a selected mechanism display unit that displays the sub-displacement mechanism selected by the mechanism selection unit.

15. The mobile radiographic imaging system according to claim 4,
   wherein the operation instruction transmission unit and the image transmission unit use a same transmission path.

16. The mobile radiographic imaging system according to claim 4,
   wherein the operation instruction transmission unit and the image transmission unit use different transmission paths.

* * * * *